United States Patent [19]

Kogami et al.

[11] Patent Number: 5,792,791
[45] Date of Patent: Aug. 11, 1998

[54] 2,3-DIHYDROBENZOFURAN DERIVATIVES

[75] Inventors: Yuji Kogami; Daisuke Mochizuki, both of Shizuoka, Japan

[73] Assignee: Asahi Kasei Kogyo Kabushiki Kaisha, Osaka, Japan

[21] Appl. No.: 672,308

[22] Filed: Jun. 28, 1996

Related U.S. Application Data

[63] Continuation of Ser. No. 454,291, filed as PCT/JP93/01835 filed Dec. 17, 1993, abandoned.

[30] Foreign Application Priority Data

| | | | |
|---|---|---|---|
| Jan. 12, 1993 | [JP] | Japan | 5-003067 |
| Aug. 16, 1993 | [JP] | Japan | 5-202365 |

[51] Int. Cl.$^6$ ............... A61K 31/34; C07D 307/81
[52] U.S. Cl. ............... 514/469; 549/467
[58] Field of Search ............... 549/467; 514/469

[56] References Cited

U.S. PATENT DOCUMENTS

| | | | |
|---|---|---|---|
| 4,847,254 | 7/1989 | Boegesoe et al. | 514/256 |
| 5,134,140 | 7/1992 | Stack | 549/467 |
| 5,286,735 | 2/1994 | Bonnaud et al. | 514/321 |

FOREIGN PATENT DOCUMENTS

| | | |
|---|---|---|
| 0538080 | 4/1993 | European Pat. Off. |

*Primary Examiner*—Bernard Dentz
*Attorney, Agent, or Firm*—Birch, Stewart, Kolasch & Birch, LLP

[57] ABSTRACT

Disclosed are a 2,3-dihydrobenzofuran derivative represented by formula (1) or a salt thereof, a method for producing the same, and use thereof:

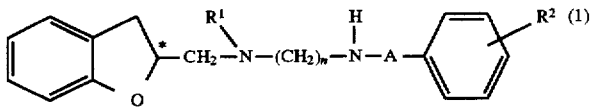

wherein $R^1$ represents a hydrogen atom or a lower alkyl group; n is an integer of from 2 to 6; A represents a carbonyl group or a sulfonyl group; $R^2$ represents a hydrogen atom, a halogen atom, a lower alkyl group (which is unsubstituted or substituted with at least one halogen atom), a lower alkoxy group, a hydroxyl group, a nitro group or a cyano group; and * represents an asymmetric carbon atom.

A 2,3-dihydrobenzofuran derivative of the present invention or a salt thereof has a strong affinity for a serotonin 1A receptor, and, therefore, is useful for prevention and treatment of serotonergic neuron-related diseases, such as anxiety, depression, high blood pressure, emeses (including emeses induced by motion sickness, space sickness and dizziness, etc.) and the like.

22 Claims, No Drawings

2,3-DIHYDROBENZOFURAN DERIVATIVES

This application is a continuation of application Ser. No. 08/454,291 filed on Jun. 15, 1995, now abandoned.

That application is a 371 of PCT/JP93/01835 filed Dec. 17, 1993.

TECHNICAL FIELD

The present invention relates to a novel 2,3-dihydrobenzofuran derivative or a salt thereof, a method for producing the same, and a pharmaceutical composition comprising the same.

BACKGROUND ART

In recent several years, it has been found that serotonin [5-hydroxytryptamine (5-HT)] as a neurotransmitter has correlations with various physiological phenomena, such as appetite, memory, thermoregulation, sleep, sexual behavior, anxiety, depression and stress [Glennon, R. A., J. Med. Chem., 30,1 (1987)].

It has been known that compounds acting on a 5-HT 1A receptor which is one of the serotonin-susceptive receptors are useful for preventing and treating anxiety, depression, eating disorder, high blood pressure, emeses (including emeses induced by motion sickness, space sickness, dizziness and drug, etc.), and the like. With respect to such compounds, a number of studies have been made and the results thereof have been reported [see, "Nippon Rinsho (Japanese Journal of Clinical Medicine)" vol. 47, special edition, pp. 1241–1248 (1989); J. P. Feighnev, W. F. Boyer, Psychopathology, 22, 21 (1989); P. R. Saxena, C. M. Villalon, TIPS, 11, 95 (1990); N. Matsuki, et al., Jpn. J. Pharmacol. Suppl., 58, 313 (1992); etc.].

Problems to be Solved by the Invention

It has been desired in the art to develop and provide a compound which is improved with respect to the above-mentioned pharmacological activities.

Means for Solving the Problems

In these situations, the present inventors have made extensive and intensive studies, in which various types of compounds were synthesized and examined with respect to the pharmacological properties thereof. As a result, it has unexpectedly been found that novel 2,3-dihydrobenzofuran derivatives of the present invention exhibit an excellent affinity for a serotonin-susceptive 5-HT1A receptor and excellent pharmacological activities on such a receptor. The present invention has been completed, based on the above novel findings.

Disclosure of the Invention

Accordingly, in one aspect of the present invention, there is provided a novel 2,3-dihydrobenzofuran derivative or a salt thereof, wherein the 2,3-dihydrobenzofuran derivative is represented by formula (1) [hereinafter, frequently referred to as "compound (1)"]:

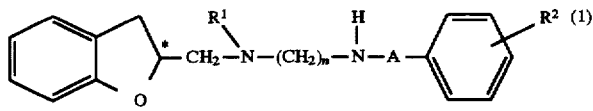

wherein $R^1$ represents a hydrogen atom or a lower alkyl group; n is an integer of from 2 to 6; A represents a carbonyl group or a sulfonyl group; $R^2$ represents a hydrogen atom, a halogen atom, a lower alkyl group (which is unsubstituted or substituted with at least one halogen atom), a lower alkoxy group, a hydroxyl group, a nitro group or a cyano group; and * represents an asymmetric carbon atom.

In another aspect of the present invention, there is provided a method for producing a 2,3-dihydrobenzofuran derivative represented by formula (1) above or a salt thereof.

In a further aspect of the present invention, there is provided a pharmaceutical composition for treating a serotonergic neuron-related disease, which comprises a 2,3-dihydrobenzofuran derivative represented by formula (1) above or a salt thereof.

In still a further aspect of the present invention, there is provided a method for treating a serotonergic neuron-related disease, which comprises administering to a patient suffering from a serotonergic neuron-related disease a pharmaceutical composition comprising a therapeutically effective amount of a 2,3-dihydrobenzofuran derivative represented by formula (1) or a non-toxic salt thereof:

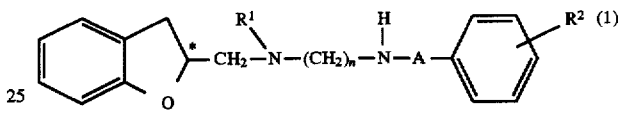

wherein $R^1$ represents a hydrogen atom or a lower alkyl group; n is an integer of from 2 to 6; A represents a carbonyl group or a sulfonyl group; $R^2$ represents a hydrogen atom, a halogen atom, a lower alkyl group which is unsubstituted or substituted with at least one halogen atom, a lower alkoxy group, a hydroxyl group, a nitro group, or a cyano group; and * represents an asymmetric carbon atom.

DETAILED DESCRIPTION OF THE INVENTION

In the present invention, the lower alkyl group means a straight chain or branched $C_1$–$C_4$ alkyl group. Specific examples of lower alkyl groups include methyl, ethyl, propyl, butyl, isopropyl, isobutyl, sec-butyl and tert-butyl.

In the present invention, the lower alkoxy group means a straight chain or branched $C_1$–$C_4$ alkoxy group. Specific examples of lower alkoxy groups include methoxy, ethoxy, propoxy, butoxy, isopropoxy, isobutoxy, sec-butoxy and tert-butoxy.

Specific examples of halogen atoms include a fluorine atom, a chlorine atom, a bromine atom and an iodine atom.

In the present invention, the term "a lower alkyl group which is unsubstituted or substituted with at least one halogen atom" means that the lower alkyl group may be partially or entirely substituted with at least one halogen atom. When the lower alkyl group is substituted with a plurality of halogen atoms, each of the halogen atoms may be the same or different. Further, in the case of the lower alkyl group which is substituted with a plurality of halogen atoms, there is no particular limitation with respect to the positions of halogen substitution in the lower alkyl group. Specific examples of lower alkyl groups which are unsubstituted or substituted with at least one halogen atom include a trifluoromethyl group, a difluoromethyl group, a methyl group, an ethyl group and a tert-butyl group.

Compound (1) of the present invention is produced by a method which comprises reacting a compound represented by formula (2) [hereinafter, frequently referred to as "compound (2)"]:

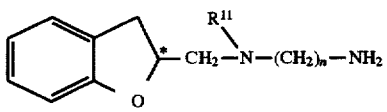

wherein * and n are as defined for formula (1) above; and $R^{11}$ represents an amino-protecting group or a lower alkyl group,
with a compound represented by formula (3) [hereinafter frequently referred to as "compound (3)"]:

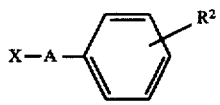

wherein $R^2$ and A are as defined for formula (1) above; and X represents a leaving atom or group,
wherein when $R^{11}$ in formula (2) is an imino-protecting group, a product obtained by the reaction of the compound represented by formula (2) with the compound represented by formula (3) is subsequently subjected to a treatment for removing the amino-protecting group so that a hydrogen atom is substituted therefor.

By the above reaction of compound (2) with compound (3), a compound represented by formula (4):

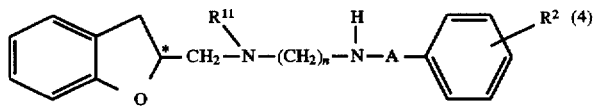

wherein $R^{11}$, $R^2$, A, * and n are as defined for formulae (1) and (2) above, is obtained. When $R^{11}$ in formula (4) is an amino-protecting group, the compound represented by formula (4) is subsequently subjected to a treatment for removing the amino-protecting group so that a hydrogen atom is substituted therefor, to thereby obtain a compound represented by formula (1), wherein $R^1$ is a hydrogen atom. If desired, the thus obtained compound may be treated with an alkylating agent mentioned below, to thereby replace the hydrogen atom with a lower alkyl group.

In the present invention, the amino-protecting group as $R^{11}$ is a group which protects the amino moiety (having $R^{11}$ bonded thereto) from undesired side reactions involving the amino moiety during the reaction of compound (2) with compound (3), and which can be easily eliminated without danger of the desired compound suffering unintended reactions. With respect to such an amino-protecting group, reference can be made to the known literature [see, for example, Green, "Protective groups in organic synthesis", chapter 7, 1981; Green, Wuts, "Protective groups in organic synthesis" second edition, chapter 7, 1991]. Specific examples of amino-protecting groups include a tert-butoxycarbonyl group (Boc group), a benzyloxycarbonyl group (Cbz group), a 9-fluorenyloxycarbonyl group (Fmoc group), an ethoxycarbonyl group, a methoxycarbonyl group, an acetyl group and a benzyl group.

With respect to the method for the preparation of compound (2), explanation is made below.

In the present invention, leaving atom or group X in compound (3) is an atom or group which can be eliminated from compound (3) during the reaction of compound (2) with compound (3) for producing compound (4). Generally, as the leaving group, an atom or group having a high reactivity, such as a chlorine atom, a bromine atom and a group constituting a symmetric acid anhydride, can be used.

Further, a hydroxyl group can also be used as the leaving group. In this case, it is preferred that the hydroxyl group be used in combination with an acid activator mentioned below.

Compounds (3) are known compounds. Examples of compounds (3) include benzoyl chloride, benzoyl bromide, benzenesulfonyl chloride, benzoic anhydride, o-methylbenzoyl chloride, p-butylbenzoyl chloride, o-methoxybenzoyl chloride, m-methoxybenzoyl chloride, p-methoxybenzoyl chloride, o-chlorobenzoyl chloride, o-bromobenzoyl chloride, o-fluorobenzoyl chloride, o-trifluoromethylbenzoyl chloride, p-trifluoromethylbenzoyl chloride, o-nitrobenzoyl chloride, m-cyanobenzoyl chloride, p-methoxybenzenesulfonyl chloride, p-chlorobenzenesulfonyl chloride, p-nitrobenzenesulfonyl chloride and p-bromobenzenesulfonyl chloride. Such compounds as mentioned above are commercially available, and sold by, for example, Tokyo Kasei Kogyo Co., Ltd., Japan and Aldrich Chemical Co., Inc., U.S.A. Therefore, these compounds can be readily obtained and used.

The reaction of compound (2) with compound (3) can be conducted by conventionally known amidation techniques. Specifically, the above reaction can be conducted by reacting compound (2) with compound (3) in an inert medium. Examples of inert media include chloroform, methylene chloride, diethyl ether and tetrahydrofuran. With respect to the amount of each of compounds (2) and (3), compound (3) is generally used in an amount within the range of from 0.1 to 10 equivalents, preferably 1 to 2 equivalents per equivalent of compound (2). The amount of the inert medium may be appropriately selected. For example, the inert medium is used in a volume amount which is 5 to 100 times the volume amount of compound (2). The reaction can be generally conducted at room temperature. The completion of reaction can be confirmed by observing the disappearance of the starting material. Generally, the reaction is completed within 1 hour to 3 days.

Further, it is preferred that the reaction of compound (2) with compound (3) be conducted in the presence of a basic compound which may also function as an inert medium. Examples of basic compounds include organic basic compounds, such as triethylamine, pyridine and 4-methylmorpholine; and inorganic basic compounds, such as potassium carbonate, sodium carbonate and sodium hydrogencarbonate. The basic compound is used preferably in an equivalent amount to the amount of compound (3), or in slight excess relative to the amount of compound (3), for example, about 1.5 equivalents per equivalent of compound (3).

When compound (3) has a hydroxyl group as leaving group X, it is preferred that an acid activator be used in the reaction of compound (2) with compound (3). Examples of acid activators include isobutylchloroformate, ethylchloroformate, methylchloroformate, dicyclohexylcarbodiimide, 1-ethyl-3-(3-dimethylaminopropyl)carbodiimide, N-hydroxysuccinimide and N-hydroxybenzotriazole.

For example, when a chloroformic ester, such as isobutylchloroformate, ethylchloroformate or methylchloroformate, is used as an acid activator, compound (3) having a hydroxyl group, which is an acid, such as a benzoic acid or a p-methoxybenzoic acid, can be activated by a reaction thereof with the chloroformic ester (such as isobutylchloroformate, ethylchloroformate or methylchloroformate) in an inert medium in the presence of a basic compound. Examples of basic compounds include organic basic compounds, such as triethylamine, pyridine and 4-methylmorpholine; and inorganic basic compounds, such as potassium carbonate, sodium carbonate and sodium hydrogencarbonate. The above-mentioned basic compounds may also function as an inert medium. The above-mentioned acid activator is used in an amount within the range of from 1 to 5 equivalents, preferably 1 to 1.5 equivalents per equivalent of compound (3). The basic compound is used in an amount within the range of from 1 to 2 equivalents, preferably 1 to 1.5 equivalents per equivalent of the acid activator used in the reaction. With respect to the inert medium, there is no particular limitation as long as the medium is inert to the reaction system. The amount of the inert medium may be appropriately selected. However, the inert medium can generally be used in a volume amount which is 5 to 100 times the volume amount of compound (3) used for the reaction. The reaction can be conducted at room temperature, however, preferably at a relatively low temperature of from about −25° C. to about 5° C. The completion of reaction can be confirmed by observing the disappearance of the starting material. Generally, the reaction is completed within 15 minutes to 2 hours to obtain a reaction mixture. The acid derivative of compound (3) activated by an acid activator may or may not be isolated from the reaction mixture before being used for a reaction with compound (2). Generally, however, the acid derivative of compound (3) is not isolated from the reaction mixture, but the obtained reaction mixture containing the acid derivative of compound (3) can be reacted in situ with compound (2).

As a result of the above-mentioned reaction of compound (2) with compound (3), compound (4) is obtained. When compound (4) has an amino-protecting group as $R^{11}$, the amino-protecting group must be eliminated. Compound (4) may be isolated and purified from the reaction mixtures. In this case, the purification of the compound can be conducted by known methods, such as column chromatography, using silica gel or the like as a solid phase.

As a method for the elimination of the amino-protecting group (deblocking), a known method can be employed, and an appropriate method is selected depending on the type of amino-protecting group. For example, when the amino-protecting group is tert-butoxycarbonyl group (Boc group) or the like, the deblocking is conducted by contacting a compound having an amino-protecting group with an acid, such as hydrochloric acid, sulfuric acid or trifluoroacetic acid. The acid for the deblocking is generally used in an amount of 1 equivalent or more, preferably from 1 to 100 equivalents per equivalent of compound (4). In this case, the acid may be diluted with a solvent. Examples of such solvents include chloroform, methylene chloride, diethyl ether, tetrahydrofuran, methanol and water. Generally, the reaction is conducted at a temperature of from −25° C. to 40° C., preferably around 0° C. The completion of reaction can be confirmed by observing the disappearance of the starting material. When it is observed that the desired compound is formed in an amount larger than intended, the reaction can be terminated. Generally, the reaction is completed within 1 hour to 24 hours.

When the amino-protecting group is a benzyloxycarbonyl group (Cbz group), a benzyl group or the like, the deblocking can be conducted by contacting a compound having an amino-protecting group with a hydrogen gas in the presence of a catalyst, such as palladium black, palladium-activated carbon or platinum oxide. In this case, examples of solvents usable for the deblocking include diethyl ether, tetrahydrofuran, methanol, ethyl acetate, dimethylformamide and water. The deblocking reaction can be conducted under cooled or heated conditions, however, preferably at room temperature. The completion of reaction can be confirmed by observing the disappearance of the starting material. When it is observed that the desired compound is formed in an amount larger than intended, the reaction can be terminated. Generally, the reaction is completed within 1 hour to 3 days.

Further, when the amino-protecting group is a benzyloxycarbonyl group (Cbz group) or the like, the deblocking can be conducted using an acid, such as a solution of hydrobromic acid in acetic acid, trifluoroacetic acid, aluminum chloride, boron tribromide or the like. The acid for the deblocking is usually used in an amount of 1 equivalent or more, preferably from 1 to 100 equivalents per equivalent of compound (4). In this case, the acid may be diluted with a solvent. Examples of such solvents include chloroform, methylene chloride, diethyl ether and tetrahydrofuran. Further, it is preferred that a scavenger, such as anisole and thioanisole, be present in the reaction system in order to capture benzyl cations formed during the reaction. The scavenger is generally used in an amount of 1 equivalent or more, preferably from 1 to 100 equivalents per equivalent of compound (4). The reaction can be conducted under cooled or heated conditions, however, preferably at a temperature of from 0° C. to room temperature. The completion of reaction can be confirmed by observing the disappearance of the starting material. When it is observed that the desired compound is formed in an amount larger than intended, the reaction can be terminated. Generally, the reaction is completed within 1 hour to 3 days.

When the amino-protecting group is a 9-fluorenyloxycarbonyl group (Fmoc group), an ethoxycarbonyl group, a methoxycarbonyl group, an acetyl group or the like, the deblocking can be conducted using an organic basic compound (such as morpholine) or an inorganic basic compound (such as sodium hydroxide).

In the present invention, compound (1) having a hydrogen atom as $R^1$ can be obtained in such manner as mentioned above. Further, when it is intended to produce a compound having a lower alkyl group as $R^1$ from the compound having a hydrogen atom as $R^1$, it is possible to replace the hydrogen atom with a lower alkyl group using an alkylating agent mentioned below, to thereby obtain compound (1) having a lower alkyl group as $R^1$.

Compound (2) can be prepared by, for example, the following method. That is, compound (2) can be prepared by reducing a compound represented by formula (5) [hereinafter, frequently referred to as "compound (5)"]:

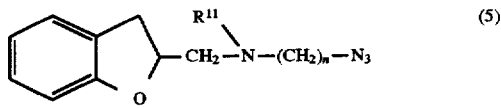

wherein $R^{11}$ and n are as defined for formulae (1) and (2) above.

Specifically, the reduction of compound (5) can be conducted using a palladium-activated carbon, while introducing a hydrogen gas to the reaction system. In this case, the catalyst is generally used in an amount of 1 to 20% by weight, preferably of 5 to 10% by weight, based on the weight of compound (5). With respect to palladium-activated carbon, a commercially available palladium-activated carbon can be used and, generally, 5% palladium-activated carbon or 10% palladium-activated carbon is used. As an example of other methods for reducing compound (5), there can be mentioned a method in which lithium aluminum hydride, sodium borohydride or the like is used. The reduction reaction is generally conducted in an inert medium. In the present invention, there is no particular limitation with respect to the inert medium as long as the medium is inert to the reaction system. Examples of inert media include dimethylformamide, dimethylacetamide, diethyl ether, tetrahydrofuran, methanol, ethanol and water. The amount of the inert medium is appropriately selected. For example, the inert medium can be used in a volume amount which is 5 to 100 times the volume amount of compound (5). The reaction can be conducted under cooled or heated conditions, however, preferably at room temperature. The completion of reaction can be confirmed by observing the disappearance of the starting material. The reaction is generally completed within 30 minutes to 3 days. With respect to $R^{11}$ of compound (5), when $R^{11}$ is an amino-protecting group, undesirable elimination of the amino-protecting group may occur during the reduction reaction, depending on the type of the amino-protecting group. Therefore, it is necessary to select an amino-protecting group which will not be eliminated during the reduction reaction. When the amino-protecting group is eliminated during the reduction reaction, it is necessary to introduce an amino-protecting group again.

Further, compound (5) can be obtained by reacting a compound represented by formula (6) [hereinafter, frequently referred to as "compound (6)"]:

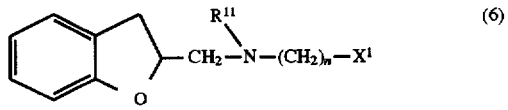

wherein $R^{11}$ and n are as defined for formulae (1) and (2) above; and $X^1$ represents a leaving atom or group, with an azidation agent.

The leaving atom or group $X^1$ means an atom or group which is eliminated from compound (6) during the reaction of compound (6) with the azidation agent so that it is replaced by an azido group. Examples of leaving atom or group $X^1$ include a halogen atom, such as a chlorine atom or a bromine atom, a methanesulfonyloxy group and a p-toluenesulfonyloxy group.

Examples of azidation agents include sodium azide and lithium azide. The azidation agent can be used in an amount of from 1 to 10 equivalents, preferably 1 to 3 equivalents per equivalent of compound (6). The reaction is generally conducted in an inert medium. With respect to the inert medium, there is no particular limitation as long as the medium is inert to the reaction system. Examples of inert media include dimethylformamide, dimethylacetamide, diethyl ether, tetrahydrofuran, chloroform and methylene chloride. Of these, dimethylformamide is especially preferred. The amount of the inert medium may be appropriately selected. For example, the inert medium is used in a volume amount which is 5 to 100 times the volume amount of compound (6). Generally, the reaction is conducted under cooled or heated conditions, preferably under heated conditions. The completion of reaction can be confirmed by observing the disappearance of the starting material. The reaction is generally completed within 1 hour to 24 hours.

Compound (6) having a methanesulfonyloxy group or a p-toluenesulfonyloxy group as $X^1$ can be obtained by reacting a compound represented by formula (7) [hereinafter, frequently referred to as "compound (7)"]:

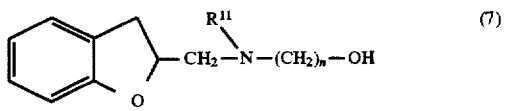

wherein $R^{11}$ and n are as defined for formulae (1) and (2) above, with a sulfonylation agent, such as p-toluenesulfonyl chloride, p-toluenesulfonic anhydride or methanesulfonyl chloride.

The sulfonylation agent can be used in an amount is within the range of from 1 to 10 equivalents, preferably 1 to 1.5 equivalents per equivalent of compound (7). It is preferred that the reaction of compound (7) with a sulfonylation agent be conducted in the presence of a basic compound. Examples of basic compounds include organic basic compounds, such as triethylamine; pyridine and 4-methylmorpholine; and inorganic basic compounds, such as potassium carbonate, sodium carbonate and sodium hydrogencarbonate. The basic compound is used preferably in an equivalent amount or in slight excess amount relative to the amount of the sulfonylation agent, e.g., about 1.5 equivalents per equivalent of the sulfonylation agent. The reaction is generally conducted in an inert medium. With respect to the inert medium, there is no particular limitation as long as the medium is inert to the reaction system. Examples of inert media include, chloroform, methylene chloride, diethyl ether and tetrahydrofuran. The amount of the inert medium may be appropriately selected. For example, the inert medium is used in a volume amount which is 5 to 100 times the volume amount of compound (7). The reaction is generally conducted at a temperature of from −25° C. to 40° C., preferably at room temperature. The completion of reaction can be confirmed by observing the disappearance of the starting material. Generally, the reaction is completed within 1 hour to 24 hours.

Compound (6) having, as $X^1$, a halogen atom, such as a chlorine atom, a bromine atom, or the like, can be obtained by reacting the above-mentioned compound (7) with a halogen-containing compound in the presence of a phosphine compound, such as triphenylphosphine, and, optionally, an azo compound, such as diethyl azodicarboxylate. Examples of halogen-containing compounds include carbon tetrachloride and carbon tetrabromide. The halogen-containing compound is generally used in an equivalent amount or more than the amount of compound (7), or may be used in an amount of 10 equivalents or more per equivalent of compound (7). A phosphine compound (such as triphenylphosphine and an azo compound (such as diethyl azodicarboxylate) may be used in an amount of from 1 to 10 equivalents, preferably 1 to 3 equivalents per equivalent of compound (7). The reaction is generally conducted in an inert medium. Examples of inert media include dimethylformamide, dimethylacetamide, diethyl ether and tetrahydrofuran. A halogen-containing compound can be used instead of the inert medium. The amount of the inert medium may be appropriately selected. For example, the inert medium is used in a volume amount which is 5 to 100 times the volume amount of compound (7). The reaction can be conducted under cooled or heated conditions, however, preferably at room temperature. The completion of reaction can be confirmed by observing the disappearance of the starting material. Generally, the reaction is completed within 30 minutes to 1 day.

Compound (7) can be obtained by a conventional method. For example, compound (7) having a lower alkyl group as $R^1$ can be obtained from a compound represented by formula (8) [hereinafter, frequently referred to as "compound (8)"]:

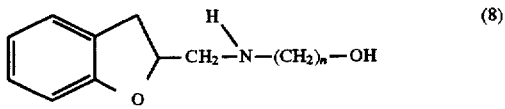

wherein n is as defined for formula (1) above, by introducing a lower alkyl group to compound (8) by the use of an alkylating agent, such as methyl iodide, ethyl iodide, propyl iodide, isopropyl iodide and methyl bromide.

These alkylating agents may be used in an amount within the range of from 1 to 10 equivalents, preferably 1 to 3 equivalents per equivalent of compound (8). It is preferred that the reaction be conducted in the presence of a basic compound. Examples of basic compounds include organic basic compounds, such as triethylamine, pyridine and 4-methylmorpholine; and inorganic basic compounds, such as potassium carbonate, sodium carbonate and sodium hydrogencarbonate. The reaction is generally conducted in an inert medium. Examples of inert media include chloroform, methylene chloride, diethyl ether, tetrahydrofuran and acetonitrile. The amount of the inert medium may be appropriately selected. For example, the inert medium is used in a volume amount which is 5 to 100 times the volume amount of compound (8). The reaction is generally conducted at a temperature of from $-25°$ C. to $40°$ C., preferably at room temperature. The completion of reaction can be confirmed by observing the disappearance of the starting material. Generally, the reaction is completed within 1 hour to 3 days.

As an example of other methods for producing compound (7) having a lower alkyl group as $R^{11}$, there can be mentioned a method in which the above-mentioned compound (8) is reacted with an aldehyde reagent (such as an aqueous solution of formaldehyde, a solution of formaldehyde or acetaldehyde in an alcohol), followed by reduction using a reducing agent (such as sodium borohydride or sodium cyanoborohydride), thereby obtaining compound (7) having a lower alkyl group as $R^{11}$. The aldehyde reagent may be used in an amount of from 1 to 10 equivalents, preferably 1 to 3 equivalents per equivalent of compound (8). The reducing agent may be used in an amount of from 1 to 10 equivalents, preferably 1 to 3 equivalents per equivalent of compound (8). The reduction reaction is generally conducted in an inert medium. In the present invention, there is no particular limitation with respect to the inert medium as long as the medium is inert to the reaction system. Examples of inert media include diethyl ether, tetrahydrofuran, methanol and ethanol. The amount of the inert medium may be appropriately selected. For example, the inert medium is used in a volume amount which is 5 to 100 times the volume amount of compound (8). Generally, the reaction is conducted at a temperature of from $-25°$ C. to $40°$ C., preferably at room temperature. The completion of reaction can be confirmed by the disappearance of the starting material. Generally, the reaction is completed within 1 hour to 3 days.

Compound (7) having an amino-protecting group as $R^1$l can be produced by reacting compound (8) with a protecting agent, such as di-tert-butyl dicarbonate ($Boc_2O$), benzyloxycarbonyl chloride (Cbz-Cl) or 9-fluorenylmethyl chloroformate (Fmoc-Cl). The protecting agent may be used in an amount of from 1 to 10 equivalents, preferably 1 to 3 equivalents per equivalent of compound (8). It is preferred that the reaction of compound (8) with a protecting agent be conducted in the presence of a basic compound. Examples of basic compounds include organic basic compounds, such as triethylamine, pyridine and 4-methylmorpholine; and inorganic basic compounds, such as potassium carbonate, sodium carbonate and sodium hydrogencarbonate. Generally, the reaction is conducted in an inert medium. Examples of inert media include chloroform, methylene chloride, diethyl ether and tetrahydrofuran. The amount of the inert medium may be appropriately selected. For example, the inert medium is used in a volume amount which is 5 to 100 times the volume amount of compound (8). Generally, the reaction is conducted at a temperature of from $-25°$ C. to $40°$ C., preferably at room temperature. The completion of reaction can be confirmed by observing the disappearance of the starting material. Generally, the reaction is completed within 1 hour to 24 hours.

Compound (8) can be obtained by a conventional method. For example, compound (8) can be obtained by reacting a compound represented by formula (9) [hereinafter, frequently referred to as "compound (9)"]:

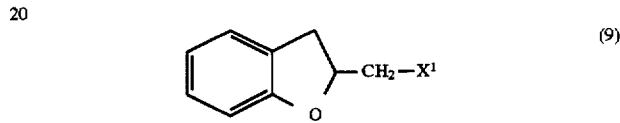

wherein $X^1$ is as defined for formula (6) above, with an amino alcohol, such as 2-aminoethanol, 3-amino-1-propanol, 4-amino-1-butanol, 5-amino-1-pentanol or 6-amino-1-hexanol.

The amino alcohol can be used in an equivalent amount or more than the amount of compound (9), preferably 3 to 5 equivalents per equivalent of compound (9). The reaction is generally conducted in an inert medium. It is preferred that the reaction of compound (9) with an amino alcohol be conducted in the presence of a basic compound. Examples of basic compounds include organic basic compounds, such as triethylamine, pyridine and 4-methylmorpholine; and inorganic basic compounds, such as potassium carbonate, sodium carbonate and sodium hydrogencarbonate. The above-mentioned basic compound may also function as an inert medium. The above-mentioned amino alcohol may also function as a basic compound or an inert medium.

Examples of inert media include dimethylformamide, dimethylacetamide, diethyl ether, tetrahydrofuran, methanol, ethanol and acetonitrile. The amount of the inert medium may be appropriately selected. For example, the inert medium is used in a volume amount which is 5 to 100 times the volume amount of compound (9). The reaction can be conducted under cooled or heated conditions, preferably under heated conditions. The completion of reaction can be confirmed by observing the disappearance of the starting material. Generally, the reaction is completed within 3 hours to 2 days.

With respect to the method for producing compound (9), reference can be made to Yakugaku Zasshi (Journal of Pharmacology) 88(5), 503–512 (1968) and Unexamined Japanese Patent Application Laid-Open Specification No. 3-188077. According to the methods disclosed therein, compound (9) can be synthesized from commercially available 2-allylphenol.

As an example of other methods for producing compound (2), there can be mentioned a method in which compound (2) is produced by reacting a compound represented by formula (10) [hereinafter, frequently referred to as "compound (10)"]:

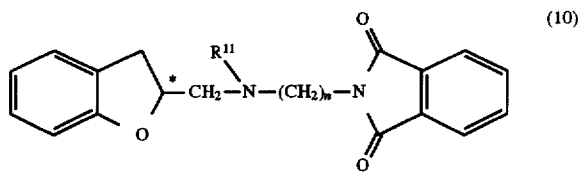

wherein *, n, R¹¹ are as defined for formulae (1) and (2) above,
with a hydrazine reagent to thereby remove the phthalimide group.

The hydrazine reagent can be used in an amount of from 1 to 10 equivalents, preferably 1 to 3 equivalents per equivalent of compound (10). Examples of hydrazine reagents include hydrazine anhydride, 100% hydrate of hydrazine and 80% aqueous hydrazine. The reaction is generally conducted in an inert medium. With respect to the inert medium, there is no particular limitation as long as the medium is inert to the reaction system. Examples of inert media include diethyl ether, tetrahydrofuran, methanol, ethanol and water. The amount of the inert medium may be appropriately selected. For example, the inert medium is used in a volume amount which is 5 to 100 times the volume amount of compound (10). The reaction can be conducted under cooled or heated conditions, however, preferably at room temperature. The completion of reaction can be confirmed by observing the disappearance of the starting material. Generally, the reaction is completed within 30 minutes to 3 days.

Compound (10) can be obtained, for example, by reacting a compound represented by formula (11) [hereinafter, frequently referred to as "compound (11)"]:

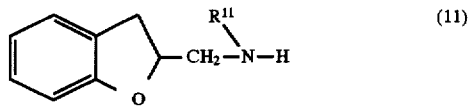

wherein R¹¹ is as defined for formula (2) above, with an imide reagent, such as N-(2-bromoethyl)phthalimide, N-(3-bromopropyl)phthalimide or N-(4-bromobutyl)phthalimide.

The imide reagent can be produced by a conventional method. Further, the imide reagent is commercially available and sold by, for example, Tokyo Kasei Kogyo Co., Ltd., Japan and Aldrich Chemical Co., Inc., U.S.A. Therefore, the imide reagent is readily obtained and used. The imide reagent is generally used in an equivalent amount or more than the amount of compound (11), preferably 1 to 5 equivalents per equivalent of compound (11). The reaction is generally conducted in an inert medium. Examples of inert media include dimethylformamide, dimethylacetamide, diethyl ether, tetrahydrofuran, methanol, ethanol and acetonitrile. The amount of the inert medium may be appropriately selected. For example, the inert medium is used in a volume amount which is 5 to 100 times the volume amount of compound (11). Generally, the reaction is conducted under cooled or heated conditions, preferably under heated conditions. The completion of reaction can be confirmed by observing the disappearance of the starting material. Generally, the reaction is completed within 3 hours to 2 days. It is preferred that the reaction be conducted in the presence of a basic compound. Examples of basic compounds include organic basic compounds, such as triethylamine, pyridine and 4-methylmorpholine; and inorganic basic compounds, such as potassium carbonate, sodium carbonate and sodium hydrogencarbonate. The above-mentioned basic compound may also function as an inert medium.

Compound (11) can be obtained, for example, by reacting the above-mentioned compound (9) with an amine compound, such as benzylamine, 4-methoxybenzylamine, 3,4-dimethoxybenzylamine, diphenylmethylamine or triphenylmethylamine.

The amine compound can be produced by a conventional method. Further, the amine compound is commercially available and sold by, for example, Tokyo Kasei Kogyo Co., Ltd., Japan and Aldrich Chemical Co., Inc., U.S.A. Therefore, the amine compound can be readily obtained and used. The amine compound is generally used in an equivalent amount or more than the amount of compound (9), preferably 1 to 5 equivalents per equivalent of compound (9). The reaction is generally conducted in an inert medium. Examples of inert media include dimethylformamide, dimethylacetamide, diethyl ether, tetrahydrofuran, methanol, ethanol and acetonitrile. The amount of the inert medium may be appropriately selected. For example, the inert medium is used in a volume amount which is 5 to 100 times the volume amount of compound (9). Generally, the reaction is conducted under cooled or heated conditions, preferably under heated conditions. The completion of reaction can be confirmed by observing the disappearance of the starting material. Generally, the reaction is completed within 3 hours to 2 days. It is preferred that the reaction of compound (9) with an amine compound be conducted in the presence of a basic compound. Examples of basic compounds include organic basic compounds, such as triethylamine, pyridine and 4-methylmorpholine; and inorganic basic compounds, such as potassium carbonate, sodium carbonate and sodium hydrogencarbonate. The above-mentioned basic compound may also function as an inert medium. The above-mentioned amine compound may also function as a basic compound or an inert medium.

Compound (1) of the present invention, which is obtained by the above-mentioned reactions, may or may not be isolated and purified from the reaction mixture. However, it is preferred that the compound be purified by known methods, such as column chromatography using silica gel or the like as a solid phase.

Compound (1) of the present invention can be provided in the form of an acid addition salt thereof. Examples of acid addition salts of compound (1) include salts thereof with inorganic acids, such as hydrochloric acid, sulfuric acid and phosphoric acid, and salts thereof with organic acids, such as acetic acid, propionic acid, p-toluenesulfonic acid, maleic acid, tartaric acid, citric acid, glycolic acid, gluconic acid, succinic acid and malic acid. Further, compound (1) can be provided also in the form of a metal salt thereof, such as a sodium salt or a potassium salt, depending on the type of R².

The above-mentioned salts of compound (1) can be produced by a known method for producing a salt from a free base. For example, the hydrochloride of compound (1) of the present invention can be prepared by adding a solution of hydrochloric acid in methanol to compound (1) in an amount of 1 equivalent or more per equivalent of compound (1) to form the hydrochloride of compound (1) in the form of a precipitate, and then collecting the precipitate. When the hydrochloride of compound (1) is hardly deposited as a precipitate, an appropriate solvent (e.g., diethyl ether) can be added thereto to deposit the hydrochloride as a precipitate.

In the present invention, compound (1), which has an asymmetric carbon atom, may be in an optically active form or in the form of a racemic modification thereof. Compound (1) which is in an optically active form can be isolated and collected by a conventional method. As examples of such a method, there can be mentioned a chromatographic resolution method; and a method in which an enantiomeric salt of compound (1) is formed and then, the salt is subjected to optical resolution by selective crystallization or subjected to enzymatic hydrolysis using a stereoselective esterase, so that the desired compound in an optically active form can be obtained. Alternatively, the desired compound in optically active form can be obtained by using an optically active starting material.

The thus obtained, novel 2,3-dihydrobenzofuran derivative or a salt thereof of the present invention acts on a 5-HT1A receptor and, therefore, can be formulated into a pharmaceutical composition useful for treatment of a serotonergic neuron-related disease. In the present invention, a serotonergic neuron-related disease means a neuron-related disease which has correlations with serotonin. Specific examples of serotonergic neuron-related disease include anxiety, depression, eating disorder, high blood pressure, emeses (including emeses induced by motion sickness, space sickness, dizziness and drug, etc.), and the like.

For preparation of such a pharmaceutical composition, compound (1) or a salt thereof can be combined with a pharmaceutically acceptable carrier and may be administered to a patient orally or parenterally by a conventional method.

The pharmaceutical composition of the present invention can be administered to a patient in the form of a solution for injection, intravenous drip, tablet, pill, powder, granule or capsule. For the preparation of such a pharmaceutical composition, various types of pharmaceutically acceptable carriers can be employed, depending on the form of the pharmaceutical composition.

For example, when compound (1) of the present invention is formulated into a medicine for oral administration (such as a tablet, granule, capsule or the like), there can be employed excipients, such as starch, lactose, refined sugar, mannitol, carboxymethyl cellulose, corn starch and inorganic salts; disintegrating agents, such as methylcellulose, sodium salt of carboxymethyl cellulose, hydroxypropyl cellulose, crystalline cellulose, ethylcellulose, polyvinyl pyrrolidone and macrogol; surfactants, such as sodium laurylsulfate, soybean lecithin, sucrose esters of fatty acids and polysorbate 80; lubricants, such as talc, wax, hydrated vegetable oils, sucrose esters of fatty acids, magnesium stearate and calcium stearate; fluidity promoting agent; sweetening and flavoring agents; and the like. The pharmaceutical composition of the present invention can be administered in the form of an emulsion, syrup or elixir.

When compound (1) of the present invention is formulated into a medicine for parenteral administration, a diluent, such as distilled water for injection, physiological saline, an aqueous solution of glucose, a vegetable oil for injection, propylene glycol or polyethylene glycol, can be used. In addition, if desired, other additives, such as a germicide, antiseptic, stabilizer, isotonicity agent and soothing agent, can be used.

A pharmaceutical composition of the present invention for treating a serotonergic neuron-related disease may be administered to a patient orally or parenterally. When the pharmaceutical composition is parenterally administered, it can be administered by way of an intramuscular injection or an intravenous injection, and it can also be administered endermically, transnasally or transvaginally.

The dose of the pharmaceutical composition of the present invention for treating a serotonergic neuron-related disease is varied depending on various factors, such as the manner of administration, age, weight, condition of the patient, etc. However, the dose may generally be about 0.001 to about 100 mg/kg per day for an adult in terms of the amount of compound (1).

Effect of the Invention

In order to demonstrate the pharmacological activities of compound (1) and a salt thereof of the present invention, tests were conducted with respect to compounds (1) synthesized in Examples described below.

The procedures and results of the tests are as follows.

1. Affinity for serotonin 1A receptor (1) Method (A) Preparation of rat hippocampal membrane fraction A male SD strain rat (7-week old; Charles River) was decapitated, and brain was taken out therefrom quickly. 50 mM Tris-HCl buffer (pH 7.4) was added to the brain under ice cooling to obtain a suspension. The resultant suspension was homogenized, and then subjected to centrifugation at 48000 g for 15 minutes, to thereby obtain a precipitate. The precipitate was resuspended in the same Tris-HCl buffer as used above. The resultant suspension was incubated at 30° C. for 20 minutes to decompose endogenous serotonin of the rat hippocampal membrane, followed by centrifugation at 48000 g for 15 minutes to thereby obtain a precipitate. The resultant precipitate was used as a rat hippocampal membrane fraction in the following procedures.

(B) Method for the evaluation of the binding ability of $^3$H-8-hydroxy-2-dipropylaminotetralin ($^3$H-8-OH-DPAT) to serotonin 1A receptor The rat hippocampal membrane fraction prepared in step (A) above (about 0.1 to 0.2 mg in terms of proteins) was reacted with 0.5 nM (final concentration) $^3$H-8-OH-DPAT (which is commercially available from DuPont-NEN Research Products, U.S.A.) and 0.01 mM (final concentration) pargyline (which is commercially available from Sigma Chemical Company, U.S.A.) at 30° C. for 30 minutes to effect a reaction. The resultant reaction mixture was subjected to suction filtration using a Whatman GF/C filter, to thereby terminate the reaction. The radioactivity of $^3$H-8-OH-DPAT adsorbed on the filter was determined using a liquid scintillation counter. The obtained value is regarded as a total amount (TB) of specifically binding $^3$H-8-OH-DPAT and non-specifically binding $^3$H-8-OH-DPAT. On the other hand, substantially the same procedure as mentioned above was repeated, except that 0.01 mM (final concentration) serotonin was added to the $^3$H-8-OH-DPAT and pargyline. The radioactivity of $^3$H-8-OH-DPAT adsorbed on the filter was determined in the same manner as mentioned above. The obtained value is regarded as the amount (NB) of non-specifically binding $^3$H-8-OH-DPAT.

Further, substantially the same procedure as mentioned above was repeated, except that, instead of serotonin, a test compound was used in a predetermined concentration. The radioactivity of $^3$H-8-OH-DPAT adsorbed on the filter was determined in the same manner as mentioned above. The obtained value is regarded as the amount (DTB) of binding $^3$H-8-OH-DPAT.

(C) Calculation of Ki value

The inhibition ratio of the test compound (at a certain concentration) against the binding of $^3$H-8-OH-DPAT (the inhibition ratio is hereinafter referred to simply as "binding inhibition ratio") was calculated according to the following formula:

$$\text{Binding inhibition ratio (\%)}=100-(DTB-NB)+(TB-NB)\times 100$$

With respect to each of the test compounds, the binding inhibition ratios at various concentrations (from a higher concentration to a lower concentration) were determined. The binding inhibition ratios were plotted, taking the logarithmic value of the concentration of test compound as the abscissa value, and the binding inhibition ratio as the ordinate value. Then, a curve was drawn by non-linear least square method. From the curve thus drawn, the IC$_{50}$ value (the concentration at which a test compound inhibits the binding of $^3$H-8-OH-DPAT to the serotonin 1A receptor by 50%) was determined with respect to each of the test compounds.

The Ki value was determined according to the following formula:

$$Ki=IC_{50}\div(1+[L]/Kd)$$

wherein:

[L] is the concentration (0.2 nM) of a radioactive ligand ($^3$H-8-OH-DPAT) used in the test;

Kd is the concentration (0.7174 nM) at which the radioactive ligand ($^3$H-8-OH-DPAT) exhibits the affinity for the serotonin 1A receptor; and IC$^{50}$ is the concentration of a test compound at which the test compound inhibits the binding of the radioactive ligand (3H-8-OH-DPAT) to the serotonin 1A receptor by 50%.

Each of the compounds (1) used in the above tests was tested in the form of a hydrochloride salt thereof.

(2) Results

The Ki values of the individual test compounds to the serotonin 1A receptor are shown in Table 1 below.

2. Animal testings (Activities against emesis)

(1) Method

The activities of individual compounds against emesis were examined using Suncus murinus. Suncus murinus is a small animal belonging to the Soricidae family. It has been known that suncus is likely to suffer from motion sickness and is susceptible to occurrence of emesis [see "Seitai-no-kagaku (Science of living body)", 42, 538 (1990)]. Suncus is likely to show symptoms like the symptoms of human motion sickness under the stimulus of simple acceleration, finally leading to the occurrence of emesis. It has been known that a drug such as cisplatin has an emesis-inducing activity.

In this test, test compounds were individually administered intraperitoneally to suncus. 30 minutes after the administration, acceleration-stimulus (amplitude: 4 cm; frequency; 1 Hz) was given to the suncus, and the suncus thus treated was observed as to whether emesis occurred or not.

(2) Results

The time for occurrence of emesis was measured with respect to each of the test compounds, and the results are shown in Table 2 below. From the results, it is concluded that compounds (1) of the present invention are useful for preventing and treating space sickness, dizziness, drug-induced emesis and the like.

3. Affinity for adrenaline α1 receptor (1) Method (A) Preparation of membrane fraction of rat adrenaline α1 receptor A male SD strain rat (7-week old; Charles River) was decapitated, and brain was taken out therefrom quickly. Cerebral cortex of the rat was separated and extracted at 50 mM under ice cooling. The extracted cerebral cortex was frozen at −80° C. for 24 hours or longer. This frozen system was gradually thawed under ice cooling and then, 50 mM Tris-HCl buffer (pH 7.4) was added to the brain under ice cooling to obtain a suspension. The resultant suspension was homogenized, and then subjected to centrifugation at 48000 g for 15 minutes, to thereby obtain a precipitate. The precipitate thus obtained was washed twice and resuspended in the same Tris-HCl buffer as used above. The resultant precipitate was used as a membrane fraction of rat adrenaline α1 receptor in the following procedures.

(B) Method for the evaluation of the binding ability of $^3$H-Prazosin to rat adrenaline α1 receptor The membrane fraction of rat adrenaline α1 receptor prepared in step (A) above was reacted with 0.2 nM (final concentration) $^3$H-Prazosin (which is commercially available from DuPont-NEN Research Products) and 0.005% (final concentration) ascorbic acid at 25° C. for 30 minutes to effect a reaction. The total volume amount of the reaction mixture was 1 ml. The resultant reaction mixture was subjected to suction filtration using a Whatman GF/C filter, and the filter was washed three times in 50 mM Tris-HCl buffer (pH 7.4, 4 ml), transferred to a vial and then, the radioactivity of Prazosin absorbed on the filter was determined using a liquid scintillation counter. The obtained value is regarded as a total amount (TB) of specifically binding $^3$H-Prazosin and non-specifically binding $^3$H-Prazosin. On the other hand, substantially the same procedure as mentioned above was repeated, except that 100 nM (final concentration) Prazosin was added to the $^3$H-Prazosin and ascorbic acid. The radioactivity of $^3$H-Prazosin adsorbed on the filter was determined in the same manner as mentioned above. The obtained value is regarded as the amount (NB) of non-specifically binding $^3$H-Prazosin.

Further, substantially the same procedure as mentioned above was repeated, except that, instead of Prazosin, a test compound was used in a predetermined concentration. The radioactivity of $^3$H-Prazosin adsorbed on the filter was determined in the same manner as mentioned above. The obtained value is regarded as the amount (DTB) of binding $^3$H-Prazosin.

(C) Calculation of Ki value

The inhibition ratio of the test compound (at a certain concentration) against the binding of $^3$H-Prazosin was calculated according to the following formula:

$$\text{Binding inhibition ratio } (\%)=100-(DTB-NB)\div(TB-NB)\times100$$

With respect to each of the test compounds, the binding inhibition ratios at various concentrations (from a higher concentration to a lower concentration) were determined. The binding inhibition ratios were plotted, taking the logarithmic value of the concentration of the test compound as the abscissa value, and the binding inhibition ratio as the ordinate value. Then, a curve was drawn by non-linear least square method. From the curve thus drawn, the IC$_{50}$ value (the concentration at which a test compound inhibits the binding of $^3$H-Prazosin to the adrenaline α1 receptor by 50%) was determined with respect to each of the test compounds.

The Ki value was determined according to the following formula:

$$Ki=IC_{50}\div(1+[L]/Kd)$$

wherein:

[L] is the concentration (0.2 nM) of a radioactive ligand ($^3$H-Prazosin) used in the test;

Kd is the concentration (0.133 nM) at which the radioactive ligand (3H-Prazosin) exhibits the affinity for the adrenaline α1 receptor; and IC$_{50}$ is the concentration of a test compound at which the test compound inhibits the binding of the radioactive ligand ($^3$H-Prazosin) to the adrenaline α1 receptor by 50%.

Each of the compounds (1) used in the above tests was tested in the form of a hydrochloride salt thereof.

(2) Results

The Ki values of the individual test compounds to the adrenaline α1 receptor are shown in Table 3 below.

4. Anti-depression activity (which was evaluated by forced swimming test using rats)

When a rat is put in a water tank, the rat struggles for its life to get out of the water (that is, the rat starts a "forced swimming"). If the rat finds that it is impossible for him to get out, the rat stops swimming and assumes an immobile state. It has been known that the administration of an antidepressant can cause a violent swimming motion in the rat for getting out of the water, with a result that the time spent in the immobile state is shortened. The shortening of the time in the immobile state of the rat in the forced swimming test by the administration of the antidepressant is well correlated to the clinical anti-depression effect. Accordingly, in developing antidepressants, the forced swimming test using a rat is the most reliable screening method. In the present test, male Wistar strain rats were used. Compounds obtained in Examples 1, 17 and 18 of the present invention (each in the form of a hydrochloride thereof) were, individually, orally administered to a rat. 30 minutes after the administration, the rat was put in a water tank and then, observed for 6 minutes. The time of the rat spent in the immobile state was measured.

As shown in Table 4 below, the compounds of the present invention, which were obtained in Examples 1, 17 and 18 (each in the form of a hydrochloride thereof; 30 mg/kg and 60 mg/kg), remarkably shortened the time spent in the immobile state. From these results, it is concluded that the compounds obtained in Examples 1, 17 and 18 are effective for preventing and treating depression.

5. Toxicity tests

Compounds (1) of the present invention exhibited low toxicity. For example, when a compound of Example 1 was intraperitoneally administered to mice (100 mg/kg), none of the mice died. The results indicate that compounds (1) of the present invention are highly safe.

From the above results, it will be understood that compounds (1) of the present invention and salts thereof have a strong affinity for a serotonin 1A receptor, and are useful for prevention and treatment of serotonergic neuron-related diseases, such as anxiety, depression, eating disorder, high blood pressure, emeses (including emeses induced by motion sickness, space sickness, dizziness, drug, etc.) and the like.

It has been confirmed that compounds (1) of the present invention have a strong affinity for a serotonin 1A receptor while exhibiting a weak affinity for an adrenaline α1 receptor, thus exhibiting selective activities.

BEST MODE FOR CARRYING OUT THE INVENTION

The present invention will be described in greater detail with reference to the following Reference Examples and Examples, which, however, should not be construed to be limiting the scope of the present invention. Substituents of the compounds obtained in the Reference Examples and Examples are shown in Table 5 below, and physical properties (i.e., NMR spectra and mass spectra) of those compounds are shown in Table 6 below.

REFERENCE EXAMPLE 1

Synthesis of 2-{N-(4-aminobutyl)-N-(tert-butoxycarbonyl)}aminomethyl-2,3-dihydrobenzo[b]furan Step A (Synthesis of 2-acetoxyallylbenzene)

1.3 ml (10 mmol) of 2-allylphenol was dissolved in 6.5 ml of pyridine, followed by cooling to 0° C. To the resultant solution were added 24 mg (0.2 mmol) of dimethylaminopyridine and 1.9 ml (20 mmol) of acetyl chloride. The resultant mixture was stirred at 0° C. for 2 hours to effect a reaction. To the resultant reaction mixture was added 50 ml of chloroform to obtain a mixture. The obtained mixture was successively washed with 50 ml of a saturated aqueous sodium hydrogencarbonate solution, 50 ml of water and 50 ml of saturated saline, to thereby form a chloroform layer containing the desired 2-acetoxyallylbenzene, followed by separation of the chloroform layer. The chloroform layer thus separated was dehydrated by means of a Whatman 1PS filter paper and then, concentrated in vacuo. The obtained residue was subjected to distillation in vacuo (78+ to 80° C./4 mmHg) to thereby obtain 1.64 g of 2-acetoxyallylbenzene as a transparent oily substance (yield: 93%).

Step B (Synthesis of 3-(2-acetoxyphenyl)-1,2-dibromopropane)

580 mg (3.0 mmol) of 2-acetoxyallylbenzene, which had been prepared in Step A, was dissolved in 5 ml of carbon tetrachloride, followed by cooling to 0° C. To the resultant solution was dropwise added 0.16 ml (3.0 mmol) of bromine and then, the resultant mixture was stirred at 0° C. for 2 hours to effect a reaction. To the resultant reaction mixture was added 20 ml of chloroform to obtain a mixture. The obtained mixture was successively washed with 20 ml of an aqueous sodium hydrogensulfite solution, 20 ml of water and 20 ml of saturated saline, to thereby form a chloroform layer containing the desired 3-(2-acetoxyphenyl)-1,2-dibromopropane, followed by separation of the chloroform layer. The chloroform layer thus separated was dehydrated by means of a Whatman 1PS filter paper and then, concentrated in vacuo to thereby obtain 0.93 g of 3-(2-acetoxyphenyl)-1,2-dibromopropane as a transparent oily substance (yield: 92%). This compound was used for the subsequent reaction without being further purified.

Step C (Synthesis of 2-bromomethyl-2,3-dihydrobenzo[b]furan)

340 mg (1.0 mmol) of 3-(2-acetoxyphenyl)-1,2-dibromopropane, which had been prepared in Step B, was dissolved in 3 ml of ethanol, followed by cooling to 0° C. To the resultant solution was dropwise added 1.2 ml (1.2 mmol) of a 1N solution of sodium ethoxide in ethanol and then, the resultant mixture was stirred at 0° C. for 2 hours to effect a reaction. To the resultant reaction mixture was added 20 ml of chloroform to obtain a mixture. The obtained mixture was successively washed with 20 ml of a 10% aqueous citric acid solution, 20 ml of water and 20 ml of saturated saline, to thereby form a chloroform layer containing the desired 2-bromomethyl-2,3-dihydrobenzo[b]furan, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with a mixed solvent of hexane-ethyl acetate (30:1), to thereby obtain 140 mg of 2-bromomethyl-2,3-dihydrobenzo[b]furan as a transparent oily substance (yield: 66%).

Step D (Synthesis of 2-{N-(4-hydroxybutyl)}aminomethyl-2,3-dihydrobenzo[b]furan)

430 mg (2.0 mmol) of 2-bromomethyl-2,3-dihydrobenzo[b]furan, which had been prepared in the same method as in Step C, was dissolved in 4 ml of acetonitrile. To the resultant solution were added 0.92 ml (10.0 mmol) of 4-amino-1-butanol and 550 mg (4.0 mmol) of potassium carbonate and then, the resultant mixture was stirred at 80° C. for 8 hours to effect a reaction. To the resultant reaction mixture was added 20 ml of chloroform to obtain a mixture. The obtained mixture was successively washed with 20 ml of a saturated aqueous sodium hydrogencarbonate solution, 20 ml of water and 20 ml of saturated saline, to thereby form a chloroform layer containing the desired 2-{N-(4-hydroxybutyl)}aminomethyl-2,3-dihydrobenzo[b]furan, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with a mixed solvent of chloroform-methanol-concentrated aqueous ammonia (10:1:0.1) to thereby obtain 300 mg of 2-{N-(4-hydroxybutyl)}aminomethyl-2,3-dihydrobenzo[b]furan as a light yellow oily substance (yield: 67%).

Step E (Synthesis of 2-{N-(tert-butoxycarbonyl)-N-(4-hydroxybutyl)}aminomethyl-2,3-dihydrobenzo[b]furan)

220 ml (1.0 mmol) of 2-{N-(4-hydroxybutyl)}aminomethyl-2,3-dihydrobenzo[b]furan, which had been prepared in Step D, was dissolved in 2 ml of methylene chloride, followed by cooling to 0° C. To the resultant solution were added 0.15 ml (1.1 mmol) of triethylamine and 240 mg (1.1 mmol) of a ditertiary butoxycarbonyl anhydride. The resultant mixture was stirred at room temperature for 2 hours to effect a reaction. To the resultant reaction mixture was added 20 ml of chloroform to obtain a mixture. The obtained mixture was successively washed with 20 ml of a saturated aqueous sodium hydrogencarbonate solution, 20 ml of water and 20 ml of saturated saline, to thereby form a chloroform layer containing the desired 2-{N-(tert-butoxycarbonyl)-N-(4-hydroxybutyl)}aminomethyl-2,3-dihydrobenzo[b]furan, followed by separation of the chloroform layer. The chloroform layer thus separated was dehydrated by means of a Whatman 1PS filter paper and then, concentrated in vacuo. The obtained residue was purified by silica gel column chromatography. That is, the residue was applied to a column of 10 g of silica gel (Art. 9385, manufactured and sold by E. Merck, Darmstadt, Germany) and eluted with chloroform to thereby obtain 306 mg of 2-{N-(tert-butoxycarbonyl)-N-(4-hydroxybutyl)}aminomethyl-2,3-dihydrobenzo[b]furan as a transparent oily substance (yield: 95%).

Step F (Synthesis of 2-[N-(tert-butoxycarbonyl)-N-{4-(4-methylphenylsulfonyloxy)butyl}]aminomethyl-2,3-dihydrobenzo[b]furan)

322 mg (1.00 mmol) of 2-{N-(tert-butoxycarbonyl)-N-(4-hydroxybutyl)}aminomethyl-2,3-dihydrobenzo[b]furan, which had been prepared in Step E, was dissolved in 4 ml of methylene chloride, followed by cooling to 0° C. To the resultant solution were added 0.56 ml (4.0 mmol) of triethylamine and 300 mg (1.58 mmol) of tosyl chloride. The resultant mixture was stirred at room temperature for 24 hours to effect a reaction. To the resultant reaction mixture was added 50 ml of chloroform to obtain a mixture. The obtained mixture was successively washed with 50 ml of water and 50 ml of saturated saline, to thereby form a chloroform layer containing the desired 2-[N-(tert-butoxycarbonyl)-N-{4-(4-methylphenylsulfonyloxy)butyl}]aminomethyl-2,3-dihydrobenzo[b]furan, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with hexane-ethyl acetate (5:1), to thereby obtain 459 mg of 2-[N-(tert-butoxycarbonyl)-N-{4-(4-methylphenylsulfonyloxy)butyl}]aminomethyl-2,3-dihydrobenzo[b]furan as a transparent oily substance (yield: 96%).

Step G (Synthesis of 2-{N-(4-azidobutyl)-N-(tert-butoxycarbonyl)}aminomethyl-2,3-dihydrobenzo[b]furan)

184 mg (0.39 mmol) of 2-[N-(tert-butoxycarbonyl)-N-{4-(4-methylphenylsulfonyloxy)butyl}]aminomethyl-2,3-dihydrobenzo[b]furan, which had been prepared in Step F, was dissolved in 1 ml N,N-dimethylformamide. To the resultant solution was added 100 mg (1.54 mmol) of sodium azide and then, the resultant mixture was stirred at 40° C. for 4 hours to effect a reaction. To the resultant reaction mixture was added 20 ml of chloroform to obtain a mixture. The obtained mixture was successively washed with 20 ml of water and 20 ml of saturated saline, to thereby form a chloroform layer containing the desired 2-{N-(4-azidobutyl)-N-(tert-butoxycarbonyl)}aminomethyl-2,3-dihydrobenzo[b]furan, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with hexane-ethyl acetate (20:1), to thereby obtain 120 mg of 2-{N-(4-azidobutyl)-N-(tert-butoxycarbonyl)}aminomethyl-2,3-dihydrobenzo[b]furan as a transparent oily substance (yield: 89%).

Step H (Synthesis of 2-{N-(4-aminobutyl)-N-(tert-butoxycarbonyl)}aminomethyl-2,3-dihydrobenzo[b]furan)

117 mg (0.34 mmol) of 2-{N-(4-azidobutyl)-N-(tert-butoxycarbonyl)}aminomethyl-2,3-dihydrobenzo[b]furan, which had been prepared in Step G, was dissolved in 2 ml of methanol. To the resultant solution was added 15 mg of 10% palladium-activated carbon and then, the resultant mixture was stirred at room temperature for 24 hours under the atmosphere of hydrogen to effect a reaction. The resultant reaction mixture was subjected to filtration through a Celite filter to filter off insoluble substances, which were then washed with a small amount of methanol, to thereby obtain a filtrate. The solvent of the filtrate was concentrated in vacuo to thereby obtain 108 mg of 2-{N-(4-aminobutyl)-N-(tert-butoxycarbonyl)}aminomethyl-2,3-dihydrobenzo[b]furan as a transparent oily substance (yield: 100%). This compound was used for the subsequent reactions for producing compounds which are mentioned in Examples 1 to 16 and 27, 28 without being further purified.

REFERENCE EXAMPLE 2

Synthesis of 2-{N-(2-aminoethyl)-N-benzyl}aminomethyl-2,3-dihydrobenzo[b]furan

Step A (Synthesis of 2-(N-benzyl)aminomethyl-2,3-dihydrobenzo[b]furan)

1.07 g (5.0 mmol) of 2-bromomethyl-2,3-dihydrobenzo[b]furan, which had been prepared in Step C of Reference Example 1, was dissolved in 11 ml of acetonitrile. To the resultant solution were added 1.64 ml (15.0 mmol) of benzylamine and 2.07 g (15.0 mmol) of potassium carbonate. The resultant mixture was stirred at 80° C. for 8 hours to effect a reaction. To the resultant reaction mixture was added 100 ml of chloroform to obtain a mixture. The obtained mixture was successively washed with 100 ml of water and 100 ml of saturated saline, to thereby form a chloroform layer containing the desired 2-(N-benzyl) aminomethyl-2,3-dihydrobenzo[b]furan, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 50 g of silica gel (Art. 9385, manufactured and sold by E. Merck, Darmstadt, Germany) and eluted with chloroform, to thereby obtain 873 mg of 2-(N-benzyl) aminomethyl-2,3-dihydrobenzo[b]furan as a yellow oily substance (yield: 73%).

Step B (Synthesis of 2-{N-benzyl-N-(2-phthalimidoethyl)}aminomethyl-2,3-dihydrobenzo[b]furan)

2.39 g (10.0 mmol) of 2-(N-benzyl)aminomethyl-2,3-dihydrobenzo[b]furan, which had been prepared in Step A, was dissolved in 24 ml of acetonitrile. To the resultant solution were added 5.08 g (20.0 mmol) of N-(2-bromoethyl)phthalimide and 2.76 g (20.0 mmol) of potassium carbonate and then, the resultant mixture was stirred at 80° C. for 8 hours to effect a reaction. To the resultant reaction mixture was added 100 ml of chloroform to obtain a mixture. The obtained mixture was successively washed with 100 ml of water and 100 ml of saturated saline, to thereby form a chloroform layer containing the desired 2-{N-benzyl-N-(2-phthalimidoethyl)}aminomethyl-2,3-dihydrobenzo[b]furan, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 50 g of silica gel (Art. 9385, manufactured and sold by E. Merck, Darmstadt, Germany) and eluted with a mixed solvent of hexane-ethyl acetate (20:1) to thereby obtain 3.08 g of 2-{N-benzyl-N-(2-phthalimidoethyl)}aminomethyl-2,3-dihydrobenzo[b]furan as a yellow oily substance (yield: 75%).

Step C (Synthesis of 2-{N-(2-aminoethyl)-N-benzyl}aminomethyl-2,3-dihydrobenzo[b]furan)

2.06 g (5.00 mmol) of 2-{N-benzyl-N-(2-phthalimidoethyl)}aminomethyl-2,3-dihydrobenzo[b]furan, which had been prepared in Step B, was dissolved in 20 ml of a mixed solvent of methylene chloride-ethanol (9:1). To the resultant solution was added 0.29 ml (6.00 mmol) of a 100% hydrazine hydrate at 0° C. and then, the resultant mixture was stirred at room temperature for 3 days to effect a reaction. To the resultant reaction mixture was added 50 ml of chloroform to obtain a mixture. The obtained mixture was successively washed with 50 ml of water and 50 ml of saturated saline, to thereby form a chloroform layer containing the desired 2-{N-(2-aminoethyl)-N-benzyl}aminomethyl-2,3-dihydrobenzo[b]furan, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 50 g of silica gel (Art. 9385, manufactured and sold by E. Merck, Darmstadt, Germany) and eluted with a mixed solvent of chloroform-methanol-concentrated aqueous ammonia (30:1:0.1), to thereby obtain 1.19 g of 2-{N-(2-aminoethyl)-N-benzyl}aminomethyl-2,3-dihydrobenzo[b]furan as a yellow oily substance (yield: 84%).

REFERENCE EXAMPLE 3

Synethsis of 2-{N-(3-aminopropyl)-N-benzyl}aminomethyl-2,3-dihydrobenzo[b]furan

Step A (Synthesis of 2-{N-benzyl-N-(3-phthalimidopropyl)}aminomethyl-2,3-dihydrobenzo[b]furan)

864 mg (3.60 mmol) of 2-(N-benzyl)aminomethyl-2,3-dihydrobenzo[b]furan, which had been prepared in Step A of Reference Example 2, was dissolved in 9 ml of acetonitrile. To the resultant solution were added 1.94 g (7.20 mmol) of N-(3-bromopropyl)phthalimide and 1.11 g (8.00 mmol) of potassium carbonate. The resultant mixture was stirred at 80° C. for 8 hours to effect a reaction. To the resultant reaction mixture was added 20 ml of chloroform to obtain a mixture. The obtained mixture was successively washed with 20 ml of water and 20 ml of saturated saline, to thereby form a chloroform layer containing the desired 2-{N-benzyl-N-(3-phthalimidopropyl)}aminomethyl-2,3-dihydrobenzo[b]furan, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 20 g of silica gel (Art. 9385, manufactured and sold by E. Merck, Darmstadt, Germany) and eluted with a mixed solvent of hexane-ethyl acetate (10:1), to thereby obtain 1.47 g of 2-{N-benzyl-N-(3-phthalimidopropyl)}-aminomethyl-2,3-dihydrobenzo[b]furan as a yellow oily substance (yield: 98%).

Step B (Synthesis of 2-{N-(3-aminopropyl)-N-benzyl}aminomethyl-2,3-dihydrobenzo[b]furan)

1.28 g (3.00 mmol) of 2-{N-benzyl-N-(3-phthalimidopropyl)}aminomethyl-2,3-dihydrobenzo[b]furan, which had been prepared in Step A, was dissolved in 20 ml of a mixed solvent of methylene chloride-ethanol (9:1). To the resultant solution was added 0.17 ml (3.60 mmol) of a 100% hydrazine hydrate at 0° C. and then, the resultant mixture was stirred at room temperature for 2 days to effect a reaction. To the resultant reaction mixture was added 50 ml of chloroform to obtain a mixture. The obtained mixture was successively washed with 50 ml of water and 50 ml of saturated saline, to thereby form a chloroform layer containing the desired 2-{N-(3-aminopropyl)-N-benzyl}aminomethyl-2,3-dihydrobenzo[b]furan, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 20 g of silica gel (Art. 9385, manufactured and sold by E. Merck, Darmstadt, Germany) and eluted with a mixed solvent of chloroform-methanol-concentrated aqueous ammonia (30:1:0.1) to thereby obtain 678 mg of 2-{N-(3-aminopropyl)-N-benzyl}aminomethyl-2,3-dihydrobenzo[b]furan as a yellow oily substance (yield: 76%).

EXAMPLE 1

Synthesis of 2-{N-(4-benzoylaminobutyl)}aminomethyl-2,3-dihydrobenzo[b]furan

Step A (Synthesis of 2-{N-(4-benzoylaminobutyl)-N-(tert-butoxycarbonyl)}aminomethyl-2,3-dihydrobenzo[b]furan)

128 mg (0.40 mmol) of 2-{N-(4-aminobutyl)-N-(tert-butoxycarbonyl)}aminomethyl-2,3-dihydrobenzo[b]furan, which had been prepared in Reference Example 1, was dissolved in 1.3 ml of methylene chloride, followed by cooling to 0° C. To the resultant solution were added 0.08 ml (0.6 mmol) of triethylamine and 0.06 ml (0.5 mmol) of benzoyl chloride. The resultant mixture was gradually heated from 0° C. and stirred at room temperature for 24 hours to effect a reaction. To the resultant reaction mixture was added 20 ml of chloroform to obtain a mixture. The obtained mixture was successively washed with 20 ml of a saturated aqueous sodium hydrogencarbonate solution, 20 ml of water and 20 ml of saturated saline, to thereby form a chloroform layer containing the desired 2-{N-(4-benzoylaminobutyl)-N-(tert-butoxycarbonyl)} aminomethyl-2,3-dihydrobenzo[b]furan, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with a mixed solvent of hexane-ethyl acetate (2:1), to thereby obtain 151 mg of 2-{N-(4-benzoylaminobutyl)-N-(tert-butoxycarbonyl)}aminomethyl-2,3-dihydrobenzo[b]furan as a transparent oily substance (yield: 89%).

Step B (Synthesis of 2-{N-(4-benzoylaminobutyl)} aminomethyl-2,3-dihydrobenzo[b]furan)

151 mg (0.36 mmol) of 2-{N-(4-benzoylaminobutyl)-N-(tert-butoxycarbonyl)}aminomethyl-2,3-dihydrobenzo[b]furan, which had been prepared in Step A, was cooled to 0° C. To the cooled compound was added 1.5 ml of trifluoroacetic acid and then, the resultant mixture was stirred at 0° C. for 2 hours to effect a reaction. The resultant reaction mixture was concentrated in vacuo to thereby obtain a residue, which was then cooled to 0° C. again and then, 12 ml of diethyl ether was added thereto. The resultant mixture was stirred for 2 hours to thereby form a precipitate. The resultant mixture was subjected to filtration to filter off the precipitate, which was then washed with a small amount of diethyl ether and dissolved in 20 ml of chloroform. The obtained mixture was successively washed with 20 ml of a saturated aqueous sodium hydrogencarbonate solution, 20 ml of water and 20 ml of saturated saline, to thereby form a chloroform layer containing the desired 2-{N-(4-benzoylaminobutyl)}aminomethyl-2,3-dihydrobenzo[b]furan, followed by separation of the chloroform layer. The chloroform layer thus separated was dehydrated by means of a Whatman 1PS filter paper and then, concentrated in vacuo to thereby obtain 89 mg of 2-{N-(4-benzoylaminobutyl)}aminomethyl-2,3-dihydrobenzo[b]furan as a light yellow oily substance (yield: 76%).

EXAMPLE 2
Synthesis of 2-{N-(4-benzenesulfonamidobutyl)} aminomethyl-2,3-dihydrobenzo[b]furan Step A (Synthesis of 2-{N-(4-benzenesulfonamidobutyl)-N-(tert-butoxycarbonyl)}aminomethyl-2,3-dihydrobenzo[b]furan)

128 mg (0.40 mmol) of 2-{N-(4-aminobutyl)-N-(tert-butoxycarbonyl)}aminomethyl-2,3-dihydrobenzo[b]furan, which had been prepared in Reference Example 1, was dissolved in 1.3 ml of methylene chloride, followed by cooling to 0° C. To the resultant solution were added 0.08 ml (0.6 mmol) of triethylamine and 0.06 ml (0.5 mmol) of benzenesulfonyl chloride. The resultant mixture was stirred at 0° C. for 1 hour to effect a reaction. To the resultant reaction mixture was added 20 ml of chloroform to obtain a mixture. The obtained mixture was successively washed with 20 ml of a saturated aqueous sodium hydrogencarbonate solution, 20 ml of water and 20 ml of saturated saline, to thereby form a chloroform layer containing the desired 2-{N-(4-benzenesulfonamidobutyl)-N-(tert-butoxycarbonyl)}aminomethyl-2,3-dihydrobenzo[b]furan, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with a mixed solvent of hexane-ethyl acetate (2:1), to thereby obtain 167 mg of 2-{N-(4-benzenesulfonamidobutyl)-N-(tert-butoxy- carbonyl)} aminomethyl-2,3-dihydrobenzo[b]furan as a light yellow oily substance (yield: 91%).

Step B (Synthesis of 2-{N-(4-benzenesulfonamidobutyl)} aminomethyl-2,3-dihydrobenzo[b]furan)

156 mg (0.34 mmol) of 2-{N-(4-benzenesulfonamidobutyl)-N- (tert-butoxycarbonyl)} aminomethyl-2,3-dihydrobenzo[b]furan, which had been prepared in Step A, was cooled to 0° C. To the cooled compound was added 1.6 ml of trifluoroacetic acid and then, the resultant mixture was stirred at 0° C. for 2 hours to effect a reaction. The resultant reaction mixture was concentrated in vacuo to thereby obtain a residue which was then cooled to 0° C. again and then, 12 ml of diethyl ether was added thereto and the resultant mixture was stirred for 2 hours to thereby form a precipitate. The resultant mixture was subjected to filtration to filter off the precipitate, which was then washed with a small amount of diethyl ether and dissolved in 20 ml of chloroform. The obtained mixture was successively washed with 20 ml of a saturated aqueous sodium hydrogencarbonate solution, 20 ml of water and 20 ml of saturated saline, to thereby form a chloroform layer containing the desired 2-{N-(4-benzenesulfonamidobutyl)} aminomethyl-2,3-dihydrobenzo[b]furan, followed by separation of the chloroform layer. The chloroform layer thus separated was dehydrated by means of a Whatman 1PS filter paper and then, concentrated in vacuo to thereby obtain 109 mg of 2-{N-(4-benzenesulfonamidobutyl)}aminomethyl-2,3-dihydrobenzo[b]furan as a light yellow oily substance (yield: 89%).

EXAMPLE 3
Synthesis of 2,3-dihydro-2-[N-{4-(2-methylbenzoylamino)butyl}]aminomethylbenzo[b]furan Step A (Synthesis of 2,3-dihydro-2-[N-{4-(2-methylbenzoylamino)butyl}-N-(tert-butoxycarbonyl)] aminomethylbenzo[b]furan)

160 mg (0.50 mmol) of 2-{N-(4-aminobutyl)-N-(tert-butoxycarbonyl)}aminomethyl-2,3-dihydrobenzo[b]furan, which had been prepared in Reference Example 1, was dissolved in 1.6 ml of methylene chloride, followed by cooling to 0° C. To the resultant solution were added 0.14 ml (1.0 mmol) of triethylamine and 0.08 ml (0.6 mmol) of o-toluoyl chloride (manufactured and sold by Tokyo Kasei Co., Japan). The resultant mixture was stirred at 0° C. for 2 hours to effect a reaction. To the resultant reaction mixture was added 20 ml of chloroform to obtain a mixture. The obtained mixture was successively washed with 20 ml of a saturated aqueous sodium hydrogencarbonate solution, 20 ml of water and 20 ml of saturated saline, to thereby form a chloroform layer containing the desired 2,3-dihydro-2-[N-{4-(2-methylbenzoylamino)butyl}-N-(tert-butoxycarbonyl)]aminomethylbenzo[b]furan, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with a mixed solvent of hexane-ethyl acetate (2:1), to thereby obtain 192 mg of 2,3-dihydro-2-[N-{4-(2-methylbenzoylamino)butyl}-N-(tert-butoxycarbonyl)]aminomethylbenzo[b]furan as a transparent oily substance (yield: 88%).

Step B (Synthesis of .2,3-dihydro-2-[N-{4-(2-methylbenzoylamino)butyl}]aminomethylbenzo[b]furan)

190 mg (0.43 mmol) of 2,3-dihydro-2-[N-{4-(2-methylbenzoylamino)butyl}-N-(tert-butoxycarbonyl)] aminomethylbenzo[b]furan, which had been prepared in Step A, was cooled to 0° C. To the cooled compound was added 1.9 ml of trifluoroacetic acid and then, the resultant mixture was stirred at 0° C. for 2 hours to effect a reaction. The resultant reaction mixture was concentrated in vacuo to thereby obtain a residue, which was then dissolved in 20 ml of chloroform. The resultant solution was successively washed with 20 ml of a saturated aqueous sodium hydrogencarbonate solution, 20 ml of water and 20 ml of saturated saline, to thereby form a chloroform layer containing the desired 2,3-dihydro-2-[N-{4-(2-methylbenzoylamino) butyl}]aminomethylbenzo[b]furan, followed by separation of the chloroform layer. The chloroform layer thus separated was dehydrated by means of a Whatman 1PS filter paper and then, concentrated in vacuo to thereby obtain 141 mg of 2,3-dihydro-2-[N-{4-(2-methylbenzoylamino)butyl}] aminomethylbenzo[b]furan as a light yellow oily substance (yield: 97%).

EXAMPLE 4
Synthesis of 2,3-dihydro-2-[N-{4-(3-methylbenzoylamino) butyl}]aminomethylbenzo[b]furan Step A (Synthesis of 2,3-dihydro-2-[N-{4-(3-methylbenzoylamino)butyl}-N-(tert-butoxycarbonyl)] aminomethylbenzo[b]furan)

160 mg (0.50 mmol) of 2-{N-(4-aminobutyl)-N-(tert-butoxycarbonyl)}aminomethyl-2,3-dihydrobenzo[b]furan, which had been prepared in Reference Example 1, was dissolved in 1.6 ml of methylene chloride, followed by cooling to 0° C. To the resultant solution were added 0.14 ml (1.0 mmol) of triethylamine and 0.08 ml (0.6 mmol) of m-toluoyl chloride (manufactured and sold by Tokyo Kasei Co., Japan). The resultant mixture was stirred at 0° C. for 2 hours to effect a reaction. To the resultant reaction mixture was added 20 ml of chloroform to obtain a mixture. The obtained mixture was successively washed with 20 ml of a saturated aqueous sodium hydrogencarbonate solution, 20 ml of water and 20 ml of saturated saline, to thereby form a chloroform layer containing the desired 2,3-dihydro-2-[N-{4-(3-methylbenzoylamino)butyl}-N-(tert-butoxycarbonyl) ]aminomethylbenzo[b]furan, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with a mixed solvent of hexane-ethyl acetate (2:1), to thereby obtain 174 mg of 2,3-dihydro-2-[N-{4-(3-methylbenzoylamino)butyl}-N-(tert-butoxycarbonyl)]aminomethylbenzo[b]furan as a light yellow oily substance (yield: 79%).

Step B (Synthesis of 2,3-dihydro-2-[N-{4-(3-methylbenzoylamino)butyl}]aminomethylbenzo[b]furan)

170 mg (0.39 mmol) of 2,3-dihydro-2-[N-{4-(3-methylbenzoylamino)butyl}-N-(tert-butoxycarbonyl)] aminomethylbenzo[b]furan, which had been prepared in Step A, was cooled to 0° C. To the cooled compound was added 1.7 ml of trifluoroacetic acid and then, the resultant mixture was stirred at 0° C. for 1.5 hours to effect a reaction. The resultant reaction mixture was concentrated in vacuo to thereby obtain a residue, which was then dissolved in 20 ml of chloroform. The resultant solution was successively washed with 20 ml of a saturated aqueous sodium hydrogencarbonate solution, 20 ml of water and 20 ml of saturated saline, to thereby form a chloroform layer containing the desired 2,3-dihydro-2-[N-{4-(3-methylbenzoylamino) butyl}]aminomethylbenzo[b]furan, followed by separation of the chloroform layer. The chloroform layer thus separated was dehydrated by means of a Whatman 1PS filter paper and then, concentrated in vacuo to thereby obtain 134 mg of 2,3-dihydro-2-[N-{4-(3-methylbenzoylamino)butyl}] aminomethylbenzo[b]furan as a light yellow oily substance (yield: 100%).

EXAMPLE 5
Synthesis of 2,3-dihydro-2-[N-{4-(4-methylbenzoylamino) butyl}]aminomethylbenzo[b]furan Step A (Synthesis of 2,3-dihydro-2-[N-{4-(4-methylbenzoylamino)butyl}-N-(tert-butoxycarbonyl)] aminomethylbenzo[b]furan)

160 mg (0.50 mmol) of 2-{N-(4-aminobutyl)-N-(tert-butoxycarbonyl)}aminomethyl-2,3-dihydrobenzo[b]furan, which had been prepared in Reference Example 1, was dissolved in 1.6 ml of methylene chloride, followed by cooling to 0° C. To the resultant solution were added 0.14 ml (1.0 mmol) of triethylamine and 0.08 ml (0.6 mmol) of p-toluoyl chloride (manufactured and sold by Tokyo Kasei Kogyo Co., Ltd., Japan). The resultant mixture was stirred at 0° C. for 1.5 hours to effect a reaction. To the resultant reaction mixture was added 20 ml of chloroform to obtain a mixture. The obtained mixture was successively washed with 20 ml of a saturated aqueous sodium hydrogencarbonate solution, 20 ml of water and 20 ml of saturated saline, to thereby form a chloroform layer containing the desired 2,3-dihydro-2-[N-{4-(4-methylbenzoylamino)butyl}-N-(tert-butoxycarbonyl)]aminomethylbenzo[b]furan, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with a mixed solvent of hexane-ethyl acetate (2:1), to thereby obtain 192 mg of 2,3-dihydro-2-[N-{4-(4-methylbenzoylamino)butyl}-N-(tert-butoxycarbonyl)] aminomethylbenzo[b]furan as a light yellow oily substance (yield: 87%).

Step B (Synthesis of 2,3-dihydro-2-[N-{4-(4-methylbenzoylamino)butyl}]aminomethylbenzo[b]furan)

190 mg (0.43 mmol) of 2,3-dihydro-2-[N-{4-(4-methylbenzoylamino)butyl}-N-(tert-butoxycarbonyl)] aminomethylbenzo[b]furan, which had been prepared in Step A, was cooled to 0° C. To the cooled compound was added 1.9 ml of trifluoroacetic acid and then, the resultant mixture was stirred at 0° C. for 1.5 hours to effect a reaction. The resultant reaction mixture was concentrated in vacuo to thereby obtain a residue, which was then dissolved in 20 ml of chloroform. The resultant solution was successively washed with 20 ml of a saturated aqueous sodium hydrogencarbonate solution, 20 ml of water and 20 ml of saturated saline, to thereby form a chloroform layer containing the desired 2,3-dihydro-2-[N-{4-(4-methylbenzoylamino) butyl}]aminomethylbenzo[b]furan, followed by separation of the chloroform layer. The chloroform layer thus separated was dehydrated by means of a Whatman 1PS filter paper and then, concentrated in vacuo to thereby obtain 154 mg of 2,3-dihydro-2-[N-{4-(4-methylbenzoylamino)butyl}]aminomethylbenzo[b]furan as a light yellow oily substance (yield: 100%).

EXAMPLE 6
Synthesis of 2,3-dihydro-2-[N-{4-(2-methoxybenzoylamino)butyl}]aminomethylbenzo[b]furan Step A (Synthesis of 2,3-dihydro-2-[N-{4-(2-methoxybenzoylamino)butyl}-N-(tert-butoxycarbonyl)]aminomethylbenzo[b]furan)

160 mg (0.50 mmol) of 2-{N-(4-aminobutyl)-N-(tert-butoxycarbonyl)}aminomethyl-2,3-dihydrobenzo[b]furan, which had been prepared in Reference Example 1, was dissolved in 1.6 ml of methylene chloride, followed by cooling to 0° C. To the resultant solution were added 0.14 ml (1.0 mmol) of triethylamine and 0.09 ml (0.6 mmol) of o-anisoyl chloride (manufactured and sold by Tokyo Kasei Kogyo Co., Ltd., Japan). The resultant mixture was stirred at 0° C. for 2 hours to effect a reaction. To the resultant reaction mixture was added 20 ml of chloroform to obtain a mixture. The obtained mixture was successively washed with 20 ml of a saturated aqueous sodium hydrogencarbonate solution, 20 ml of water and 20 ml of saturated saline, to thereby form a chloroform layer containing the desired 2,3-dihydro-2-[N-{4-(2-methoxybenzoylamino)butyl}-N-(tert-butoxycarbonyl)]aminomethylbenzo[b]furan, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with a mixed solvent of hexane-ethyl acetate (2:1), to thereby obtain 215 mg of 2,3-dihydro-2-[N-{4-(2-methoxybenzoylamino)butyl}-N-(tert-butoxycarbonyl)]aminomethylbenzo[b]furan as a light yellow oily substance (yield: 94%).

Step B (Synthesis of 2,3-dihydro-2-[N-{4-(2-methoxybenzoylamino)butyl}]aminomethylbenzo[b]furan)

200 mg (0.44 mmol) of 2,3-dihydro-2-[N-{4-(2-methoxybenzoylamino)butyl}-N-(tert-butoxycarbonyl)]aminomethylbenzo[b]furan, which had been prepared in Step A, was cooled to 0° C. To the cooled compound was added 2.0 ml of trifluoroacetic acid and then, the resultant mixture was stirred at 0° C. for 1.5 hours to effect a reaction. The resultant reaction mixture was concentrated in vacuo to thereby obtain a residue, which was then dissolved in 20 ml of chloroform. The resultant solution was successively washed with 20 ml of a saturated aqueous sodium hydrogencarbonate solution, 20 ml of water and 20 ml of saturated saline, to thereby form a chloroform layer containing the desired 2,3-dihydro-2-[N-{4-(2-methoxybenzoylamino)butyl}]aminomethylbenzo[b]furan, followed by separation of the chloroform layer. The chloroform layer thus separated was dehydrated by means of a Whatman 1PS filter paper and then, concentrated in vacuo to thereby obtain 164 mg of 2,3-dihydro-2-[N-{4-(2-methoxybenzoylamino)butyl}]aminomethylbenzo[b]furan as a light yellow oily substance (yield: 100%).

EXAMPLE 7
Synthesis of 2,3-dihydro-2-[N-{4-(3-methoxybenzoylamino)butyl}]aminomethylbenzo[b]furan Step A (Synthesis of 2,3-dihydro-2-[N-{4-(3-methoxybenzoylamino)butyl}-N-(tert-butoxycarbonyl)]aminomethylbenzo[b]furan)

160 mg (0.50 mmol) of 2-{N-(4-aminobutyl)-N-(tert-butoxycarbonyl)}aminomethyl-2,3-dihydrobenzo[b]furan, which had been prepared in Reference Example 1, was dissolved in 1.6 ml of methylene chloride, followed by cooling to 0° C. To the resultant solution were added 0.14 ml (1.0 mmol) of triethylamine and 0.08 ml (0.6 mmol) of m-anisoyl chloride (manufactured and sold by Aldrich Chemical Co., Inc., U.S.A.). The resultant mixture was stirred at 0° C. for 1.5 hours to effect a reaction. To the resultant reaction mixture was added 20 ml of chloroform to obtain a mixture. The obtained mixture was successively washed with 20 ml of a saturated aqueous sodium hydrogencarbonate solution, 20 ml of water and 20 ml of saturated saline, to thereby form a chloroform layer containing the desired 2,3-dihydro-2-[N-{4-(3-methoxybenzoylamino)butyl}-N-(tert-butoxycarbonyl)]aminomethylbenzo[b]furan, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with a mixed solvent of hexane-ethyl acetate (2:1), to thereby obtain 196 mg of 2,3-dihydro-2-[N-{4-(3-methoxybenzoylamino)butyl}-N-(tert-butoxycarbonyl)]aminomethylbenzo[b]furan as a light yellow oily substance (yield: 86%).

Step B (Synthesis of 2,3-dihydro-2-[N-{4-(3-methoxybenzoylamino)butyl}]aminomethylbenzo[b]furan)

190 mg (0.42 mmol) of 2,3-dihydro-2-[N-{4-(3-methoxybenzoylamino)butyl}-N-(tert-butoxycarbonyl)]aminomethylbenzo[b]furan, which had been prepared in Step A, was cooled to 0° C. To the cooled compound was added 1.9 ml of trifluoroacetic acid and then, the resultant mixture was stirred at 0° C. for 1.5 hours to effect a reaction. The resultant reaction mixture was concentrated in vacuo to thereby obtain a residue, which was then dissolved in 20 ml of chloroform. The resultant solution was successively washed with 20 ml of a saturated aqueous sodium hydrogencarbonate solution, 20 ml of water and 20 ml of saturated saline, to thereby form a chloroform layer containing the desired 2,3-dihydro-2-[N-{4-(3-methoxybenzoylamino)butyl}]aminomethylbenzo[b]furan, followed by separation of the chloroform layer. The chloroform layer thus separated was dehydrated by means of a Whatman 1PS filter paper and then, concentrated in vacuo to thereby obtain 153 mg of 2,3-dihydro-2-[N-{4-(3-methoxybenzoylamino)butyl}]aminomethylbenzo[b]furan as a light yellow oily substance (yield: 100%).

EXAMPLE 8
Synthesis of 2,3-dihydro-2-[N-{4-(4-methoxybenzoylamino)butyl}]aminomethylbenzo[b]furan Step A (Synthesis of 2,3-dihydro-2-[N-{4-(4-methoxybenzoylamino)butyl}-N-(tert-butoxycarbonyl)]aminomethylbenzo[b]furan)

160 mg (0.50 mmol) of 2-{N-(4-aminobutyl)-N-(tert-butoxycarbonyl)}aminomethyl-2,3-dihydrobenzo[b]furan, which had been prepared in Reference Example 1, was dissolved in 1.6 ml of methylene chloride, followed by cooling to 0° C. To the resultant solution were added 0.14 ml (1.0 mmol) of triethylamine and 102 mg (0.6 mmol) of p-anisoyl chloride (manufactured and sold by Aldrich Chemical Co., Inc., U.S.A.) The resultant mixture was stirred at 0° C. for 2 hours to effect a reaction. To the resultant reaction mixture was added 20 ml of chloroform to obtain a mixture. The obtained mixture was successively washed with 20 ml of a saturated aqueous sodium hydrogencarbonate solution, 20 ml of water and 20 ml of saturated saline, to thereby form a chloroform layer containing the desired 2,3-dihydro-2-[N-{4-(4-methoxybenzoylamino) butyl}-N-(tert-butoxycarbonyl)]aminomethylbenzo[b] furan, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with a mixed solvent of hexane-ethyl acetate (1:1), to thereby obtain 203 mg of 2,3dihydro-2-[N-{4-(4-methoxybenzoylamino)butyl}-N-(tert-butoxycarbonyl)]aminomethylbenzo[b]furan as a light yellow oily substance (yield: 89%).

Step B (Synthesis of 2,3-dihydro-2-[N-{4-(4-methoxybenzoylamino)butyl}]aminomethylbenzo[b]furan)

190 mg (0.42 mmol) of 2,3-dihydro-2-[N-{4-(4-methoxybenzoylamino)butyl}-N-(tert-butoxycarbonyl)] aminomethylbenzo[b]furan, which had been prepared in Step A, was cooled to 0° C. To the cooled compound was added 1.9 ml of trifluoroacetic acid and then, the resultant mixture was stirred at 0° C. for 1.5 hours to effect a reaction. The resultant reaction mixture was concentrated in vacuo to thereby obtain a residue, which was then dissolved in 20 ml of chloroform. The resultant solution was successively washed with 20 ml of a saturated aqueous sodium hydrogencarbonate solution, 20 ml of water and 20 ml of saturated saline, to thereby form a chloroform layer containing the desired 2,3-dihydro-2-[N-{4-(4-methoxybenzoylamino) butyl}]aminomethylbenzo[b]furan, followed by separation of the chloroform layer. The chloroform layer thus separated was dehydrated by means of a Whatman 1PS filter paper and then, concentrated in vacuo to thereby obtain 148 mg of 2,3-dihydro-2-[N-{4-(4-methoxybenzoylamino)butyl}] aminomethylbenzo[b]furan as a light yellow oily substance (yield: 100%).

EXAMPLE 9

Synthesis of 2,3-dihydro-2-[N-{4-(2-fluorobenzoylamino) butyl}]aminomethylbenzo[b]furan Step A (Synthesis of 2,3-dihydro-2-[N-{4-(2-fluorobenzoylamino)butyl}-N-(tert-butoxycarbonyl)] aminomethylbenzo[b]furan)

160 mg (0.50 mmol) of 2-{N-(4-aminobutyl)-N-(tert-butoxycarbonyl)}aminomethyl-2,3-dihydrobenzo[b]furan, which had been prepared in Reference Example 1, was dissolved in 1.6 ml of methylene chloride, followed by cooling to 0° C. To the resultant solution were added 0.14 ml (1.0 mmol) of triethylamine and 0.07 ml (0.6 mmol) of o-fluorobenzoyl chloride (manufactured and sold by Tokyo Kasei Kogyo Co., Ltd., Japan). The resultant mixture was stirred at 0° C. for 1.5 hours to effect a reaction. To the resultant reaction mixture was added 20 ml of chloroform to obtain a mixture. The obtained mixture was successively washed with 20 ml of a saturated aqueous sodium hydrogencarbonate solution, 20 ml of water and 20 ml of saturated saline, to thereby form a chloroform layer containing the desired 2,3-dihydro-2-[N-{4-(2-fluorobenzoylamino) butyl}-N-(tert-butoxycarbonyl)]aminomethylbenzo[b] furan, followed by separation of the chloroform layer. The chloroform layer thus separated was dehydrated by means of a Whatman 1PS filter paper and then, concentrated in vacuo to thereby obtain 210 mg of 2,3-dihydro-2-[N-{4-(2-fluorobenzoylamino)butyl}-N-(tert-butoxycarbonyl)] aminomethylbenzo[b]furan as a light yellow oily sub-stance (yield: 95%).

Step B (Synthesis of 2,3-dihydro-2-[N-{4-(2-fluorobenzoylamino)butyl}]aminomethylbenzo[b]furan)

200 mg (0.45 mmol) of 2,3-dihydro-2-[N-{4-(2-fluorobenzoylamino)butyl}-N-(tert-butoxycarbonyl)] aminomethylbenzo[b]furan, which had been prepared in Step A, was cooled to 0° C. To the cooled compound was added 2.0 ml of trifluoroacetic acid and then, the resultant mixture was stirred at 0° C. for 2 hours to effect a reaction. The resultant reaction mixture was concentrated in vacuo to thereby obtain a residue, which was then dissolved in 20 ml of chloroform. The resultant solution was successively washed with 20 ml of a saturated aqueous sodium hydrogencarbonate solution, 20 ml of water and 20 ml of saturated saline, to thereby form a chloroform layer containing the desired 2,3-dihydro-2-[N-{4-(2-fluorobenzoylamino) butyl}]aminomethylbenzo[b]furan, followed by separation of the chloroform layer. The chloroform layer thus separated was dehydrated by means of a Whatman 1PS filter paper and then, concentrated in vacuo to thereby obtain 150 mg of 2,3-dihydro-2-[N-{4-(2-fluorobenzoylamino)butyl}] aminomethylbenzo[b]furan as a light yellow oily substance (yield: 97%).

EXAMPLE 10

Synthesis of 2,3-dihydro-2-[N-{4-(3-fluorobenzoylamino) butyl}]aminomethylbenzo[b]furan Step A (Synthesis of 2,3-dihydro-2-[N-{4-(3-fluorobenzoylamino)butyl}-N-(tert-butoxycarbonyl)] aminomethylbenzo[b]furan)

160 mg (0.50 mmol) of 2-{N-(4-aminobutyl)-N-(tert-butoxycarbonyl)}aminomethyl-2,3-dihydrobenzo[b]furan, which had been prepared in Reference Example 1, was dissolved in 1.6 ml of methylene chloride, followed by cooling to 0° C. To the resultant solution were added 0.14 ml (1.0 mmol) of triethylamine and 0.07 ml (0.6 mmol) of m-fluorobenzoyl chloride (manufactured and sold by Tokyo Kasei Kogyo Co., Ltd., Japan). The resultant mixture was stirred at 0° C. for 2 hours to effect a reaction. To the resultant reaction mixture was added 20 ml of chloroform to obtain a mixture. The obtained mixture was successively washed with 20 ml of a saturated aqueous sodium hydrogencarbonate solution, 20 ml of water and 20 ml of saturated saline, to thereby form a chloroform layer containing the desired 2,3-dihydro-2-[N-{4-(3-fluorobenzoylamino) butyl}-N-(tert-butoxycarbonyl)]aminomethylbenzo[b] furan, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with a mixed solvent of hexane-ethyl acetate (2:1), to thereby obtain 209 mg of 2,3-dihydro-2-[N-{4-(3-fluorobenzoylamino)butyl}-N-(tert-butoxycarbonyl)]aminomethylbenzo[b]furan as a light yellow oily substance (yield: 94%).

Step B (Synthesis of 2,3-dihydro-2-[N-{4-(3-fluorobenzoylamino)butyl}]aminomethylbenzo[b]furan)

190 mg (0.43 mmol) of 2,3-dihydro-2-[N-{4-(3-fluorobenzoylamino)butyl}-N-(tert-butoxycarbonyl)] aminomethylbenzo[b]furan, which had been prepared in Step A, was cooled to 0° C. To the cooled compound was added 1.9 ml of trifluoroacetic acid and then, the resultant mixture was stirred at 0° C. for 2 hours to effect a reaction. The resultant reaction mixture was concentrated in vacuo to thereby obtain a residue, which was then dissolved in 20 ml of chloroform. The resultant solution was successively washed with 20 ml of a saturated aqueous sodium hydrogencarbonate solution, 20 ml of water and 20 ml of saturated saline, to thereby form a chloroform layer containing the desired 2,3-dihydro-2-[N-{4-(3-fluorobenzoylamino) butyl}]aminomethylbenzo[b]furan, followed by separation of the chloroform layer. The chloroform layer thus separated was dehydrated by means of a Whatman 1PS filter paper and then, concentrated in vacuo to thereby obtain 153 mg of 2,3-dihydro-2-[N-{4-(3-fluorobenzoylamino)butyl}] aminomethylbenzo[b]furan as a light yellow oily substance (yield: 100%).

EXAMPLE 11

Synthesis of 2,3-dihydro-2-[N-{4-(4-fluorobenzoylamino) butyl}]aminomethylbenzo[b]furan Step A (Synthesis of 2,3-dihydro-2-[N-{4-(4-fluorobenzoylamino)butyl}-N-(tert-butoxycarbonyl)] aminomethylbenzo[b]furan)

160 mg (0.50 mmol) of 2-{N-(4-aminobutyl)-N-(tert-butoxycarbonyl)}aminomethyl-2,3-dihydrobenzo[b]furan, which had been prepared in Reference Example 1, was dissolved in 1.6 ml of methylene chloride, followed by cooling to 0° C. To the resultant solution were added 0.14 ml (1.0 mmol) of triethylamine and 0.07 ml (0.6 mmol) of p-fluorobenzoyl chloride (manufactured and sold by Tokyo Kasei Kogyo Co., Ltd., Japan). The resultant mixture was stirred at 0° C. for 2 hours to effect a reaction. To the resultant reaction mixture was added 20 ml of chloroform to obtain a mixture. The obtained mixture was successively washed with 20 ml of a saturated aqueous sodium hydrogencarbonate solution, 20 ml of water and 20 ml of saturated saline, to thereby form a chloroform layer containing the desired 2,3-dihydro-2-[N-{4-(4-fluorobenzoylamino) butyl}-N-(tert-butoxycarbonyl)]aminomethylbenzo[b] furan, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with a mixed solvent of hexane-ethyl acetate (2:1), to thereby obtain 187 mg of 2,3-dihydro-2-[N-{4-(4-fluorobenzoylamino)butyl}-N-(tert-butoxycarbonyl)]aminomethylbenzo[b]furan as a light yellow oily substance (yield: 84%).

Step B (Synthesis of 2,3-dihydro-2-[N-{4-(4-fluorobenzoylamino)butyl}]aminomethylbenzo[b]furan)

180 mg (0.41 mmol) of 2,3-dihydro-2-[N-{4-(4-fluorobenzoylamino)butyl}-N-(tert-butoxycarbonyl)] aminomethylbenzo[b]furan, which had been prepared in Step A, was cooled to 0° C. To the cooled compound was added 1.8 ml of trifluoroacetic acid and then, the resultant mixture was stirred at 0° C. for 2 hours to effect a reaction. The resultant reaction mixture was concentrated in vacuo to thereby obtain a residue, which was then dissolved in 20 ml of chloroform. The resultant solution was successively washed with 20 ml of a saturated aqueous sodium hydrogencarbonate solution, 20 ml of water and 20 ml of saturated saline, to thereby form a chloroform layer containing the desired 2,3-dihydro-2-[N-{4-(4-fluorobenzoylamino) butyl}]aminomethylbenzo[b]furan, followed by separation of the chloroform layer. The chloroform layer thus separated was dehydrated by means of a Whatman 1PS filter paper and then, concentrated in vacuo to thereby obtain 136 mg of 2,3-dihydro-2-[N-{4-(4-fluorobenzoylamino)butyl}] aminomethylbenzo[b]furan as a light yellow oily substance (yield: 97%).

EXAMPLE 12

Synthesis of 2,3-dihydro-2-[N-{4-(2-trifluoromethylbenzoylamino)butyl}]aminomethylbenzo[b] furan Step A (Synthesis of 2,3-dihydro-2-[N-{4-(2-trifluoromethylbenzoylamino)butyl}-N-(tert-butoxycarbonyl)]aminomethylbenzo[b]furan)

160 mg (0.50 mmol) of 2-{N-(4-aminobutyl)-N-(tert-butoxycarbonyl)}aminomethyl-2,3-dihydrobenzo[b]furan, which had been prepared in Reference Example 1, was dissolved in 1.6 ml of methylene chloride, followed by cooling to 0° C. To the resultant solution were added 0.14 ml (1.0 mmol) of triethylamine and 0.09 ml (0.6 mmol) of o-trifluoromethylbenzoyl chloride (manufactured and sold by Tokyo Kasei Kogyo Co., Ltd., Japan). The resultant mixture was stirred at 0° C. for 2 hours to effect a reaction. To the resultant reaction mixture was added 20 ml of chloroform to obtain a mixture. The obtained mixture was successively washed with 20 ml of a saturated aqueous sodium hydrogencarbonate solution, 20 ml of water and 20 ml of saturated saline, to thereby form a chloroform layer containing the desired 2,3-dihydro-2-[N-{4-(2-trifluoromethylbenzoylamino)butyl}-N-(tert-butoxycarbonyl)]aminomethylbenzo[b]furan, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with a mixed solvent of hexane-ethyl acetate (1:1), to thereby obtain 213 mg of 2,3-dihydro-2-[N-{4-(2-trifluoromethylbenzoylamino)butyl}-N-(tert-butoxycarbonyl)]aminomethylbenzo[b]furan as a light yellow oily substance (yield: 87%).

Step B (Synthesis of 2,3-dihydro-2-[N-{4-(2-trifluoromethylbenzoylamino)butyl}]aminomethylbenzo[b] furan)

210 mg (0.43 mmol) of 2,3-dihydro-2-[N-{4-(2-trifluoromethylbenzoylamino)butyl}-N-(tert-butoxycarbonyl)]aminomethylbenzo[b]furan, which had been prepared in Step A, was cooled to 0° C. To the cooled compound was added 2.0 ml of trifluoroacetic acid and then, the resultant mixture was stirred at 0° C. for 2 hours to effect a reaction. The resultant reaction mixture was concentrated in vacuo to thereby obtain a residue, which was then dissolved in 20 ml of chloroform. The resultant solution was successively washed with 20 ml of a saturated aqueous sodium hydrogencarbonate solution, 20 ml of water and 20 ml of saturated saline, to thereby form a chloroform layer containing the desired 2,3-dihydro-2-[N-{4-(2-trifluoromethylbenzoylamino)butyl}]aminomethylbenzo[b] furan, followed by separation of the chloroform layer. The chloroform layer thus separated was dehydrated by means of a Whatman 1PS filter paper and then, concentrated in vacuo to thereby obtain 166 mg of 2,3-dihydro-2-[N-{4-(2-trifluoromethylbenzoylamino)butyl}]aminomethylbenzo[b] furan as a light yellow oily substance (yield: 99%).

EXAMPLE 13

Synthesis of 2,3-dihydro-2-[N-{4-(3-trifluoromethylbenzoylamino)butyl}]aminomethylbenzo[b] furan Step A (Synthesis of 2,3-dihydro-2-[N-{4-(3-trifluoromethylbenzoylamino)butyl}-N-(tert-butoxycarbonyl)]aminomethylbenzo[b]furan)

160 mg (0.50 mmol) of 2-{N-(4-aminobutyl)-N-(tert-butoxycarbonyl)}aminomethyl-2,3-dihydrobenzo[b]furan, which had been prepared in Reference Example 1, was dissolved in 1.6 ml of methylene chloride, followed by cooling to 0° C. To the resultant solution were added 0.14 ml (1.0 mmol) of triethylamine and 0.09 ml (0.6 mmol) of m-trifluoromethylbenzoyl chloride (manufactured and sold by Tokyo Kasei Kogyo Co., Ltd., Japan). The resultant mixture was stirred at 0° C. for 2 hours to effect a reaction. To the resultant reaction mixture was added 20 ml of chloroform to obtain a mixture. The obtained mixture was successively washed with 20 ml of a saturated aqueous sodium hydrogencarbonate solution, 20 ml of water and 20 ml of saturated saline, to thereby form a chloroform layer containing the desired 2,3-dihydro-2-[N-{4-(3-trifluoromethylbenzoylamino)butyl}-N-(tert-butoxycarbonyl)]aminomethylbenzo[b]furan, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with a mixed solvent of hexane-ethyl acetate (2:1), to thereby obtain 205 mg of 2,3-dihydro-2-[N-{4-(3-trifluoromethylbenzoylamino)butyl}-N-(tert-butoxycarbonyl)]aminomethylbenzo[b]furan as a light yellow oily substance (yield: 83%).

Step B (Synthesis of 2,3-dihydro-2-[N-{4-(3-trifluoromethylbenzoylamino)butyl}]aminomethylbenzo[b]furan)

198 mg (0.40 mmol) of 2,3-dihydro-2-[N-{4-(3-trifluoromethylbenzoylamino)butyl}-N-(tert-butoxycarbonyl)]aminomethylbenzo[b]furan, which had been prepared in Step A, was cooled to 0° C. To the cooled compound was added 2.0 ml of trifluoroacetic acid and then, the resultant mixture was stirred at 0° C. for 2 hours to effect a reaction. The resultant reaction mixture was concentrated in vacuo to thereby obtain a residue, which was then dissolved in 20 ml of chloroform. The resultant solution was successively washed with 20 ml of a saturated aqueous sodium hydrogencarbonate solution, 20 ml of water and 20 ml of saturated saline, to thereby form a chloroform layer containing the desired 2,3-dihydro-2-[N-{4-(3-trifluoromethylbenzoylamino)butyl}]aminomethylbenzo[b]furan, followed by separation of the chloroform layer. The chloroform layer thus separated was dehydrated by means of a Whatman 1PS filter paper and then, concentrated in vacuo to thereby obtain 158 mg of 2,3-dihydro-2-[N-{4-(3-trifluoromethylbenzoylamino)butyl}]aminomethylbenzo[b]furan as a light yellow oily substance (yield: 100%).

EXAMPLE 14

Synthesis of 2,3-dihydro-2-[N-{4-(4-trifluoromethylbenzoylamino)butyl}]aminomethylbenzo[b]furan Step A (Synthesis of 2,3-dihydro-2-[N-{4-(4-trifluoromethylbenzoylamino)butyl}-N-(tert-butoxycarbonyl)]aminomethylbenzo[b]furan)

160 mg (0.50 mmol) of 2-{N-(4-aminobutyl)-N-(tert-butoxycarbonyl)}aminomethyl-2,3-dihydrobenzo[b]furan, which had been prepared in Reference Example 1, was dissolved in 1.6 ml of methylene chloride, followed by cooling to 0° C. To the resultant solution were added 0.14 ml (1.0 mmol) of triethylamine and 0.09 ml (0.6 mmol) of p-trifluoromethylbenzoyl chloride (manufactured and sold by Tokyo Kasei Kogyo Co., Ltd., Japan). The resultant mixture was stirred at 0° C. for 2 hours to effect a reaction. To the resultant reaction mixture was added 20 ml of chloroform to obtain a mixture. The obtained mixture was successively washed with 20 ml of a saturated aqueous sodium hydrogencarbonate solution, 20 ml of water and 20 ml of saturated saline, to thereby form a chloroform layer containing the desired 2,3-dihydro-2-[N-{4-(4-trifluoromethylbenzoylamino)butyl}-N-(tert-butoxycarbonyl)]aminomethylbenzo[b]furan, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with a mixed solvent of hexane-ethyl acetate (2:1), to thereby obtain 205 mg of 2,3-dihydro-2-[N-{4-(4-trifluoromethylbenzoylamino)butyl}-N-(tert-butoxycarbonyl)]aminomethylbenzo[b]furan as a light yellow oily substance (yield: 83%).

Step B (Synthesis of 2,3-dihydro-2-[N-{4-(4-trifluoromethylbenzoylamino)butyl}]aminomethylbenzo[b]furan)

200 mg (0.41 mmol) of 2,3-dihydro-2-[N-{4-(4-trifluoromethylbenzoylamino)butyl}-N-(tert-butoxycarbonyl)]aminomethylbenzo[b]furan, which had been prepared in Step A, was cooled to 0° C. To the cooled compound was added 2.0 ml of trifluoroacetic acid and then, the resultant mixture was stirred at 0° C. for 2 hours to effect a reaction. The resultant reaction mixture was concentrated in vacuo to thereby obtain a residue, which was then dissolved in 20 ml of chloroform. The resultant solution was successively washed with 20 ml of a saturated aqueous sodium hydrogencarbonate solution, 20 ml of water and 20 ml of saturated saline, to thereby form a chloroform layer containing the desired 2,3-dihydro-2-[N-{4-(4-trifluoromethylbenzoylamino)butyl}]aminomethylbenzo[b]furan, followed by separation of the chloroform layer. The chloroform layer thus separated was dehydrated by means of a Whatman 1PS filter paper and then, concentrated in vacuo to thereby obtain 154 mg of 2,3-dihydro-2-[N-{4-(4-trifluoromethylbenzoylamino)butyl}]aminomethylbenzo[b]furan as a light yellow oily substance (yield: 96%).

EXAMPLE 15

Synthesis of 2,3-dihydro-2-[N-{4-(3-nitrobenzoylamino)butyl}]aminomethylbenzo[b]furan Step A (Synthesis of 2,3-dihydro-2-[N-{4-(3-nitrobenzoylamino)butyl}-N-(tert-butoxycarbonyl)]aminomethylbenzo[b]furan)

160 mg (0.50 mmol) of 2-{N-(4-aminobutyl)-N-(tert-butoxycarbonyl)}aminomethyl-2,3-dihydrobenzo[b]furan, which had been prepared in Reference Example 1, was dissolved in 1.6 ml of methylene chloride, followed by cooling to 0° C. To the resultant solution were added 0.14 ml (1.0 mmol) of triethylamine and 111 mg (0.6 mmol) of m-nitrobenzoyl chloride (manufactured and sold by Tokyo Kasei Kogyo Co., Ltd., Japan). The resultant mixture was stirred at 0° C. for 2 hours to effect a reaction. To the resultant reaction mixture was added 20 ml of chloroform to obtain a mixture. The obtained mixture was successively washed with 20 ml of a saturated aqueous sodium hydrogencarbonate solution, 20 ml of water and 20 ml of saturated saline, to thereby form a chloroform layer containing the desired 2,3-dihydro-2-[N-{4-(3-nitrobenzoylamino)butyl}-N-(tert-butoxycarbonyl)]aminomethylbenzo[b]furan, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with a mixed solvent of hexane-ethyl acetate (2:1), to thereby obtain 200 mg of 2,3-dihydro-2-[N-{4-(3-nitrobenzoylamino)butyl}-N-(tert-butoxycarbonyl)] aminomethylbenzo[b]furan as a light yellow oily substance (yield: 85%).

Step B (Synthesis of 2,3-dihydro-2-[N-{4-(3-nitrobenzoylamino)butyl}]aminomethylbenzo[b]furan)

200 mg (0.43 mmol) of 2,3-dihydro-2-[N-{4-(3-nitrobenzoylamino)butyl}-N-(tert-butoxycarbonyl)] aminomethylbenzo[b]furan), which had been prepared in Step A, was cooled to 0° C. To the cooled compound was added 2.0 ml of trifluoroacetic acid and then, the resultant mixture was stirred at 0° C. for 2 hours to effect a reaction. The resultant reaction mixture was concentrated in vacuo to thereby obtain a residue, which was then dissolved in 20 ml of chloroform. The resultant solution was successively washed with 20 ml of a saturated aqueous sodium hydrogencarbonate solution, 20 ml of water and 20 ml of saturated saline, to thereby form a chloroform layer containing the desired 2,3-dihydro-2-[N-{4-(3-nitrobenzoylamino)butyl}] aminomethylbenzo[b]furan, followed by separation of the chloroform layer. The chloroform layer thus separated was dehydrated by means of a Whatman 1PS filter paper and then, concentrated in vacuo to thereby obtain 141 mg of 2,3-dihydro-2-[N-{4-(3-nitrobenzoylamino)butyl}] aminomethylbenzo[b]furan as a brown solid substance (yield: 90%).

EXAMPLE 16

Synthesis of 2,3-dihydro-2-[N-{4-(3-cyanobenzoylamino) butyl}]aminomethylbenzo[b]furan Step A (Synthesis of 2,3-dihydro-2-[N-{4-(3-cyanobenzoylamino)butyl}-N-(tert-butoxycarbonyl)] aminomethylbenzo[b]furan)

160 mg (0.50 mmol) of 2-{N-(4-aminobutyl)-N-(tert-butoxycarbonyl)}aminomethyl-2,3-dihydrobenzo[b]furan, which had been prepared in Reference Example 1, was dissolved in 1.6 ml of methylene chloride, followed by cooling to 0° C. To the resultant solution were added 0.14 ml (1.0 mmol) of triethylamine and 99 mg (0.6 mmol) of m-cyanobenzoyl chloride (manufactured and sold by Aldrich Chemical Co., Inc., U.S.A.). The resultant mixture was stirred at 0° C. for 2 hours to effect a reaction. To the resultant reaction mixture was added 20 ml of chloroform to obtain a mixture. The obtained mixture was successively washed with 20 ml of a saturated aqueous sodium hydrogencarbonate solution, 20 ml of water and 20 ml of saturated saline, to thereby form a chloroform layer containing the desired 2,3-dihydro-2-[N-{4-(3-cyanobenzoylamino) butyl}-N-(tert-butoxycarbonyl)]aminomethylbenzo[b] furan, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with a mixed solvent of hexane-ethyl acetate (2:1), to thereby obtain 199 mg of 2,3-dihydro-2-[N-{4-(3-cyanobenzoylamino)butyl}-N-(tert-butoxycarbonyl)]aminomethylbenzo[b]furan as a light yellow oily substance (yield: 88%).

Step B (Synthesis of 2,3-dihydro-2-[N-{4-(3-cyanobenzoylamino)butyl}]aminomethylbenzo[b]furan)

190 mg (0.42 mmol) of 2,3-dihydro-2-[N-{4-(3-cyanobenzoylamino)butyl}-N-(tert-butoxycarbonyl)] aminomethylbenzo[b]furan, which had been prepared in Step A, was cooled to 0° C. To the cooled compound was added 2.0 ml of trifluoroacetic acid and then, the resultant mixture was stirred at 0° C. for 2 hours to effect a reaction. The resultant reaction mixture was concentrated in vacuo to thereby obtain a residue, which was then dissolved in 20 ml of chloroform. The resultant solution was successively washed with 20 ml of a saturated aqueous sodium hydrogencarbonate solution, 20 ml of water and 20 ml of saturated saline, to thereby form a chloroform layer containing the desired 2,3-dihydro-2-[N-{4-(3-cyanobenzoylamino) butyl}]aminomethylbenzo[b]furan, followed by separation of the chloroform layer. The chloroform layer thus separated was dehydrated by means of a Whatman 1PS filter paper and then, concentrated in vacuo to thereby obtain 153 mg of 2,3-dihydro-2-[N-{4-(3-cyanobenzoylamino)butyl}] aminomethylbenzo[b]furan as a light yellow oily substance (yield: 100%).

EXAMPLE 17

Synthesis of the hydrochloride of (+)-2-{N-(4-benzoylamino)butyl}aminomethyl-2,3-dihydrobenzo[b] furan 44.2 g (136 mmol) of 2-{N-(4-benzoylaminobutyl)} aminomethyl-2,3-dihydrobenzo[b]furan, which had been prepared in Example 1, was dissolved in 910 ml of methanol. To the resultant solution was added 47.1 g (136 mmol) of (R)-(−)-N-(3,5-dinitrobenzoyl)-α-phenylglycine (manufactured and sold by Tokyo Kasei Kogyo Co., Ltd., Japan). The resultant mixture was allowed to stand still at room temperature for 6 hours to thereby deposit crystals. The crystals were collected by filtration, followed by drying in vacuo. The crystals were recrystallized twice from methanol to thereby obtain 22.2 g of crystals. The obtained crystals were dissolved in 70 ml of a 0.5N aqueous sodium hydroxide solution, followed by extraction twice with 100 ml of chloroform, to thereby form a chloroform layer containing (+)-2-{N-(4-benzoylaminobutyl)}aminomethyl-2,3-dihydrobenzo[b]furan, followed by separation of the chloroform layer. The chloroform layer thus separated was successively washed with 100 ml of water and 100 ml of saturated saline and then, dehydrated by means of a Whatman 1PS filter paper and then, concentrated in vacuo to thereby obtain a residue. The obtained residue was dissolved in a 2.7N solution of hydrochloric acid in methanol and then, concentrated in vacuo to thereby deposit crystals. The crystals were collected by filtration and dried in vacuo to obtain 10.9 g of the hydrochloride of (+)-2-{N-(4-benzoylaminobutyl)}aminomethyl-2,3-dihydrobenzo[b] furan as white crystals.

Optical purity: 98.0% ee as measured using Chiral cell OD (column size: 0.46×25 cm) manufactured by Osaka Soda Co., Ltd., Japan elution solvent: hexane-ethanol=90:10 (including 0.1% triethylamine), elution speed: 0.6 ml/m and detection wavelength: 270 nm $[α]_D$ 58.4 (C=0.5 methanol)

EXAMPLE 18

Synthesis of the hydrochloride of (−)-2-{N-(4-benzoylaminobutyl)}aminomethyl-2,3-dihydrobenzo[b] furan All mother liquors, which had been used for crystallization and recrystallization in Example 17, were collected and then, concentrated in vacuo. The resultant mixture was dissolved in 120 ml of a 1.0N aqueous sodium hydroxide solution, followed by extraction twice with 100 ml of chloroform, to thereby form a chloroform layer containing (−)-2-{N-(4-benzoylamino)butyl}aminomethyl-2,3-dihydrobenzo[b]furan, followed by separation of the chloroform layer. The chloroform layer thus separated was successively washed with 100 ml of water and 100 ml of saturated saline and then, dehydrated by means of a Whatman 1PS filter paper and then, concentrated in vacuo to thereby obtain a light yellow oily substance. The obtained substance was dissolved in 1.04 liter of methanol. To the resultant solution was added 35.6 g (103 mmol) of (S)-(+)-N-(3,5-dinitrobenzoyl)-α-phenylglycine (manufactured and sold by Aldrich Chemical Co., Inc., U.S.A.). The resultant reaction mixture was allowed to stand still at room temperature for 5 hours to thereby deposit crystals. The crystals were collected by filtration, and dried in vacuo. The crystals were recrystallized once from methanol to obtain 22.5 g of crystals. The obtained crystals were dissolved in 70 ml of a 0.5N aqueous sodium hydroxide solution, followed by extraction twice with 100 ml of chloroform, to thereby form a chloroform layer, followed by separation of the chloroform layer. The chloroform layer thus separated was successively washed with 100 ml of water and 100 ml of saturated saline and then, dehydrated by means of a Whatman 1PS filter paper and then, concentrated in vacuo to thereby obtain a residue. The obtained residue was dissolved in a 2.0N solution of hydrochloric acid in methanol and then, concentrated in vacuo to thereby deposit crystals. The crystals were collected by filtration, and dried in vacuo to obtain 11.2 g of the hydrochloride of (−)-2-{N-(4-benzoylamino)butyl}aminomethyl-2,3-dihydrobenzo[b]furan as white crystals.

Optical purity: 98.0% ee as measured using Chiral cell OD (column size: 0.46×25 cm) manufactured by Osaka Soda Co., Ltd., Japan elution solvent: hexane-ethanol=90:10 (including 0.1% triethylamine), elution speed: 0.6 ml/m and detection wavelength: 270 nm $[+]_D$ −61.6 (C=0.5 methanol)

EXAMPLE 19

Synthesis of 2-{N-(2-benzoylaminoethyl)}aminomethyl-2,3-dihydrobenzo[b]furan

Step A (Synthesis of 2-{N-(2-benzoylaminoethyl)-N-benzyl}aminomethyl-2,3-dihydrobenzo[b]furan)

141 mg (0.50 mmol) of 2-{N-(2-aminoethyl)-N-benzyl}aminomethyl-2,3-dihydrobenzo[b]furan, which had been prepared in Reference Example 2, was dissolved in 2.0 ml of methylene chloride, followed by cooling to 0° C. To the resultant solution were added 0.14 ml (1.00 mmol) of triethylamine and 0.07 ml (0.6 mmol) of benzoyl chloride. The resultant mixture was stirred at 0° C. for 2 hours to effect a reaction. To the resultant reaction mixture was added 20 ml of chloroform to obtain a mixture. The obtained mixture was successively washed with 20 ml of a saturated aqueous sodium hydrogencarbonate solution, 20 ml of water and 20 ml of saturated saline, to thereby form a chloroform layer containing the desired 2-{N-(2-benzoylaminoethyl)-N-benzyl}aminomethyl-2,3-dihydrobenzo[b]furan, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with a mixed solvent of hexane-ethyl acetate (2:1), to thereby obtain 190 mg of 2-{N-(2-benzoylaminoethyl)-N-benzyl}aminomethyl-2,3-dihydrobenzo[b]furan as a light yellow oily substance (yield: 98%).

Step B (Synthesis of 2-{N-(2-benzoylaminoethyl)}aminomethyl-2,3-dihydrobenzo[b]furan)

179 mg (0.46 mmol) of 2-{N-(2-benzoylaminoethyl)-N-benzyl}aminometyl-2,3-dihydrobenzo[b]furan, which had been prepared in Step A, was dissolved in 2.0 ml of methylene chloride, followed by cooling to 0° C. To the resultant solution was added 0.82 ml (1.38 mmol) of a solution of carbobenzoxy chloride in toluene (manufactured by Tokyo Kasei Kogyo Co., Ltd., Japan) and then, the resultant mixture was stirred at 40° C. for 6 hours to effect a reaction. To the resultant reaction mixture was added 20 ml of chloroform to obtain a mixture. The obtained mixture was successively washed with 20 ml of a saturated aqueous sodium hydrogencarbonate solution, 20 ml of water and 20 ml of saturated saline, to thereby form a chloroform layer, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with a mixed solvent of hexane-ethyl acetate (2:1), to thereby obtain 183 mg of 2-{N-(2-benzoylaminoethyl)-N-carbobenzoxy}aminomethyl-2,3-dihydrobenzo[b]furan. 180 mg (0.42 mmol) of the obtained compound was dissolved in 0.5 ml of acetic acid. To the resultant solution was added 0.05 ml of anisole, followed by cooling to 0° C., and then, 0.92 ml of a solution of 30% hydrobromic acid in acetic acid was added thereto. The resultant mixture was stirred at room temperature for 1 hour to effect a reaction. To the resultant reaction mixture was added 20 ml of ether to deposit a precipitate. The precipitate was obtained by filtration. The obtained precipitate was dissolved in 20 ml of chloroform and then, the resultant solution was successively washed with 20 ml of a saturated aqueous sodium hydrogencarbonate solution, 20 ml of water and 20 ml of saturated saline, to thereby form a chloroform layer containing the desired 2-{N-(2-benzoylaminoethyl)}aminomethyl-2,3-dihydrobenzo[b]furan, followed by separation of the chloroform layer. The chloroform layer thus separated was dehydrated by means of a Whatman 1PS filter paper and then, concentrated in vacuo to thereby obtain 129 mg of 2-{N-(2-benzoylaminoethyl)}aminomethyl-2,3-dihydrobenzo[b]furan as a transparent oily substance (yield: 95%).

EXAMPLE 20

Synthesis of 2-[N-{2-(3-methylbenzoylamino)ethyl}]aminomethyl-2,3-dihydrobenzo[b]furan Step A (Synthesis of 2-[N-benzyl-N-{2-(3-methylbenzoylamino)ethyl{]aminomethyl-2,3-dihydrobenzo[b]furan)

141 mg (0.50 mmol) of 2-(N-(2-aminoethyl)-N-benzyl}aminomethyl-2,3-dihydrobenzo[b]furan, which had been prepared in Reference Example 2, was dissolved in 2.0 ml of methylene chloride, followed by cooling to 0° C. To the resultant solution were added 0.14 ml (1.00 mmol) of triethylamine and 0.079 ml (0.60 mmol) of m-toluoyl chloride. The resultant mixture was stirred at 0° C. for 2 hours to effect a reaction. To the resultant reaction mixture was added 20 ml of chloroform to obtain a mixture. The obtained mixture was successively washed with 20 ml of a saturated aqueous sodium hydrogencarbonate solution, 20 ml of water and 20 ml of saturated saline, to thereby form a chloroform layer containing 2-[N-benzyl-N-{2-(3-methylbenzoylamino)ethyl}]aminomethyl-2,3-dihydrobenzo[b]furan, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with a mixed solvent of hexane-ethyl acetate (10:1), to thereby obtain 195 mg of 2-[N-benzyl-N-{2-(3-methylbenzoylamino)ethyl}] aminomethyl-2,3-dihydrobenzo[b]furan as a light yellow oily substance (yield: 97%).

Step B (Synthesis of 2-[N-{2-(3-methylbenzoylamino) ethyl}]aminomethyl-2,3-dihydrobenzo[b]furan) 195 mg (0.49 mmol) of 2-[N-benzyl-N-{2-(3-methylbenzoylamino) ethyl}]aminomethyl-2,3-dihydrobenzo[b]furan, which had been prepared in Step A, was dissolved in 2.0 ml of methylene chloride, followed by cooling to 0° C. To the resultant solution was added 0.87 ml (1.46 mmol) of a solution of carbobenzoxy chloride in toluene (manufactured and sold by Tokyo Kasei Kogyo Co., Ltd., Japan) and then, the resultant mixture was stirred at 40° C. for 6 hours to effect a reaction. To the resultant reaction mixture was added 20 ml of chloroform to obtain a mixture. The obtained mixture was successively washed with 20 ml of a saturated aqueous sodium hydrogencarbonate solution, 20 ml of water and 20 ml of saturated saline, to thereby form a chloroform layer, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with a mixed solvent of hexane-ethyl acetate (5:1), to thereby obtain 194 mg of 2-[N-{2-(3-methylbenzoylamino)ethyl}-N-carbobenzoxy] aminomethyl-2,3-dihydrobenzo[b]furan. 200 mg (0.45 mmol) of the obtained compound was dissolved in 0.8 ml of acetic acid. To the resultant solution was added 0.08 ml of anisole, followed by cooling to 0° C., and then, 1.48 ml of a solution of 30% hydrobromic acid in acetic acid was added thereto. The resultant mixture was stirred at room temperature for 1 hour to effect a reaction. To the resultant reaction mixture was added 20 ml of ether to deposit a precipitate. The precipitate was collected by filtration. The obtained precipitate was dissolved in 20 ml of chloroform and then, the obtained mixture was successively washed with 20 ml of a saturated aqueous sodium hydrogencarbonate solution, 20 ml of water and 20 ml of saturated saline, to thereby form a chloroform layer containing the desired 2-[N-{2-(3-methylbenzoylamino)ethyl}]aminomethyl-2,3-dihydrobenzo[b]furan, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with a mixed solvent of chloroform-methanol (10:1) to thereby obtain 122 mg of 2-[N-{2-(3-methylbenzoylamino)ethyl}] aminomethyl-2,3-dihydrobenzo[b]furan as a light yellow oily substance (yield: 78%).

EXAMPLE 21

Synthesis of 2-[N-{2-(4-fluorobenzoyl)aminoethyl}] aminomethyl-2,3-dihydrobenzo[b]furan Step A (Synthesis of 2-[N-benzyl-N-{2-(4-fluorobenzoylamino)ethyl}]aminomethyl-2,3-dihydrobenzo[b]furan)

141 mg (0.50 mmol) of 2-{N-(2-aminoethyl)-N-benzyl}aminomethyl-2,3-dihydrobenzo[b]furan, which had been prepared in Reference Example 2, was dissolved in 2.0 ml of methylene chloride, followed by cooling to 0° C. To the resultant solution were added 0.14 ml (1.00 mmol) of triethylamine and 0.07 ml (0.60 mmol) of 4-fluorobenzoyl chloride. The resultant mixture was stirred at 0° C. for 2 hours to effect a reaction. To the resultant reaction mixture was added 20 ml of chloroform to obtain a mixture. The obtained mixture was successively washed with 20 ml of a saturated aqueous sodium hydrogencarbonate solution, 20 ml of water and 20 ml of saturated saline, to thereby form a chloroform layer containing the desired 2-[N-benzyl-N-{2-(4-fluorobenzoylamino)ethyl}]aminomethyl-2,3-dihydrobenzo[b]furan, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with a mixed solvent of hexane-ethyl acetate (10:1), to thereby obtain 189 mg of 2-[N-benzyl-N-{2-(4-fluorobenzoylamino)ethyl}] aminomethyl-2,3-dihydrobenzo[b]furan as a light yellow oily substance (yield: 93%).

Step B (Synthesis of 2-[N-{2-(4-fluorobenzoylamino) ethyl}]aminomethyl-2,3-dihydrobenzo[b]furan)

180 mg (0.45 mmol) of 2-[N-benzyl-N-{2-(4-fluorobenzoylamino)ethyl}]aminomethyl-2,3-dihydrobenzo[b]furan, which had been prepared in Step A, was dissolved in 2.0 ml of methylene chloride, followed by cooling to 0° C. To the resultant solution was added 0.80 ml (1.35 mmol) of a solution of carbobenzoxy chloride in toluene (manufactured and sold by Tokyo Kasei Kogyo Co., Ltd., Japan) and then, the resultant mixture was stirred at 40° C. for 6 hours to effect a reaction. To the resultant reaction mixture was added 20 ml of chloroform to obtain a mixture. The obtained mixture was successively washed with 20 ml of a saturated aqueous sodium hydrogencarbonate solution, 20 ml of water and 20 ml of saturated saline, to thereby form a chloroform layer, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with a mixed solvent of hexane-ethyl acetate (2:1) to thereby obtain 179 mg of 2-[N-{2-(4-fluorobenzoylamino)ethyl}-N-carbobenzoxy] aminomethyl-2,3-dihydrobenzo[b]furan. 179 mg (0.40 mmol) of the obtained compound was dissolved in 0.72 ml of acetic acid. To the resultant solution was added 0.08 ml of anisole, followed by cooling to 0° C. and then, 1.33 ml of a solution of 30% hydrobromic acid in acetic acid was added thereto. The resultant mixture was stirred at room temperature for 1 hour to effect a reaction. To the resultant reaction mixture was added 20 ml of ether to deposit a precipitate.

The precipitate was collected by filtration. The obtained precipitate was dissolved in 20 ml of chloroform and then, the obtained mixture was successively washed with 20 ml of a saturated aqueous sodium hydrogencarbonate solution, 20 ml of water and 20 ml of saturated saline, to thereby form a chloroform layer containing the desired 2-[N-{2-(4-fluorobenzoylamino)ethyl}]aminomethyl-2,3-dihydrobenzo[b]furan, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with a mixed solvent of chloroform-methanol-concentrated aqueous ammonia (30:1:0.1) to thereby obtain 121 mg of 2-[N-{2-(4-fluorobenzoylamino)ethyl}]aminomethyl-2,3-dihydrobenzo[b]furan as a transparent oily substance (yield: 85%).

EXAMPLE 22

Synthesis of 2-{N-(3-benzoylaminopropyl)}aminomethyl-2,3-dihydrobenzo[b]furan

Step A (Synthesis of 2-{N-(3-benzoylaminopropyl)-N-benzyl}aminomethyl-2,3-dihydrobenzo[b]furan)

445 mg (1.50 mmol) of 2-{N-(3-aminopropyl)-N-benzyl}aminomethyl-2,3-dihydrobenzo[b]furan, which had been prepared in Reference Example 3, was dissolved in 5.0 ml of methylene chloride, followed by cooling to 0° C. To the resultant solution were added 0.42 ml (3.00 mmol) of triethylamine and 0.21 ml (1.8 mmol) of benzoyl chloride. The resultant mixture was stirred at 0° C. for 2 hours to effect a reaction. To the resultant reaction mixture was added 20 ml of chloroform to obtain a mixture. The obtained mixture was successively washed with 20 ml of a saturated aqueous sodium hydrogencarbonate solution, 20 ml of water and 20 ml of saturated saline, to thereby form a chloroform layer containing the desired 2-{N-(3-benzoylaminopropyl)-N-benzyl}aminomethyl-2,3-dihydrobenzo[b]furan, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with a mixed solvent of hexane-ethyl acetate (2:1), to thereby obtain 555 mg of 2-{N-(3-benzoylaminopropyl)-N-benzyl}aminomethyl-2,3-dihydrobenzo[b]furan as a light yellow oily substance (yield: 92%).

Step B (Synthesis of 2-{N-(3-benzoylaminopropyl)}aminomethyl-2,3-dihydrobenzo[b]furan)

180 mg (0.45 mmol) of 2-{N-(3-benzoylaminopropyl)-N-benzyl}aminomethyl-2,3-dihydrobenzo[b]furan, which had been prepared in Step A, was dissolved in 2.0 ml of methylene chloride, followed by cooling to 0° C. To the resultant solution was added 0.80 ml (1.34 mmol) of a solution of carbobenzoxy chloride in toluene (manufactured and sold by Tokyo Kasei Kogyo Co., Ltd., Japan) and then, the resultant mixture was stirred at 40° C. for 4 hours to effect a reaction. To the resultant reaction mixture was added 20 ml of chloroform to obtain a mixture. The obtained mixture was successively washed with 20 ml of a saturated aqueous sodium hydrogencarbonate solution, 20 ml of water and 20 ml of saturated saline, to thereby form a chloroform layer, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with chloroform, to thereby obtain 203 mg of 2-{N-(N-carbobenylaminopropyl)-N-carbobenzoxy}aminomethyl-2,3-dihydrobenzo[b]furan. 152 mg (0.34 mmol) of the obtained compound was dissolved in 0.5 ml of acetic acid. To the resultant solution was added 0.05 ml of anisole, followed by cooling to 0° C. and then, 0.75 ml of a solution of 30% hydrobromic acid in acetic acid was added thereto. The resultant mixture was stirred at room temperature for 1 hour to effect a reaction. To the resultant reaction mixture was added 20 ml of ether to deposit a precipitate. The precipitate was collected by filtration. The obtained precipitate was dissolved in 20 ml of chloroform and then, the obtained mixture was successively washed with 20 ml of a saturated aqueous sodium hydrogencarbonate solution, 20 ml of water and 20 ml of saturated saline, to thereby form a chloroform layer containing the desired 2-{N-(3-benzoylaminopropyl)}aminomethyl-2,3-dihydrobenzo[b]furan, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with a mixed solvent of chloroform-methanol (30:1) to thereby obtain 105 mg of 2-{N-(3-benzoylaminopropyl)}aminomethyl-2,3-dihydrobenzo[b]furan as a light yellow oily substance (yield: 99%).

EXAMPLE 23

Synthesis of 2-[N-{3-(4-fluorobenzoylamino)propyl}]aminomethyl-2,3-dihydrobenzo[b]furan Step A (Synthesis of 2-[N-benzyl-N-{3-(4-fluorobenzoylamino)propyl}]aminomethyl-2,3-dihydrobenzo[b]furan)

227 mg (0.76 mmol) of 2-{N-(3-aminopropyl)-N-benzyl}aminomethyl-2,3-dihydrobenzo[b]furan, which had been prepared in Reference Example 3, was dissolved in 2.0 ml of methylene chloride, followed by cooling to 0° C. To the resultant solution were added 0.23 ml (1.62 mmol) of triethylamine and 0.12 ml (0.97 mmol) of 4-fluorobenzoyl chloride. The resultant mixture was stirred at 0° C. for 2 hours to effect a reaction. To the resultant reaction mixture was added 20 ml of chloroform to obtain a mixture. The obtained mixture was successively washed with 20 ml of a saturated aqueous sodium hydrogencarbonate solution, 20 ml of water and 20 ml of saturated saline, to thereby form a chloroform layer containing the desired 2-[N-benzyl-N-{3-(4-fluorobenzoylamino)propyl}]aminomethyl-2,3-dihydrobenzo[b]furan, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with a mixed solvent of hexane-ethyl acetate (2:1), to thereby obtain 321 mg of 2-[N-benzyl-N-{3-(4-fluorobenzoylamino)propyl}]aminomethyl-2,3-dihydrobenzo[b]furan as a light yellow oily substance (yield: 100%).

Step B (Synthesis of 2-[N-{3-(4-fluorobenzoylamino)propyl}]aminomethyl-2,3-dihydrobenzo[b]furan)

200 mg (0.48 mmol) of 2-[N-benzyl-N-{3-(4-fluorobenzoylamino)propyl}]aminomethyl-2,3-dihydrobenzo[b]furan, which had been prepared Step A, was dissolved in 2.0 ml of methylene chloride, followed by cooling to 0° C. To the resultant solution was added 0.85 ml (1.43 ml) of a solution of carbobenzoxy chloride in toluene (manufactured and sold by Tokyo Kasei Kogyo Co., Ltd., Japan) and then, the resultant mixture was stirred at 40° C. for 2.5 hours to effect a reaction. The resultant reaction mixture was added 20 ml of chloroform to obtain a mixture. The obtained mixture was successively washed with 20 ml of a saturated aqueous sodium hydrogencarbonate solution, 20 ml of water and 20 ml of saturated saline, to thereby form a chloroform layer, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with a mixed solvent of hexane-ethyl acetate (1:1) to thereby obtain 194 mg of 2-[N-{3-(4-fluorobenzoylamino)propyl}-N-carbobenzoxy] aminomethyl-2,3-dihydrobenzo[b]furan. 192 mg (0.42 mmol) of the obtained compound was dissolved in 0.5 ml of acetic acid. To the resultant solution was added 0.05 ml of anisole, followed by cooling to 0° C. and then, 0.92 ml of a solution of 30% hydrobromic acid in acetic acid was added thereto. The resultant mixture was stirred at room temperature for 1 hour to effect a reaction. To the resultant reaction mixture was added 20 ml of ether to deposit a precipitate. The precipitate was collected by filtration. The obtained precipitate was dissolved in 20 ml of chloroform and then, the resultant solution was successively washed with 20 ml of a saturated aqueous sodium hydrogencarbonate solution, 20 ml of water and 20 ml of saturated saline, to thereby form a chloroform layer containing the desired 2-[N-{3-(4-fluorobenzoylamino)propyl}]aminomethyl-2,3-dihydrobenzo[b]furan, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with a mixed solvent of chloroform-methanol (30:1) to thereby obtain 121 mg of 2-[N-{3-(4-fluorobenzoylamino)propyl}]aminomethyl-2,3-dihydrobenzo[b]furan as a light yellow oily substance (yield: 77%).

EXAMPLE 24

Synthesis of 2-{N-(4-benzoylaminobutyl)-N-methyl}aminomethyl-2,3-dihydrobenzo[b]furan 160 mg (0.50 mmol) of 2-{N-(4-benzoylaminobutyl)} aminomethyl-2,3-dihydrobenzo[b]furan, which had been prepared in Example 1, was dissolved in 1.6 ml of methanol, followed by cooling to 0° C. To the resultant solution were added 0.40 ml (5.0 mmol) of a solution of 37% formaldehyde and 31 mg (0.50 mmol) of a sodium cyanoborohydride. The resultant mixture was stirred at 0° C. for 2 hours to effect a reaction. To the resultant reaction mixture was added 20 ml of chloroform to obtain a mixture. The obtained mixture was successively washed with 20 ml of water and 20 ml of saturated saline, to thereby form a chloroform layer containing the desired 2-{N-(4-benzoylaminobutyl)-N-methyl}aminomethyl-2,3-dihydrobenzo[b]furan, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with a mixed solvent of chloroform-methanol (50:1), to thereby obtain 139 mg of 2-{N-(4-benzoylaminobutyl)-N-methyl}aminomethyl-2,3-dihydrobenzo[b]furan as a transparent oily substance (yield: 82%).

EXAMPLE 25

Synthesis of 2-{N-(4-benzoylaminobutyl)-N-ethyl}aminomethyl-2,3-dihydrobenzo[b]furan 160 mg (0.50 mmol) of 2-{N-(4-benzoylaminobutyl)}-aminomethyl-2,3-dihydrobenzo[b]furan, which had been prepared in Example 1, was dissolved in 1.6 ml of acetonitrile. To the resultant solution were added 0.048 ml (0.6 mmol) of ethyl iodide and 138 mg (1.00 mmol) of potassium carbonate. The resultant mixture was stirred at 60° C. for 24 hours to effect a reaction. To the resultant reaction mixture was added 20 ml of chloroform to obtain a mixture. The obtained mixture was successively washed with 20 ml of water and 20 ml of saturated saline, to thereby form a chloroform layer containing the desired 2-{N-(4-benzoylaminobutyl)-N-ethyl)}aminomethyl-2,3-dihydrobenzo[b]furan, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with a mixed solvent of chloroform-methanol (50:1) to thereby obtain 145 mg of 2-{N-(4-benzoylaminobutyl)-N-ethyl}aminomethyl-2,3-dihydrobenzo[b]furan as a light yellow oily substance (yield: 82%).

EXAMPLE 26

Synthesis of 2-{N-(3-benzoylaminopropyl)-N-methyl}aminomethyl-2,3-dihydrobenzo[b]furan 164 mg (0.53 mmol) of 2-{N-(3-benzoylaminopropyl)} aminomethyl-2,3-dihydrobenzo[b]furan, which had been prepared in Example 22, was dissolved in 1.6 ml of methanol, followed by cooling to 0° C. To the resultant solution was added 0.40 ml (5.0 mmol) of a 37% aqueous formaldehyde solution and then, 35 mg (0.56 mmol) of a sodium cyanoborohydride was added thereto. The resultant mixture was stirred at 0° C. for 2 hours to effect a reaction. To the resultant reaction mixture was added 20 ml of chloroform to obtain a mixture. The obtained mixture was successively washed with 20 ml of water and 20 ml of saturated saline, to thereby form a chloroform layer containing the desired 2-{N-(3-benzoylaminopropyl)-N-methyl}aminomethyl-2,3-dihydrobenzo[b]furan, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with a mixed solvent of chloroform-methanol (30:1), to thereby obtain 128 mg of 2-{N-(3-benzoylaminopropyl)-N-methyl}aminomethyl-2,3-dihydrobenzo[b]furan as a transparent oily substance (yield: 72%).

EXAMPLE 27

Synthesis of 2,3-dihydro-2-[N-{4-(4-fluorobenzenesulfonylamino)butyl}]aminomethylbenzo[b]furan Step A (Synthesis of 2-[N-(tert-butoxycarbonyl)-N-{4-(4-fluorobenzenesulfonylamino)butyl}]aminomethyl-2,3-dihydrobenzo[b]furan)

160 mg (0.50 mmol) of 2-{N-(4-aminobutyl)-N-(tert-butoxycarbonyl)}aminomethyl-2,3-dihydrobenzo[b]furan, which had been prepared in Reference Example 1, was dissolved in 1.6 ml of methylene chloride, followed by cooling to 0° C. To the resultant solution were added 0.14 ml (1.0 mmol) of triethylamine and 117 mg (0.60 mmol) of p-fluorobenzenesulfonyl chloride (manufactured and sold by Tokyo Kasei Kogyo Co., Ltd., Japan). The resultant mixture was stirred at 0° C. for 2 hours to effect a reaction. To the resultant reaction mixture was added 20 ml of chloroform to obtain a mixture. The obtained mixture was successively washed with 20 ml of water and 20 ml of saturated saline, to thereby form a chloroform layer containing the desired 2-[N-(tert-butoxycarbonyl)-N-{4-(4-fluorobenzenesulfonylamino)butyl}]aminomethyl-2,3-dihydrobenzo[b]furan, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with a mixed solvent of hexane-ethylacetate (5:1) to thereby obtain 203 mg of 2-[N-(tert-butoxycarbonyl)-N-{4-(4-fluorobenzenesulfonylamino)butyl}]aminomethyl-2,3-dihydrobenzo[b]furan as a light yellow oily substance (yield: 85%).

Step B (Synthesis of 2,3-dihydro-2-[N-{4-(4-fluorobenzenesulfonylamino)butyl}]aminomethylbenzo[b]furan 194 mg (0.40 mmol) of 2-[N-(tert-butoxycarbonyl)-N-{4-(4-fluorobenzenesulfonylamino)butyl}]aminomethyl-2,3-dihydrobenzo[b]furan, which had been prepared in Step A, was cooled to 0° C. To the cooled compound was added 2.0 ml of trifluoroacetic acid. The resultant mixture was stirred at 0° C. for 2 hours to effect a reaction. The resultant reaction mixture was concentrated in vacuo to thereby obtain a residue, and the obtained residue was dissolved in 20 ml of chloroform. The resultant solution was successively washed with 20 ml of a saturated aqueous sodium hydrogencarbonate solution, 20 ml of water and 20 ml of saturated saline, to thereby form a chloroform layer containing the desired 2,3-dihydro-2-[N-{4-(4-fluorobenzonesulfonylamino)butyl}]aminomethylbenzo[b]furan, followed by separation of the chloroform layer. The chloroform layer thus separated was dehydrated by means of a Whatman 1PS filter paper and then, concentrated in vacuo to thereby obtain 148 mg of 2,3-dihydro-2-[N-{4-(4-fluorobenzonesulfonylamino)butyl}]aminomethylbenzo[b]furan as a light yellow oily substance (yield: 97%).

EXAMPLE 28

Synthesis of 2,3-dihydro-2-[N-{4-(3-nitrobenzenesulfonylamino)butyl}]aminomethylbenzo[b]furan Step A (Synthesis of 2-[N-(tert-butoxycarbonyl)-N-{4-(3-nitrobenzenesulfonylamino)butyl}]aminomethyl-2,3-dihydrobenzo[b]furan)

160 mg (0.50 mmol) of 2-{N-(4-aminobutyl)-N-(tert-butoxycarbonyl)}aminomethyl-2,3-dihydrobenzo[b]furan, which had been prepared in Reference Example 1, was dissolved in 1.6 ml of methylene chloride, followed by cooling to 0° C. To the resultant solution were added 0.14 ml (1.0 mmol) of triethylamine and 133 mg (0.60 mmol) of m-nitrobenzenesulfonyl chloride (manufactured and sold by Tokyo Kasei Kogyo Co., Ltd., Japan). The resultant mixture was stirred at 0° C. for 2 hours to effect a reaction. To the resultant reaction mixture was added 20 ml of chloroform to obtain a mixture. The obtained mixture was successively washed with 20 ml of water and 20 ml of saturated saline, to thereby form a chloroform layer containing the desired 2-[N-(tert-butoxycarbonyl)-N-{4-(3-nitrobenzenesulfonylamino)butyl}]aminomethyl-2,3-dihydrobenzo[b]furan, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with a mixed solvent of hexane-ethyl acetate (3:1) to thereby obtain 180 mg of 2-[N-(tert-butoxycarbonyl)-N-{4-(3-nitrobenzenesulfonylamino)butyl}]aminomethyl-2,3-dihydrobenzo[b]furan as a light yellow oily substance (yield: 71%).

Step B (Synthesis of 2,3-dihydro-2-[N-{4-(3-nitrobenzenesulfonylamino)butyl}]aminomethylbenzo[b]furan 180 mg (0.36 mmol) of 2-[N-(tert-butoxycarbonyl)-N-{4-(3-nitrobenzenesulfonylamino)butyl}]aminomethyl-2,3-dihydrobenzo[b]furan, which had been prepared in Step A, was cooled to 0° C. To the cooled compound was added 2.0 ml of trifluoroacetic acid. The resultant mixture was stirred at 0° C. for 2 hours to effect a reaction. The resultant reaction mixture was concentrated in vacuo to thereby obtain a residue. The obtained residue was dissolved in 20 ml of chloroform to obtain a mixture. The obtained mixture was successively washed with 20 ml of a saturated aqueous sodium hydrogencarbonate solution, 20 ml of water and 20 ml of saturated saline, to thereby form a chloroform layer containing the desired 2,3-dihydro-2-[N-{4-(3-nitrobenzenesulfonylamino)butyl}]aminomethylbenzo-[b]furan, followed by separation of the chloroform layer. The chloroform layer thus separated was dehydrated by means of a Whatman 1PS filter paper and then, concentrated in vacuo to thereby obtain 143 mg of 2,3-dihydro-2-[N-{4-(3-nitrobenzenesulfonylaminobutyl}]aminomethylbenzo[b]furan as a light yellow oily substance (yield: 99%).

EXAMPLE 29

Synthesis of 2,3-dihydro-2-[N-{4-(2-hydroxybenzoylamino)butyl}]aminomethylbenzo[b]furan Step A (Synthesis of 2-[N-(tert-butoxycarbonyl)-N-{4-(2-acetoxybenzoylamino)butyl}]aminomethyl-2,3-dihydrobenzo[b]furan 640 mg (2.00 mmol) of 2-{N-(4-aminobutyl)-N-(tert-butoxycarbonyl)}aminomethyl-2,3-dihydrobenzo[b]furan, which had been prepared in Reference Example 1, was dissolved in 7 ml of methylene chloride, followed by cooling to 0° C. To the resultant solution were added 0.42 ml (3.0 mmol) of triethylamine and 497 mg (2.50 mmol) of o-acetylsalicyloyl chloride (manufactured and sold by Aldrich Chemical Co., Inc., U.S.A.). The resultant mixture was stirred at 0° C. for 2 hours to effect a reaction. To the resultant reaction mixture was added 20 ml of chloroform to obtain a mixture. The obtained mixture was successively washed with 20 ml of water and 20 ml of saturated saline, to thereby form a chloroform layer containing the desired 2-[N-(tert-butoxycarbonyl)-N-{4-(2-acetoxybenzoylamino)butyl}] aminomethyl-2,3-dihydrobenzo[b]furan, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 20 g of silica gel (Art. 9385, manufactured and sold by E. Merck, Darmstadt, Germany) and eluted with chloroform to thereby obtain 760 mg of 2-[N-(tert-butoxycarbonyl)-N-{4-(2-acetoxybenzoylamino)butyl}] aminomethyl-2,3-dihydrobenzo[b]furan as a light yellow oily substance (yield: 79%).

Step B (Synthesis of 2,3-dihydro-2-[N-{4-(2-hydroxybenzoylamino)butyl}]aminomethylbenzo[b]furan 600 mg (1.24 mmol) of 2-[N-(tert-butoxycarbonyl)-N-{4-(2-acetoxybenzoylamino)butyl}]aminomethyl-2,3dihydrobenzo[b]furan, which had been prepared in Step A, was dissolved in 6 ml of methanol, followed by cooling to 0° C. To the resultant solution was added 1.5 ml of a 1N solution of sodium methoxide in methanol and then, the resultant mixture was stirred at 0° C. for 2 hours to effect a reaction. To the resultant reaction mixture was added 20 ml of chloroform. The obtained mixture was successively washed with 20 ml of a saturated aqueous ammonium chloride solution, 20 ml of water and 20 ml of saturated saline, to thereby form a chloroform layer, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with chloroform to thereby obtain a light yellow oily substance. The obtained oily substance was cooled to 0° C. To the cooled compound was added 4.8 ml of trifluoroacetic acid. The resultant mixture was stirred at 0° C. for 2 hours to effect a reaction. The resultant reaction mixture was concentrated in vacuo to thereby obtain a residue. The obtained residue was dissolved in 20 ml of chloroform. The resultant solution was successively washed with 20 ml of a saturated aqueous sodium hydrogencarbonate solution, 20 ml of water and 20 ml of saturated saline, to thereby form a chloroform layer containing the desired 2,3-dihydro-2-[N-{4-(2-hydroxybenzoylamino)butyl}]aminomethylbenzo[b]furan, followed by separation of the chloroform layer. The chloroform layer thus separated was dehydrated by means of a Whatman 1PS filter paper and then, concentrated in vacuo to thereby obtain 332 mg of 2,3-dihydro-2-[N-{4-(2-hydroxybenzoylamino)butyl}]aminomethylbenzo[b]furan as a white bubbly substance (yield: 79%).

TABLE 1

Affinity for serotonin 1A receptor

| Example No. | 5-HT1A Ki (nM) |
|---|---|
| 1 | 2.9 |
| 2 | 11 |
| 4 | 1.2 |
| 5 | 12 |
| 7 | 4.3 |
| 9 | 8.2 |
| 10 | 3.0 |
| 11 | 2.6 |

TABLE 1-continued

Affinity for serotonin 1A receptor

| Example No. | 5-HT1A Ki (nM) |
|---|---|
| 13 | 5.3 |
| 15 | 11 |
| 18 | 1.3 |
| 19 | 3.7 |
| 20 | 1.6 |
| 21 | 2.0 |
| 23 | 12 |
| 24 | 11 |
| 25 | 3.1 |
| 29 | 5.4 |

TABLE 2

Activities against emesis

| Example No. | Dose (mg/kg) | Time for occurrence of emesis (Maximum: 10 minutes) | Number of tested suncus |
|---|---|---|---|
| Physiological saline | | 55 sec. | 4 |
| 1 | 1 | 10 min. | 4 |
| 2 | 3 | 6 min. 4 sec. | 4 |
| 4 | 3 | 10 min. | 4 |
| 5 | 3 | 3 min. 9 sec. | 4 |
| 7 | 3 | 7 min. 15 sec. | 4 |
| 9 | 3 | 8 min. 5 sec. | 4 |
| 10 | 3 | 9 min. 43 sec. | 4 |
| 11 | 3 | 10 min. | 4 |
| 18 | 1 | 9 min. 2 sec. | 4 |
| 22 | 3 | 7 min. 6 sec. | 4 |
| 24 | 3 | 10 min. | 4 |
| 25 | 3 | 7 min. 35 sec. | 4 |

TABLE 3

Affinity for adrenaline α1 receptor

| Example No. | adrenaline α1 Ki (nM) |
|---|---|
| 1 | 350 |
| 2 | 270 |
| 4 | 270 |
| 5 | 290 |
| 7 | 340 |
| 9 | 330 |
| 10 | 420 |
| 11 | 300 |
| 13 | 380 |
| 15 | 250 |
| 18 | 270 |
| 24 | 760 |
| 25 | 710 |
| 29 | 260 |

TABLE 4

Anti-depression activity
(evaluated by forced Swimming test using rats)

| Example No. | Dose (mg/kg p.o.) | Time spent in immobile state (sec.) | Number of tested rats |
|---|---|---|---|
| Physiological saline | | 200 | 6 |
| 1 | 30 | 117 | 6 |

TABLE 4-continued

Anti-depression activity
(evaluated by forced Swimming test using rats)

| Example No. | Dose (mg/kg p.o.) | Time spent in immobile state (sec.) | Number of tested rats |
|---|---|---|---|
| 17 | 60 | 142 | 6 |
| 18 | 30 | 142 | 6 |

TABLE 5

Substituents in compounds of Examples

| Example No. | $R^1$ | n | A | $R^2$ |
|---|---|---|---|---|
| 1 | H | 4 | CO | H |
| 2 | H | 4 | SO2 | H |
| 3 | H | 4 | CO | 2-Me |
| 4 | H | 4 | CO | 3-Me |
| 5 | H | 4 | CO | 4-Me |
| 6 | H | 4 | CO | 2-OMe |
| 7 | H | 4 | CO | 3-OMe |
| 8 | H | 4 | CO | 4-OMe |
| 9 | H | 4 | CO | 2-F |
| 10 | H | 4 | CO | 3-F |
| 11 | H | 4 | CO | 4-F |
| 12 | H | 4 | CO | 2-CF3 |
| 13 | H | 4 | CO | 3-CF3 |
| 14 | H | 4 | CO | 4-CF3 |
| 15 | H | 4 | CO | 3-NO2 |
| 16 | H | 4 | CO | 3-CN |
| 17 | (+) H | 4 | CO | H |
| 18 | (−) H | 4 | CO | H |
| 19 | H | 2 | CO | H |
| 20 | H | 2 | CO | 3-Me |
| 21 | H | 2 | CO | 4-F |
| 22 | H | 3 | CO | H |
| 23 | H | 3 | CO | 4-F |
| 24 | Me | 4 | CO | H |
| 25 | Et | 4 | CO | H |
| 26 | Me | 3 | CO | H |
| 27 | H | 4 | SO2 | 4-F |
| 28 | H | 4 | SO2 | 3-NO2 |
| 29 | H | 4 | CO | 2-OH |

TABLE 6

Physical properties

| Compound | $^1$H-NMR (CDCl$_3$) δ(ppm) MASS(FAB) |
|---|---|
| Reference Example 1 Step A | 2.29 (3H, s) 3.30 (2H, d, J =6.6 Mz) 5.00–5.10 (2H, m) 5.80–6.00 (1H, m) 7.15–7.30 (4H, m) 176 (MH$^+$) |
| Reference Example 1 Step B | 2.36 (3H, s), 2.86 (1H, dd, J =14.5Hz, 9.2 Hz) 3.63 (1H, dd, J=14.55 Hz, 4.3 Hz) 3.67 (1H, t, J=10.0 Hz) 3.89 (1H, dd, J=10.2 Hz, 3.9 Hz 4.25–4.35 (1H, m) 337 (MH$^+$) |
| Reference Example 1 Step C | 3.12 (1H, dd, J=15.8 Hz, 6.5 Hz) 3.35–3.65 (3H, m) 4.95–5.05 (1H, m) 6.79 (1H, d, J=7.9 Hz) 6.87 (1H, t, J=7.5 Hz) 7.10–7.20 (2H, m) 212 (M$^+$) |
| Reference Example 1 Step D | 6.01–1.75 (4H, m) 2.65–3.00 (1H, dd, J=15.5 Hz, 9.2 Hz) 3.60 (2H, t, J=5.0 Hz) 4.35–5.00 (1H, m) 6.76 (1H, d, J=7.9 Hz) 6.84 (1H, t, J=7.2 Hz) 7.05–7.20 (2H, m) |

TABLE 6-continued

Physical properties

| Compound | $^1$H-NMR (CDCl$_3$) δ(ppm) MASS(FAB) |
|---|---|
| | 222 (MH$^-$) |
| Reference Example 1 Step E | 1.40–1.60 (4H, m) 1.46 (9H, s) 2.89 (1H, dd, J=15.8 Hz, 7.3 Hz) 3.20–3.65 (7H, m) 5.00 (1H, brs) 6.76 (1H, d, J=7.9 Hz) 6.84 (1H, t, J=7.5 Hz) 7.00–7.20 (2H, m) 322 (MH$^+$), 222 |
| Reference Example 1 Step F | 1.40–1.75 (4H, m) 1.44 (9H, s) 2.44 (3H, s) 2.86 (1H, dd, J=15.8 Hz, 7.2 Hz) 3.20–3.70 (5H, m) 4.05 (2H, t, J=5.9 Hz) 4.95 (1H, brs) 6.73 (1H, d, J=7.6 Hz) 6.84 (1H, t, J=7.5 Hz) 7.05–7.20 (2H, m) 7.33 (2H, d, J=8.3 Hz) 7.78 (2H, d, J=8.3 Hz) 476 (MH$^+$), 376 |
| Reference Example 1 Step G | 1.40–1.70 (4H, m) 1.47 (9H, s) 2.89 (1H, dd, J=15.8 Hz, 7.3 Hz) 3.20–3.75 (7H, m) 5.00 (1H, brs) 6.76 (1H, d, J=7.9 Hz) 6.84 (1H, t, J=7.4 Hz) 7.00–7.20 (2H, m) 347 (MH$^-$), 247 |
| Reference Example 1 Step H | 321 (MH$^-$), 221 |
| Reference Example 2 Step A | 1.70 (1H, s) 2.85–3.05 (3H, m) 3.25 (1H, d d, J=15.5 Hz, 9.2 Hz) 3.86 (2H, s) 4.90–5.00 (1H, m) 6.75–6.90 (2H, m) 7.05–7.20 (2H, m) 7.20–7.40 (5H, m) 240 (MH$^+$) |
| Reference Example 2 Step B | 2.70–3.00 (5H, m) 3.10 (1H, dd, J=15.5 Hz, 9.2 Hz) 3.65–3.90 (4H, m) 4. 80–4.95 (1H, m) 6.66 (1H, d, J=7.9 Hz) 6.70–6.80 (1H, m) 7.00–7.30 (7H, m) 7.65–7.75 (2H, m) 7.75–7.85 (2H, m) 413 (MH$^+$) |
| Reference Example 2 Step C | 1.63 (2H, s) 2.60–2.95 (7H, m) 3.22 (1H, dd, J=15.7 Hz, 9.1 Hz) 3.72 (1H, d, J=13.7 Hz) 3.75 (1H, d, J=13.7 Hz) 4.85–5.00 (1H, m) 6.76 (1H, d, J=7.9 Hz) 6.75–6.85 (1H, m) 7.05–7.20 (2H, m) 7.20–7.35 (5H, m) 283 (MH$^+$) |
| Reference Example 3 Step A | 8.01–1.95 (2H, m) 2.55–2.90 (4H, m) 2.95 (1H, dd, J=15.7 Hz, 7.4 Hz) 3.21 (1H, dd, J=15.7 Hz, 9.1 Hz) 3.60–3.80 (4H, m) 4.80–4.95 (1H, m) 6.69 (1H, d, J=7.9 Hz) 6.79 (1H, dd, J=7.6 Hz, 7.3 Hz) 7.00–7.40 (7H, m) 7.65–7.75 (2H, m) 7.80–7.90 (2H, m) 427 (MH$^+$) |
| Reference Example 3 Step B | 1.53 (2H, s) 1.55–1.70 (2H, m) 2.50–2.75 (5H, m) 2.82 (1H, dd, J=13.5 Hz, 6.3 Hz) 2.92 (1H, dd, J=15.5 Hz, 7.6 Hz) 3.20 (1H, dd, J=15.5 Hz, 9.1 Hz) 3.64 (1H, d, J=13.7 Hz) 3.73 (1H, d, J=13, Hz) 4.80–4.95 (1H, m) 6.75 (1H, d, J=7.9 Hz) 6.81 (1H, dd, J=7.6 Hz, 7.3 Hz) 7.00–7.15 (2H, m) 7.20–7.35 (5 H, m) 297 (MH$^+$) |
| Example 1 Step A | 1.45 (9H, s) 1.50–1.10 (4H, m) 2.87 (1H, dd, J=15.7 Hz, 7.2 Hz) 3.20–3.70 (7H, m) 5.00 (1H, brs) 6.73 (1H, d, J=7.9 Hz) 6.83 (1H, t, J=7.5 Hz) 7.00–7.20 (2H, m) 7.35–7.85 (5H, m) 425 (MH$^+$), 325 |
| Example 1 | 1.45–1.65 (5H, m) 2.64 (2H, t, |

TABLE 6-continued

Physical properties

| Compound | $^1$H-NMR (CDCl$_3$) δ(ppm) MASS(FAB) |
|---|---|
| Step B | J=6.6 Hz) 2.65–2.85 (3H, m) 3.16 (1 H, dd, J=15.5 Hz, 9.2 Hz) 3.38 (2H, d,t, J=6.3 Hz, 6.3 Hz) 4.75–4.85 (1H, m) 6.68 (1H, d, J=7.9 Hz) 6.75 (1H, t, J=7.5 Hz) 6.90 (1 H, brs) 6.95–7.10 (2H, m) 7.25–7.40 (3H, m) 7.68 (2H, d, J=7.3 Hz) 325 (MH$^+$) |
| Example 2 Step A | 1.40–1.70 (4H, m) 1.54 (9H, s) 2.95 (1H, dd, J=1 5.5 Hz, 7.1 Hz) 3.00–3.75 (7H, m) 5.05 (1H, brs) 6.83 (1H, d, J=7.6 Hz) 6.94 (1H, t, J=7.3 Hz) 7.15–7.35 (2H, m) 7.55–7.70 (3H, m) 7.90–8.00 (2H, m) 461 (MH$^+$), 361 |
| Example 2 Step B | 1.35–1.60(5H, m) 2.45–3.00 (7H, m) 3.23 (1H, dd, J=15.5 Hz, 9.2 Hz) 4.85–5.00 (1H, m) 6.69 (1H, d J=8.0 Hz) 6.76 (1H, t, J=7.3 Hz) 7.00–7.20 (2H, m) 7.35–7.50 (3H, m) 7.78 (2H, d, J =7.7 Hz) 325 (MH$^+$) |
| Example 3 Step A | 1.45 (9H, s) 1.50–1.75 (4H, m) 2.43 (3H, s) 2.88 (1H, dd, J=15.8 Hz, 6.9 Hz) 3.20–3.55 (7H, m) 4.96 (1H, brs) 6.73 (1H, d, J=7.9 Hz) 6.83 (1H, t, J=7.4 Hz) 7.05–7.40 (6H, m) 439 (MH$^+$), 339 |
| Example 3 Step B | 1.50–7.70 (5H, m) 2.36 (3H, s) 2.60–2.85 (5H, m) 3.09 (1H, dd, J=15.5 Hz, 9.2 Hz) 3.30-3.45 (2H, m) 4.60–4.75 (1H, m) 6.57 (1H, brs) 6.67 (1H, d, J=7.9 Hz) 6.74 (1H, t, J=7.4 Hz) 7.00–7.35 (6H, m) 339 (MH$^+$) |
| Example 4 Step A | 1.45 (9H, s) 1.55–1.70 (4H, m) 2.37 (3H, s) 2.87 (1H, dd, J=15.7 Hz, 7.1 Hz) 3.20–3.55 (7H, m) 4.96 (1H, brs) 6.83 (1H, d, J=7.9 Hz) 6.83 (1H, t, J=7.4 Hz) 7.05–7.35 (5H, m) 1.50–7.70 (2H, m) 439 (MH$^+$), 339 |
| Example 4 Step B | 1.50–1.70 (5H, m) 2.30 (3H, s) 2.65 (2H, t, J=6.6 Hz) 2.70–2.90 (3H, m) 3.17 (1H, dd, J=15.5 Hz, 9.2 Hz) 3.38 (2H, dd, J=12.2 Hz, 6.3 Hz) 4.75–4.90 (1H, m) 6.68 (1H, d, J=7.9 Hz) 6.75 (1H, brs) 6.75 (1H, t, J=7.4 Hz) 7.19 (2H, d, J=5.6 Hz) 7.45–7.50 (1H, m) 7.52 (1H, s) 339 (MH$^+$) |
| Example 5 Step A | 1.45 (9H, s) 1.55–1.75 (4H, m) 2.37 (3H, s) 2.87 (1H, dd, J=15.7 Hz, 6.6 Hz) 3.20–3.55 (7H, m) 4.95 (1H, brs) 6.73 (1H, d, J=7.9 Hz) 6.83 (1H, t, J=7.4 Hz) 7.00–7.25 (5H, m) 7.65–7.80 (2H, m) 439 (MH$^+$), 339 |
| Example 5 Step B | 1.50–1.75 (5H, m) 2.29 (3H, s) 2.63 (2H, t, J=6.4 Hz) 2.70–2.90 (3H, m) 3.16 (1H, dd, J=15.5 Hz, 8.9 Hz) 3.36 (2H, dd, J=12.0 Hz, 6.1 Hz) 4.75–4.90 (1H, m) 6.67 (1H, d, J=7.9 Hz) 6.74 (1H, t, J=7.4 Hz) 6.82 (1H, brs) 7.00–7.15 (4H, m) 7.58 (2H, d, J=7.9 Hz) 329 (MH$^+$) |
| Example 6 Step A | 1.45 (9H, s) 1.50–1.70 (4H, m) 2.88 (1H, dd, J=5.8 Hz, 7.3 Hz) 3.20–3.60 (7H, m) 3.93 (3H, s) 4.98 (1H, brs) 6.73 (1H, d, J=7.9 Hz) 6.82 (1H, t, J=7.4 Hz) 6.95 (1H, d, J=8.6 Hz) 7.00–7.20 (3H, m) 7.40–7.50 (1H, m) 7.87 (1H, brs) 8.19 (1H, d, J=17.8 Hz) 455 (MH$^+$), 355 |
| Example 6 Step B | 1.50–1.70 (5H, m) 2.65 (2H, t, J=6.3 Hz) 2.70–2.90 (3H, m) 3.19 (1H, dd, J=15.5 Hz, 9.2 Hz) 3.40 (2H, dd, J=12.4 Hz, 6.8 Hz) 3.87 (3H, s) 4.75–4.95 (1H, m) 6.68 (1H, d, J=7.9 Hz) 6.74 (1H, t, J=7.4 Hz) 6.89 (1H, d, J=8.3 Hz) 6.95–7.15 (3H, m) 7.30–7.40 (1H, m) 8.10 (1H, brs) 8.12 (1H, dd, J=7.8 Hz, 1.8 Hz) 355 (MH$^+$) |
| Example 7 Step A | 1.45 (9H, s) 1.50–1.80 (4H, m) 2.87 (1H, dd, J=15.7 Hz, 7.1 Hz) 3.20–3.70 (7H, m) 3.83 (3H, s) 4.97 (1H, brs) 6.73 (1H, d, J=7.9 Hz) 6.83 (1H, t, J=7.4 Hz) 7.00–7.50 (7H, m) 455 (MH$^+$), 355 |
| Example 7 Step B | 1.50–1.80 (5H, m) 2.60–2.90 (4H, m) 3.17 (1H, dd, J=15.5 Hz, 8.9 Hz) 3.30–3.50 (2H, m) 3.74 (3H, s) 4.70–4.90 (1H, m) 6.68 (1H, d, J=7.9 Hz) 6.75 (1H, t, J=7.4 Hz) 6.80–7.30 (7H, m) 355 (MH$^+$) |
| Example 8 Step A | 1.46 (9H, s) 1.50–1.80 (4H, m) 2.88 (1H, dd, J=15.8 Hz, 6.9 Hz) 3.20–3.60 (7H, m) 3.83 (3H, s) 4.96 (1H, brs) 6.70–6.90 (4H, m) 7.00–7.20 (4H, m) 7.70–7.90 (2H, m) 455 (MH$^+$), 355 |
| Example 8 Step B | 1.50–1.80 (5H, m) 2.60–2.90 (4H, m) 3.17 (1H, dd, J=15.5 Hz, 9.2 Hz) 3.30–3.50 (2H, m) 3.74 (3H, s) 4.75–4.90 (1H, m) 6.70–6.90 (5H, m) 7.00–7.10 (2H, m) 7.66 (2H, d, J=8.9 Hz) 355 (MH$^-$) |
| Example 9 Step A | 1.45 (9H, s) 1.50–1.80 (4H, m) 2.88 (1H, dd, J=15.1 Hz, 7.1 Hz) 3.20–3.70 (7H, m) 4.98 (1H, brs) 6.74 (1H, d, J=7.9 Hz) 6.82 (1H, t, J=7.4 Hz) 7.00–7.50 (5H, m) 8.07 (1H, t, J=7.4 Hz) 443 (MH$^-$), 343 |
| Example 9 Step B | 1.50–1.80 (5H, m) 2.65 (2H, t, J=6.8 Hz) 2.75 (1H, dd, J=12.5 Hz, 4.0 Hz) 2.80–2.90 (2H, m) 3.18 (1H, dd, J=15.5 Hz, 9.2 Hz) 3.42 (2H, dd, J=12.2 Hz, 5.6 Hz) 4.70–4.90 (1H, m) 6.68 (1H, d, J=7.9 Hz) 6.74 (1H, t, J=7.4 Hz) 6.90 (1H, brs) 6.95–7.45 (5H, m) 7.99 (1H, dt, J=7.9 Hz, 2.0 Hz) 343 (MH$^-$) |
| Example 10 Step A | 1.46 (9H, s) 1.50–1.80 (4H, m) 2.87 (1H, dd, J=15.7 Hz, 7.1 Hz) 3.20–3.60 (7H, m) 4.96 (1H, brs) 6.74 (1H, d, J=7.6 Hz) 6.83 (1H, t, J=7.3 Hz) 7.00–7.70 (6H, m) 443 (MH$_-$), 343 |
| Example 10 Step B | 1.40–1.70 (5H, m) 2.65 (2H, t, J=6.4 Hz) 2.70–2.90 (3H, m) 3.17 (1H, dd, J=15.5 Hz, 9.2 Hz) 3.38 (2H, dd, J=12.1 Hz, 6.6 Hz) 4.70–4.90 (1H, m) 6.67 (1H, d, J=7.9 Hz) 6.75 (1H, t, J=7.4 Hz) 7.00–7.50 (7H, m) 343 (MH$^-$) |

TABLE 6-continued

Physical properties

| Compound | $^1$H-NMR (CDCl$_3$) δ(ppm) MASS(FAB) |
|---|---|
| Example 11 Step A | 1.46 (9H, s) 1.50–1.80 (4H, m) 2.87 (1H, dd, J=15.7 Hz, 7.1 Hz) 3.20–3.80 (7H, m) 4.95 (1H, brs) 6.74 (1H, d, J=7.6 Hz) 6.84 (1H, t, J=7.4 Hz) 7.00–7.20 (4H, m) 7.70–7.90 (2H, m) 443 (MH$^+$), 343 |
| Example 11 Step B | 1.50–1.80 (5H, m) 2.65 (2H, t, J=6.4 Hz) 2.70–2.90 (3H, m) 3.17 (1H, dd, J=15.5 Hz, 9.2 Hz) 3.37 (2H, dd, J=11.9 Hz, 6.3 Hz) 4.70–4.90 (1H, m) 6.68 (1H, d, J=8.3 Hz) 6.76 (1H t, J=6.4 Hz) 6.90–7.10 (4H, m) 7.60–7.70 (2H, m) 343 (MH$^+$) |
| Example 12 Step A | 1.40–1.80 (13H, m) 2.88 (1H, dd, J=15.8 Hz, 7.3 Hz) 3.20–3.70 (7H, m) 4.96 (1H, brs) 6.73 (1H, d, J=7.9 Hz) 6.82 (1H, t, J=7.3 Hz) 7.00–7.20 (2H, m) 7.45–7.70 (4H, m) 493 (MH$^+$), 393 |
| Example 12 Step B | 4.01–1.80 (5H, m) 2.50–2.80 (4H, m) 3.06 (1H, dd, J=15.5 Hz, 9.2 Hz) 3.30–3.50 (2H, m) 4.50–4.70 (1H, m) 6.66 (1H, d, J=7.9 Hz) 6.74 (1H, t, J=7.4 Hz) 6.83 (1H, brs) 6.95–7.10 (2H, m) 7.40–7.60 (3H, m) 7.60 (1H, d, J=7.6 Hz) 393 (MH$^-$) |
| Example 13 Step A | 1.44 (9H, s) 1.50–1.80 (4H, m) 2.87 (1H, dd, J=5.7 Hz, 7.1 Hz) 3.20–3.60 (7H, m) 4.95 (1H, brs) 6.70–6.90 (2H, m) 7.00–7.20 (2H, m) 7.45–7.60 (1H, m) 7.60–7.70 (1H, m) 7.95–8.20 (2H, m) 493 (MH$^-$), 393 |
| Example 13 Step B | 1.50–1.80 (5H, m) 2.66 (2H, t, J=6.4 Hz) 2.70–2.90 (3H, m) 3.16 (1H, dd, J=15.5 Hz, 9.2 Hz) 3.40 (2H, dd, J=11.9 Hz, 5.9 Hz) 4.75–4.85 (1H, m) 6.65 (1H, d, J=7.9 Hz) 6.75 (1H, t, J=7.4 Hz) 7.02 (1H, J=7.9 Hz) 7.06 (1H, d, J=7.4 Hz) 7.40 (1H, brs) 7.43 (1H, t, J=7.8 Hz) 7.63 (1H, d, J=7.6 Hz) 7.88 (1H, d, J=7.6 Hz) 7.96 (1H, s) 393 (MH$^+$) |
| Example 14 Step A | 1.46 (9H, s) 1.55–1.75 (4H, m) 2.88 (1H, dd, J=15.8 Hz, 6.9 Hz) 3.20–3.70 (7H, m) 4.95 (1H, brs) 6.74 (1H, d, J=7.9 Hz) 6.84 (1H, t, J=7.3 Hz) 7.00–7.40 (2H, m) 7.66 (2H, d, J=7.9 Hz) 7.80–8.05 (3H, m) 493 (MH$^+$), 393 |
| Example 14 Step B | 1.50–1.80 (5H, m) 2.67 (2H, t, J=6.4 Hz) 2.70–2.90 (3H, m) 3.17 (1H, dd, J=15.8 Hz, 9.2 Hz) 3.40 (2H, dd, J=11.9 Hz, 6.3 Hz) 4.75–4.90 (1H, m) 6.67 (1H, d, J=7.9 Hz) 6.76 (1H, t, J=7.4 Hz) 7.00–7.10 (2H, m) 7.30 (1H, brs) 7.56 (2H, d, J=8.3 Hz) 7.80 (2H, d, J=8.3 Hz) 393 (MM$^+$) |
| Example 15 Step A | 1.45 (9H, s) 1.60–1.80 (4H, m) 2.87 (1H, dd, J=15.7 Hz, 7.1 Hz) 3.20–3.70 (7H, m) 4.96 (1H, brs) 6.72 (1H, d, J=7.3 Hz) 6.83 (1H, t, J=7.3 Hz) 7.05–7.20 (2H, m) 7.55–7.20 (2H, m) 8.15–8.35 (2H, m) 470 (MH$^+$), 370 |
| Example 15 Step B | 1.55–1.80 (5H, m) 2.71 (2H, t, J=6.3 Hz) 2.75–2.90 (3H, m) 3.17 (1H, dd, J=15.5 Hz, 9.2 Hz) 3.44 (2H, dd, J=11.4 Hz, 5.4 Hz) 4.70–4.85 (1H, m) 6.62 (1H, d, J=7.9 Hz) 6.74 (1H, t, J=7.4 Hz) 7.01 (1H, t, J=7.6 Hz) 7.04 (1H, d, J=7.3 Hz) 7.52 (1H, t, J=8.1 Hz) 7.17 (1H, brs) 8.10–8.30 (2H, m) 8.51 (1H, t, J=2.0 Hz) 370 (MH$^+$) |
| Example 16 Step A | 1.48 (9H, s) 1.55–1.80 (4H, m) 2.88 (1H, dd, J=15.8 Hz, 7.1 Hz) 3.20–3.70 (7H, m) 4.96 (1H, brs) 6.74 (1H, d, J=7.9 Hz) 6.84 (1H, t, J=7.3 Hz) 7.05–7.20 (2H, m) 1.53 (1H, t, J=7.8 Hz) 7.60–7.80 (2H, m) 8.00–8.30 (2H, m) 450 (MH$^+$), 350 |
| Example 16 Step B | 1.60–1.85 (5H, m) 2.76 (2H, t, J=6.3 Hz) 2.80–2.95 (3H, m) 3.28 (1H, dd, J=15.5 Hz, 9.2 Hz) 3.48 (2H, dd, J=11.7 Hz, 6.1 Hz) 4.80 4.95 (1H, m) 6.74 (1H, d, J=7.9 Hz) 6.83 (1H, t, J=7.4 Hz) 7.10 (1H, t, J=7.8 Hz) 7.14 (1H, d, J=7.6 Hz) 7.52 (1H, t, J=7.9 Hz) 7.57 (1H, brs) 1.70–7.80 (1H, m) 8.0–8.10 (2H, m) 350 (MH$^-$) |
| Example 17 | NXR spectra of compound (in the form of a free base) obtained are the same as those of the compound of Example 1. 325 (MH$^+$) |
| Example 18 | NXR spectra of compound (in the form of a free base) obtained are the same as those of the compound of Example 1. 325 (MH$^+$) |
| Example 19 Step A | 2.70–3.00 (5H, m) 3.22 (1H, dd, J=15.5 Hz, 9.2 Hz) 3.30–3.45 (1H, m) 3.55–3.70 (1H, m) 3.72 (1H, d, J=13.7 Hz) 3.84 (1H, d, J=13.7 Hz) 4.85–5.00 (1H, m) 6.60 (1H, d, J=7.9 Hz) 6.75–6.85 (1H, m) 7.00–7.40 (8H, m) 7.40–7.55 (3H, m) 7.75–7.85 (2H, m) 387 (MH$^-$) |
| Example 19 Step B | 1.94 (1H, s) 2.80–2.95 (5H, m) 3.20 (1H, dd, J=15.7 Hz, 9.4 Hz) 3.40–3.55 (2H, m) 4.80–4.95 (1H, m) 6.67 (1H, d, J=8.3 Hz) 6.70–6.50 (1H, m) 6.85 (1H, brs) 7.00–7.15 (2H, m) 7.30–7.50 (3H, m) 7.65–7.75 (2H, m) 297 (MH$^-$) |
| Example 20 Step A | 2.42 (3H, s) 2.80–3.00 (5H, m) 3.23 (1H, dd, J=15.5 Hz, 9.2 Hz) 3.30–3.45 (1H, m) 3.55–3.70 (1H, m) 3.73 (1H, d, J=13.5 Hz) 3.84 (1H, d, J=13.5 Hz) 4.85–5.00 (1H, m) 6.61 (1H, d, J=7.9 Hz) 6.82 (1H, dd, J=7.6 Hz, 7.3 Hz) 7.05–7.15 (3H, m) 7.20–7.40 (7H, m) 7.55–7.70 (1H, m) 7.66 (1H, s) 401 (MH$^-$) |
| Example 20 Step B | 1.75 (1H, brs) 2.39 (3H, s) 2.90–3.00 (5H, m) 3.27 (1H, dd, J=15.5 Hz, 9.2 Hz) 3.50–3.60 (2H, m) 4.85–5.00 (1H, m) 6.75 (1H, d, J=7.9 Hz) 6.80–6.90 (2H, m) 7.05–7.20 (2H, m) 7.25–7.30 (2H, m) 7.50–7.60 (1H, m) 7.61 (1H, s 311 (MH$^+$) |
| Example 21 Step A | 2.70–2.95 (5H, m) 3.20–3.40 (2H, m) 3.55–3.70 (1H, m) 3.71 (1H, d, J=13.5 Hz) 3.84 (1H, d, J=13.5 Hz) 4.85–5.00 (1H, m) 6.59 (1H, d, J= |

TABLE 6-continued

| Compound | Physical properties<br>$^1$H-NMR (CDCl$_3$) δ(ppm)<br>MASS(FAB) |
|---|---|
| | 7.9 Hz) 6.80–6.90 (1H, m) 7.00–<br>7.35 (10H, m) 7.81 (2H, dd, J=<br>8.9 Hz, 5.3 Hz)<br>405 (MH$^+$) |
| Example 21<br>Step B | 1.82 (1H, brs) 2.90–3.00 (5H, m)<br>3.28 (1H, dd, J=15.7 Hz, 9.4 Hz)<br>3.45–3.65 (2H, m) 4.85–5.00 (1H,<br>m) 6.74 (1H, d, J=7.9 Hz) 6.80–<br>6.90 (1H, m) 6.90 (1H, brs) 7.05–<br>7.20 (4H, m) 7.78 (2H, dd, J=8.9<br>Hz, 5.3 Hz)<br>315 (MH$^-$) |
| Example 22<br>Step A | 1.70–1.85 (2H, m) 2.60–2.85 (5H,<br>m) 3.21 (1H, dd, J=5.7 Hz, 9.1 Hz)<br>3.40–3.80 (4H, m) 4.90–5.00 (1H,<br>m) 0.56 (1H, d, J=7.9 Hz) 6.81<br>(1H, dd, J=7.6 Hz, 7.3 Hz) 7.00–<br>7.50 (1H, m) 7.70–7.80 (2H, m)<br>401 (MH$^+$) |
| Example 22<br>Step B | 1.75–1.90 (2H, m) 2.19 (1H, brs)<br>2.80–2.90 (5H, m) 3.26 (1H,dd, J=<br>15.5 Hz, 9.2 Hz) 3.50–3.70 (2H, m)<br>4.85–5.00 (1H, m) 6.74 (1H, d, J=<br>7.9 Hz) 6.80–6.90 (1H, m) 7.05–<br>7.20 (2H, m) 7.30–7.50 (3H, m)<br>7.80–7.90 (2H, m) 7.99 (1H, brs)<br>311 (MH$^-$) |
| Example 23<br>Step A | 1.65–1.85 (2H, m) 2.55–2.95 (5H,<br>m) 3.22 (1H, dd, J=15.5 Hz, 9.2 Hz)<br>3.40–3.75 (2H, m) 3.64 (1H, d, J=<br>13.5 Hz) 3.75 (1H, d, J=13.5 Hz)<br>4.85–5.00 (1H, m) 6.55 (1H, d, J=<br>7.9 Hz) 6.80–6.90 (1H, m) 7.00–<br>7.35 (10H, m) 7.38 (1H, brs) 7.70–<br>7.80 (2H, m)<br>419 (MH$^-$) |
| Example 23<br>Step B | 1.75–1.85 (3H, m) 2.80–3.00 (5H,<br>m) 3.26 (1H, dd, J=15.5 Hz, 9.2 Hz)<br>3.50–3.70 (2H, m) 4.85–5.00 (1H,<br>m) 6.73 (1H, d, J=7.9 Hz) 6.85<br>(1H, dd, J=7.6 Hz, 7.3 Hz) 7.00–<br>7.20 (4H, m) 7.80–7.90 (2H, m)<br>8.14 (1H, brs)<br>329 (MH$^+$) |
| Example 24 | 1.65–1.75 (4H, m) 2.31 (3H, S)<br>2.45–2.60 (3H, m) 2.77 (1H,dd, J=<br>13.4 Hz, 8.1 Hz) 2.89 (1H, dd, J =<br>15.7 Hz, 7.4 Hz) 3.25 (1H, dd. J =<br>15.5 Hz, 9.2 Hz) 3.47 (2H, d, t, J=<br>6.3 Hz, 6.3 Hz) 4.85–5.00 (1H, m)<br>6.75 (1H, d, J=7.9 Hz) 6.80 (1H,<br>brs) 6.82 (1H, dd, J=7.6 Hz, 7.3<br>Hz) 7.09 (1H, dd, J=7.9 Hz, 7.6 Hz)<br>7.15 (1H, d, J=7.3 Hz) 7.35–7.55<br>(3H, m) 7.75–7.80 (2H, m)<br>339 (MH$^+$) |
| Example 25 | 1.01 (3H, t, J=7.1 Hz) 1.50–1.80<br>(4H, m) 2.55–2.70 (5H, m) 2.81<br>(1H, dd, J =13.9 Hz, 7.6 Hz) 2.92<br>(1H, dd, J =15.5 Hz, 7.6 Hz) 3.24<br>(1H, dd, J =15.5 Hz, 9.2 Hz) 3.46<br>(2H, dt, J =6.6 Hz, 6.6 Hz) 4.85–<br>5.00 (1H, m) 6.54 (1H, brs) 6.74<br>(1H, d, J=7.9 Hz) 6.81 (1H, dd, J=<br>7.6 Hz, 7.3 Hz) 7.08 (1H, dd, J=<br>7.9 Hz, 7.6 Hz) 7.14 (1H, d, J=<br>7.3 Hz) 7.35–7.55 (3H, m) 7.70–<br>7.80 (2H, m)<br>353 (MH$^+$) |
| Example 26 | 1.70–1.85 (2H, m) 2.40 (3H, S)<br>2.54 (1H, dd, J=15.2 Hz, 3.6 Hz)<br>2.55–2.90 (4H, m) 3.23 (1H, dd, J=<br>15.5 Hz, 9.2 Hz) 3.50–3.75 (2H, m)<br>4.85–5.00 (1H,m) 6.51 (1H, d, J= |

TABLE 6-continued

| Compound | Physical properties<br>$^1$H-NMR (CDCl$_3$) δ(ppm)<br>MASS(FAB) |
|---|---|
| | 7.9 Hz) 6.81 (1H, dd, J=7.6 Hz,<br>7.3 Hz) 7.00–7.15 (2H, m) 7.35–<br>7.50 (3H, m) 7.85–7.90 (2H, m)<br>8.18 (1H, brs)<br>325 (MH$^+$) |
| Example 27<br>Step A | 1.40–1.55 (4H, m) 1.44 (9H, s)<br>2.85–3.00 (2H, m) 2.86 (1H, dd, J=<br>5.8 Hz, 7.3 Hz) 3.15–3.35 (5H, m)<br>4.93 (1H, brs) 6.74 (1H, d, J=<br>7.9 Hz) 6.84 (1H, dd, J=7.3 Hz,<br>7.3 Hz) 7.05–7.20 (5H, m) 7.85–<br>7.95 (2H, m)<br>479 (MH$^-$), 379 |
| Example 27<br>Step B | 1.30–1.65 (5H, m) 2.45–3.00 (8H,<br>m) 3.25 (1H, dd, J=15.5 Hz, 9.2 Hz)<br>4.85–5.00 (1H, m) 6.69 (1H, d, J=<br>7.9 Hz) 6.70–6.85 (1H, m) 7.00–<br>7.15 (6H, m) 7.79 (2H, dd, J=8.9<br>Hz, 5.0 Hz)<br>379 (MH$^+$) |
| Example 28<br>Step A | 1.44 (9H, s) 1.45–1.65 (4H, m)<br>2.86 (1H, dd, J=15.8 Hz, 7.3 Hz)<br>3.00–3.10 (2H, m) 3.15–3.35 (5H,<br>m) 4.93 (1H, brs) 6.73 (1H, d, J=<br>7.9 Hz) 6.84 (1H, dd, J=7.6 Hz,<br>7.3 Hz) 7.05–7.20 (2H, m) 7.72<br>(1H, dd, J=7.9 Hz, 7.9 Hz) 8.19<br>(1H, d, J=7.9 Hz) 8.41 (1H, d, J=7.9<br>Hz) 8.70 (1H, s)<br>506 (MH$^+$), 406 |
| Example 28<br>Step B | 1.40–1.80 (5H, m) 2.50–3.15 (7H,<br>m) 3.35 (1H, dd, J=15.5 Hz, 9.2 Hz)<br>5.00–5.15 (1H, m) 6.77 (1H, d, J=<br>7.9 Hz) 6.80–6.95 (1H, m) 7.17<br>(1H, d, J=7.3 Hz) 7.11 (1H, dd, J =<br>7.9 Hz, 7.6 Hz) 7.70 (1H, dd, J=<br>7.9 Hz, 7.9 Hz) 8.15–8.25 (1H, m)<br>8.35–8.45 (1H, m) 8.65–8.70 (1H,<br>m)<br>406 (MH$^-$) |
| Example 29<br>Step A | 1.45 (9H, s) 1.50–1.75 (4H, m)<br>2.30 (3H, s) 2.87 (1H, dd, J=<br>15.8 Hz, 6.9 Hz) 3.20–3.55 (7H, m)<br>4.96 (1H, brs) 6.74 (1H, d, J=<br>7.9 Hz) 6.83 (1H, dd, J=7.4 Hz,<br>7.4 Hz) 7.05–7.20 (3H, m) 7.25–<br>7.20 (1H, m) 7.35–7.50 (1H, m)<br>7.65–7.75 (1H, m)<br>483 (MH$^+$) 383 |
| Example 29<br>Step B | 1.50–1.70 (5H, m) 2.60–2.95 (5H,<br>m) 3.19 (1H, dd, J=15.5 Hz, 9.2 Hz)<br>3.37 (2H, t, J=6.3 Hz) 4.75–4.95<br>(1H, m) 6.65–6.95 (4H, m) 7.00–<br>7.15 (2H, m) 7.20–7.35 (2H, m)<br>7.55 (1H, brs)<br>383 (MH$^+$) |

We claim:

1. A 2,3-dihydrobenzofuran derivative represented by formula (1) or a salt thereof:

$$\text{[structure: 2,3-dihydrobenzofuran-CH}_2\text{—N(R}^1\text{)—(CH}_2\text{)}_n\text{—N(H)—A—phenyl-R}^2\text{]} \quad (1)$$

wherein R$^1$ represents a hydrogen atom or a lower alkyl group; n is an integer of from 2 to 6; A represents a carbonyl group or a sulfonyl group; R$^2$ represents a hydrogen atom, a halogen atom, a lower alkyl group which is unsubstituted or substituted with at least one halogen atom, a lower alkoxy group. a hydroxyl group. a nitro group. or a cyano group; and * represents an asymmetric carbon atom.

2. A method for producing a 2,3-dihydrobenzofuran derivative represented by formula (1) or a salt thereof:

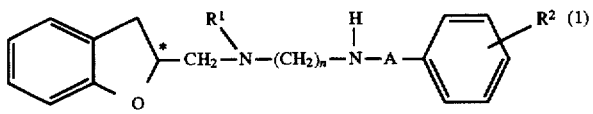

wherein $R^1$ represents a hydrogen atom or a lower alkyl group; n is an integer of from 2 to 6; A represents a carbonyl group or a sulfonyl group; $R^2$ represents a hydrogen atom, a halogen atom, a lower alkyl group which is unsubstituted or substituted with at least one halogen atom, a lower alkoxy group, a hydroxyl group, a nitro group, or a cyano group; and * represents an asymmetric carbon atom, which comprises reacting a compound represented by formula (2):

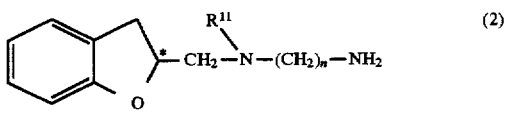

wherein * represents an asymmetric carbon atom; n is an integer of from 2 to 6; and $R^{11}$ represents an amino-protecting group or a lower alkyl group, with a compound represented by formula (3):

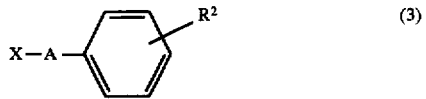

wherein $R^2$ represents a hydrogen atom, a halogen atom, a lower alkyl group which is unsubstituted or substituted with at least one halogen atom, a lower alkoxy group, a hydroxyl group, a nitro group, or a cyano group; A represents a carboxyl group or a sulfonyl group; and X represents a leaving atom or group, wherein when $R^{11}$ in formula (2) is an amino-protecting group, a product obtained by the reaction of said compound represented by formula (2) with said compound represented by formula (3) is subsequently subjected to a treatment for removing said amino-protecting group so that a hydrogen atom is substituted therefor.

3. A pharmaceutical composition for treating a serotonergic neuron-related disease, which comprises, as an active ingredient, a 2,3-dihydrobenzofuran derivative represented by formula (1) or a salt thereof:

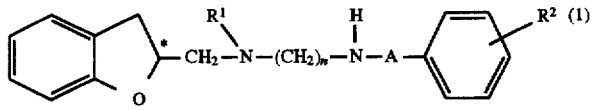

wherein $R^1$ represents a hydrogen atom or a lower alkyl group; n is an integer of from 2 to 6; A represents a carbonyl group or a sulfonyl group; $R^2$ represents a hydrogen atom, a halogen atom, a lower alkyl group which is unsubstituted or substituted with at least one halogen atom, a lower alkoxy group, a hydroxyl group, a nitro group, or a cyano group; and * represents an asymmetric carbon atom.

4. A method for treating a serotonergic neuron-related disease, which comprises administering to a patient suffering from a serotonergic neuron-related disease a pharmaceutical composition comprising a therapeutically effective amount of a 2,3-dihydrobenzofuran derivative represented by formula (1) or a non-toxic salt thereof:

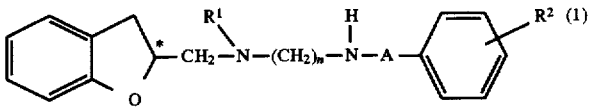

wherein $R^1$ represents a hydrogen atom or a lower alkyl group; n is an integer of from 2 to 6; A represents a carbonyl group or a sulfonyl group; $R^2$ represents a hydrogen atom, a halogen atom, a lower alkyl group which is unsubstituted or substituted with at least one halogen atom, a lower alkoxy group, a hydroxyl group, a nitro group, or a cyano group; and * represents an asymmetric carbon atom.

5. The derivative or the salt thereof according to claim 1, wherein n is 4.

6. The derivative or the salt thereof according to claim 1, wherein $R^1$ represents hydrogen.

7. The derivative or the salt thereof according to claim 1, wherein $R^1$ represents a methyl or ethyl group.

8. The pharmaceutical composition according to claim 3, further comprising an excipient.

9. The pharmaceutical composition according to claim 3, further comprising a diluent.

10. The pharmaceutical composition according to claim 9, wherein said composition is in the form of an aqueous solution.

11. The method according to claim 4, wherein said disease is selected from the group consisting of anxiety, depression, high blood pressure and emeses.

12. The method according to claim 11, wherein said disease is emeses.

13. The derivative or the salt thereof according to claim 1, wherein n is 4 and A represents a carbonyl group.

14. The derivative or the salt thereof according to claim 1, wherein n is 4 and $R^2$ represents a hydrogen atom or a fluorine atom.

15. The derivative or the salt thereof according to claim 1, wherein n is 4 and $R^2$ represents a chlorine atom, a bromine atom, a lower alkyl group which is unsubstituted or substituted with at least one halogen atom, a lower alkoxy group, a hydroxyl group, a nitro group, or a cyano group with a proviso that $R^2$ is bound to the benzene ring at a 3-position thereof.

16. The derivative or the salt thereof according to claim 1, wherein n is 4 and $R^2$ represents a methyl or methoxy group.

17. (−)-2-{N-(4-benzoylaminobutyl)}aminomethyl-2,3-dihydrobenzo[b]furan or a salt thereof.

18. A derivative selected from the group consisting of 2-{N-(4-benzoylaminobutyl)}aminomethyl-2,3-dihydrobenzo[b]furan, 2-{N-(4-benzenesulfonamidobutyl)}aminomethyl-2,3-dihydrobenzo[b]furan, 2,3-dihydro-2-[N-{4-(3-methylbenzoylamino)butyl}]aminomethylbenzo[b]furan, 2,3-dihydro-2-[N-{4-(3-methoxybenzoylamino)butyl}]aminomethylbenzo[b]furan, 2,3-dihydro-2-[N-{4-(2-fluorobenzoylamino)butyl}]aminomethylbenzo[b]furan, 2,3-dihydro-2-[N-{4-(3-fluorobenzoylamino)butyl}]aminomethylenzo[b]furan, 2,3-dihydro-2-[N-{4(4-fluorobenzoylamino)butyl}]aminomethylbenzo[b]furan, (+)-2-{N-(4-benzoylamino)butyl}aminomethyl-2,3-dihydrobenzo[b]furan, 2-{N-(3-benzoylaminopropyl)}aminomethyl-2,3-dihydrobenzo[b]furan, 2-{N-(4-benzoylaminobutyl)-N-methyl}aminomethyl-2,3-dihydrobenzo[b]furan and 2-(N-(4-benzoylaminobutyl)-N-ethyl}aminomethyl-2,3-dihydrobenzo[b]furan, or a salt thereof.

19. A derivative selected from the group consisting of 2,3-dihydro-2-[N-{4-(2-methylbenzoylamino)butyl}]

aminomethylbenzo[b]furan, 2,3-dihydro-2-[N-{4-(4-methylbenzoylamino)butyl}]aminomethylbenzo[b]furan, 2,3-dihydro-2-[N-{4-(2-methoxybenzoylamino)butyl}] aminomethylbenzo[b]furan, 2,3-dihydro-2-[N-{4-(4-methoxybenzoylamino)butyl}]aminomethylbenzo[b]furan, 2,3-dihydro-2-[N-{4-(2-trifluoromethylbenzoylamino) butyl}]aminomethylbenzo[b]furan, 2,3-dihydro-2-[N-{4-(3-trifluoromethylbenzoylamino)butyl}]aminomethylbenzo[b]furan, 2,3-dihydro-2-[N-{4-(4-trifluoromethylbenzoylamino)butyl}]aminomethylbenzo[b] furan, 2,3-dihydro-2-[N-{4-(3-nitrobenzoylamino)butyl}] amino-methylbenzo[b]furan, 2,3-dihydro-2-[N-{4-(3-cyanobenzoylamino)butyl}]aminomethylbenzo[b]furan, 2-{N-(2-benzoylaminoethyl)}aminomethyl-2,3-dihydrobenzo[b]furan, 2-[N-{2-(3-methylbenzoylamino) ethyl}]aminomethyl-2,3-dihydrobenzo[b]furan, 2-[N-{2-(4-fluorobenzoyl)aminoethyl}]aminomethyl-2,3-dihydrobenzo[b]furan, 2-[N-{3-(4-fluorobenzoylamino)propyl}]-aminomethyl-2,3-dihydrobenzo[b]furan, 2-{N-(3-benzoylaminopropyl)-N-methyl}aminomethyl-2,3-dihydrobenzo[b]furan, 2,3-dihydro-2-[N-{4-(4-fluorobenzenesulfonylamino)butyl}]aminomethylbenzo[b] furan, 2,3-dihydro-2-[N-{4-(3-nitrobenzenesulfonylamino) butyl}]aminomethylbenzo[b]furan and 2,3-dihydro-2-[N-{4-(2-hydroxy-benzoylamino)butyl}]aminomethylbenzo[b] furan, or a salt thereof.

20. The method according to claim 2, wherein said derivative or a salt thereof is (−)-2-{N-(4-benzoylaminobutyl)}aminomethyl-2,3-dihydrobenzo[b] furan or a salt thereof.

21. The pharmaceutical composition according to claim 3, wherein said derivative or a salt thereof is (−)-2-{N-(4-benzoylaminobutyl)}aminomethyl-2,3-dihydrobenzo[b] furan or a salt thereof.

22. The method according to claim 4, wherein said derivative or a salt thereof is (−)2-{N-(4-benzoylaminobutyl)}aminomethyl-2,3-dihydrobenzo[b] furan or a salt thereof.

* * * * *

UNITED STATES PATENT AND TRADEMARK OFFICE
CERTIFICATE OF CORRECTION

PATENT NO. : 5,792,791
DATED : August 11, 1998
INVENTOR(S) : Kogami et al

It is certified that error appears in the above-identified patent and that said Letters Patent is hereby corrected as shown below:

Column 58, claim 15 should be deleted and replaced with the following:

15. The derivative or the salt thereof according to claim 1, wherein n is 4 and $R^2$ represents a chlorine atom, a bromine atom, a lower alkyl group which is unsubstituted or substituted with at least one halogen atom, a lower alkoxy group, a hydroxyl group, a nitro group, or a cyano group with the proviso that $R^2$ is bound to the benzene ring at a 3-position thereof.

Signed and Sealed this

Sixteenth Day of February, 1999

Attest:

*Acting Commissioner of Patents and Trademarks*

*Attesting Officer*